US008524898B2

(12) United States Patent
Albericio et al.

(10) Patent No.: US 8,524,898 B2
(45) Date of Patent: Sep. 3, 2013

(54) PROTON ACCEPTOR IMINIUM/CARBOCATION-TYPE COUPLING AGENTS

(75) Inventors: Fernando Albericio, Barcelona (ES); Ayman El-Faham, Alexandria (EG); Yoav Luxembourg, Kfar-Shemaryahu (IL); Ariel Ewenson, Omer (IL)

(73) Assignee: Luxembourg Bio Technologies Ltd., Rechovot (IL)

( * ) Notice: Subject to any disclaimer, the term of this patent is extended or adjusted under 35 U.S.C. 154(b) by 678 days.

(21) Appl. No.: 12/451,496

(22) PCT Filed: May 15, 2008

(86) PCT No.: PCT/IL2008/000674
§ 371 (c)(1),
(2), (4) Date: Feb. 3, 2010

(87) PCT Pub. No.: WO2008/139481
PCT Pub. Date: Nov. 20, 2008

(65) Prior Publication Data
US 2010/0144588 A1  Jun. 10, 2010

Related U.S. Application Data

(60) Provisional application No. 60/924,475, filed on May 16, 2007, provisional application No. 60/929,384, filed on Jun. 25, 2007.

(51) Int. Cl.
*C07D 295/00* (2006.01)
(52) U.S. Cl.
USPC ......................................................... 544/162
(58) Field of Classification Search
None
See application file for complete search history.

(56) References Cited

U.S. PATENT DOCUMENTS

| | | | |
|---|---|---|---|
| 4,016,263 A * | 4/1977 | Wetzel et al. | 514/29 |
| 4,612,280 A * | 9/1986 | Okamura et al. | 430/621 |
| 4,618,573 A * | 10/1986 | Okamura et al. | 430/558 |
| 4,673,632 A * | 6/1987 | Okamura et al. | 430/510 |
| 5,166,394 A | 11/1992 | Breipohl et al. | |
| 6,825,347 B2 | 11/2004 | Carpino et al. | |
| 7,304,163 B2 | 12/2007 | Luxembourg et al. | |
| 2007/0043207 A1 | 2/2007 | Luxembourg et al. | |

FOREIGN PATENT DOCUMENTS

| | | |
|---|---|---|
| DE | 2606663 | 8/1977 |
| DE | 3516996 | 11/1985 |
| DE | 4122094 | * 2/1992 |
| JP | 05-341423 | 12/1993 |
| JP | 06-161015 | 6/1994 |
| JP | 06-194778 | 7/1994 |
| JP | 07-301880 | 11/1995 |
| JP | 2003-098621 | 4/2003 |
| WO | WO 94/07910 | 4/1994 |
| WO | WO 2007/020620 | 2/2007 |
| WO | WO 2008/139481 | 11/2008 |
| WO | WO 2009/138985 | 11/2009 |

OTHER PUBLICATIONS

Haynes, CRC Handbook of Chemistry and Physics, 2012, pp. 5-92 to 5-93.*
March, Advanced Organic Chemistry, 1992, pp. 250-252.*
Henklen. Peptides 1990, 1991, 67-68.*
Coste. Tetrahedron Letters, 1991, 32 (17), 1967-70.*
Chen. Tetrahedron Letters, 1992, 33 (5), 647-650.*
Habermann. Journal fur praktische Chemie Chemiker-Zeitung, 1998, 340, 233-239.*
International Preliminary Report on Patentability Dated Nov. 25, 2010 From the International Bureau of WIPO Re. Application No. PCT/IL2009/000486.
International Search Report and the Written Opinion Dated Nov. 19, 2010 From the International Searching Authority Re. Application No. PCT/IL2009/000486.
Translation of Office Action Dated Dec. 6, 2011 From the State Intellectual Property Office From the People's Republic of China Re. Application No. 200880024762.8.
International Search Report and the Written Opinion Dated Dec. 1, 2008 From the International Searching Authority Re.: Application No. PCT/IL2008/000674.
International Preliminary Report on Patentability Dated Nov. 26, 2009 From the International Bureau of WIPO Re.: Application No. PCT/IL2008/000674.
International Search Report Dated Dec. 1, 2008 From the International Searching Authority Re.: Application No. PCT/IL2008/000674.
Written Opinion Dated Dec. 1, 2008 From the International Searching Authority Re.: Application No. PCT/IL2008/000674.
Albericio et al. "New Trends in Peptide Coupling Reagents", Proceedings of the International Organic Report, p. 1-112, 2001.
Albericio et al. "Use of Onium Salt-Based Coupling Reagents in Peptide Synthesis", Journal of Organic Chemistry, 63: 9678-9683, 1998.
Carpino et al. "The Uronium/Guanidinium Peptide Coupling Reagents: Finally the True Uronium Salts", Angewandte Chemie, International Edition, 41(3): 441-445, 2002.
El-Faham et al. "Design and Synthesis of New Immonium-Type Coupling Reagents", European Journal of Organic Chemistry, XP002504591, 6: 1563-1573, 2006.
El-Faham et al. "Morpholine-Based Immonium and Halogenoamidinium Salts as Coupling Reagents in Peptide Synthesis", Journal of Organic Chemistry, XP002504595, 73(7): 2731-2737, 2008. p. 2732, col. 1, § 1, Scheme 1.

(Continued)

*Primary Examiner* — Noble Jarrell

(57) ABSTRACT

Novel iminium-type coupling agents containing proton acceptors in their iminium moiety, which can be used beneficially as coupling agents in various chemical polypeptide and/or polynucleotide syntheses, and are particularly useful as yield enhancing and racemization suppressing coupling agents for use in peptide syntheses, are disclosed. Further disclosed are a process of preparing such iminium-type coupling agents and their use in the preparation of polypeptides and/or polynucleotides.

44 Claims, 1 Drawing Sheet
(1 of 1 Drawing Sheet(s) Filed in Color)

(56) References Cited

OTHER PUBLICATIONS

El-Faham et al. "Novel Proton Acceptor Immonium-Type Coupling Reagents: Appliction in Solution and Solid-Phase Peptide Synthesis", Organic Letters, XP002504590, 9(22): 4475-4477, 2007.
Han et al. "Recent Development of Peptide Coupling Reagents in Organic Synthesis", Tetrahedron, 60(672): 2447-2467, 2004. p. 2450, col. 1, § 3, Fig.5.
Hoffmann et al. "Synthesis and Chemical Constitution of Diphenoxyphosphoryl Derivatives and Phosphonium Salts as Coupling Reagents for Peptide Segment Condensation", Phosphorus, Sulfur and Silicon and the Related Elements, 178(2): 299-309, 2003.
Itoh "Peptides. IV. Racemization Suppression by the Use of Ethyl 2-I lydriximino-2-Cyanoacetate and Its Amide", Bulletin of the Chemical Society of Japan, 46: 2219-2221, Jul. 1973.
Itoh "Peptides. V. Some Carbonates of Ethyl 2-Hydroximino-2-Cyanoacetate and Related Compounds as Esterification Reagents for Peptide Synthesis", Bulletin of the Chemical Society of Japan, 47(2): 471-475, Feb. 1974.
Itoh et al. "Peptides. VI. Some Oxime Carbonates as Novel T-Butoxycarbonylating Reagents", Bulletin of the Chemical Society of Japan, 50(3): 718-721, Mar. 1977.
Izdebski "New Reagents Suppressing Racemization in Peptide Synthesis by the DCC Method", Polish Journal of Chemistry (Formerly Roczniki Chemii), 53: 1049-1057, 1979.
Li et al. "The Development of Highly Efficient Onium-Type Peptide Coupling Reagents Based Upon Rational Molecular Design", Journal of Peptide Research, XP001039108, 58(2): 129-139, Aug. 1, 2001.
Senning "N-Methoniumanaloge Thiouroniumverbindungen", Acta Chemica Scandinavica, XP002504592, 19(8): 1993-1995, 1965. Tables 2, 3.
Communciation Pursuant to Article 94(3) EPC Dated Aug. 8, 2011 From the European Patent Office Re. Application No. 08751362.8.
Response Dated Dec. 8, 2011 to Communciation Pursuant to Article 94(3) EPC of Aug. 8, 2011 From the European Patent Office Re. Application No. 08751362.8.
Office Action Dated Aug. 15, 2012 From the Israel Patent Office Re. Application No. 202117 and Its Translation Into English.
Office Action Dated Sep. 10, 2012 From the Israel Patent Office Re. Application No. 209300 and Its Translation Into English.
Office Action Dated Feb. 1, 2013 From the State Intellectual Property Office From the People's Republic of China Re. Application No. 200880024762.8 and Its Summary and Translation Into English.

\* cited by examiner

PROTON ACCEPTOR IMINIUM/CARBOCATION-TYPE COUPLING AGENTS

RELATED APPLICATIONS

This Application is a National Phase of PCT Patent Application No. PCT/IL2008/000674 having International filing date of May 15, 2008, which claims the benefit of U.S. Provisional Patent Application Nos. 60/929,384 filed on Jun. 25, 2007 and 60/924,475 filed on May 16, 2007. The contents of the above Applications are all incorporated herein by reference.

FIELD AND BACKGROUND OF THE INVENTION

The present invention, in some embodiments thereof, relates to coupling agents and, more particularly, but not exclusively, to the preparation and use of novel coupling agents that can be beneficially utilized in the syntheses of substances such as peptides and oligonucleotides.

Therapeutic peptides, or pharmaceutical peptides, take an ever-growing cut in the active pharmaceutical ingredients (API) market, particularly as, for example, antibiotics, hormones, immunomodulators, anti-angiogenesis agents, therapeutic agents for treating CNS and other neurological disorders, analgesics, anti-obesity drugs, and as therapeutic agents for treating immune disorders such as allergy, asthma, hemophilia, anemia and autoimmune diseases [for a review, see, Loffet, A., "*Peptides as Drugs: Is There a Market?*", 2002, *J. Peptide Sci.* 8, 1]. According to a Frost & Sullivan report, there are currently more than 40 marketed peptide drugs worldwide, around 270 peptides in clinical phase testing, and about 400 in advanced preclinical phases. Peptides represent 1% of all total API with a market share estimated at US$300-500 M per year and an annual growth rate of 15-25%. It is expected that the market will double in the next few years, when generic and recently approved new chemical entities enter the market.

However, although peptides have enormous therapeutic potential, their widespread use has been limited by several restrictive technical factors. Today, manufacturing companies face the unprecedented challenge of producing hundred kilograms to tons quantities of complex peptides. Such a massive production typically uses expensive and complex modern technologies, rendering peptide manufacture difficult and cost-inefficient as compared with other "small-molecule" pharmaceuticals. Large-scale manufacturing and purification of peptides in a bioactive form can therefore be a limiting step in the commercialization of peptide-based drugs.

A key step in the peptide production process is the controlled formation of a peptide bond (an amide bond formed between a carboxylic acid group and an amine group) between two amino acids (the so-called "coupling" reaction). In peptide syntheses, formation of a peptide bond typically requires proper management of protecting groups, and the activation of the carboxylic acid, or a carboxyl group in general, which usually involves the use of a peptide coupling agent [for a comprehensive review on peptide coupling agents see, F. Albericio, S. A. Kates, Solid-Phase Synthesis: A Practical Guide, S. A. Kates, F. Albericio Eds; Marcel Dekker, New York, N.Y., 2000, pp. 273-328 and F. Albericio, R. Chinchilla, D. J. Dodsworth, C. Nájera, 2001, *Org. Prep. Proc. Int.*, 33, 202].

Phosphate groups can also be activated in a way similar to the activation of carboxyl groups for coupling to amino groups in peptide synthesis. The activation of phosphate groups is an essential step in the synthesis of various nucleic acids and oligonucleotides used to build DNA and RNA, as well as molecules which mimic the chemical structure and thus the activity of the latter, which can be effected by a diverse group of activating or coupling reagents. Such activating reagents and reaction conditions which can be used for activation of phosphate groups are described in the art of peptide synthesis (see for example, L. Carpino. (1997) *Methods in Enzymology,* 289: 104 and WO 2006/063717) as discussed herein.

Although the synthesis of medium-large peptides for basic research is a well established procedure, the combination of the 20 naturally occurring amino acids and a growing number of unnatural amino acids makes each peptide synthesis unique at the industrial level, oftentimes requiring closer attention to each amino acid coupling. Some of the rules for coupling agents validated in the research scale can be applied at industrial level, but the results are still hardly predictable.

The two main classes of coupling techniques involve (a) those that require in situ activation of the carboxylic acid and (b) those that depend on an activated amino-acid species that has previously been prepared, isolated, purified, and characterized. The first type is by far the most convenient for the stepwise elongation of a peptide chain and is the more commonly used in convergent processes, where protected peptides are used instead of protected amino acids.

As mentioned herein, the role of the coupling agent is the activation of the carboxyl group of one amino acid which facilitates its coupling with the amino group of another amino acid. The process of activation is probably the one aspect of peptide synthesis which has been most extensively developed in recent years. An essential feature of all coupling methods is that, in addition to improving the yield of the peptide-bond formation, the configurational integrity of the carboxylic component must be maintained as well, namely no racemization should occur at any of the amino acid chiral centers.

This duality in coupling agent requirements, i.e. high peptide-bond formation yield and absence of amino acid racemization, is often difficult to achieve, since usually the most effective peptide-bond formation methods involve conversion of the acid to an intermediate bearing a good leaving group. Such leaving groups tend to increase the acidity of the α-proton of the activated amino acid, enhancing deprotonation and formation of an oxazolone, both of which lead to loss of the stereo-configuration.

Racemization is a side-reaction that occurs during the preparation of a peptide. In a production scale, the formation of small amounts of epimers can be difficult to detect and more importantly, it makes the removal of these impurities very challenging in any scale and particularly in large industrial scale processes. This constitutes one of the most serious drawbacks for the implementation of peptides as API's.

The currently most-widely used coupling reagents include carbodiimides on the one hand, and phosphonium and iminium salts on the other. It is noteworthy that coupling agents that are useful in peptide synthesis can also be used in other organic syntheses that require activation of a carboxylic moiety. Such syntheses can be used to produce organic compounds of biological interest such as, for example, peptoids, oligocarbamates, oligoamides, β-lactams, esters, polyenamides, benzodiazepines, diketopiperazines, and hydantoins.

Carbodiimides are presently the most available and low-cost coupling agents amongst the presently known reagents, and include dicyclohexylcarbodiimide (DCC), 1-ethyl-3-(3'- dimethylaminopropyl)carbodiimide (EDC) and N,N'-diisopropylcarbodiimide (DIC). The primary reactive species, O-acylisourea, is one of the most reactive species for peptide coupling. Shortcomings associated with the use of carbodiimides as coupling agents therefore mostly stem from the high and relatively uncontrollable reactivity thereof and include, for example, racemization, side reactions and low yields due to the formation of the poorly active N-acyl urea. Furthermore, while low dielectric constant solvents such as $CHCl_3$ or $CH_2Cl_2$ are optimal for carbodiimides, the use of solvents which exhibit a higher dielectric constant such as DMF, which favor the formation of the N-acyl urea, precludes their use alone. Furthermore, dicyclohexylcarbodiimide is also incompatible with Fmoc/t-Bu solid-phase chemistry, because the urea derivative formed in such syntheses is typically not soluble in common solvents. Such urea derivatives are also difficult to remove in solution chemistry.

At the beginning of the 70's, 1-hydroxybenzotriazole (HOBt) was proposed as an additive to DCC. The addition of HOBt was aimed at reducing the racemization associated with DCC coupling. The relative success of this additive signaled the beginning of a period during which other benzotriazole derivatives such as 1-hydroxy-6-chlorobenzotriazole (6-Cl-HOBt) and 1-hydroxy-7-azabenzotriazole (HOAt) were developed and successfully used. During later years the addition of benzotriazole derivatives as additives to DCC and other carbodiimides became almost mandatory to safeguard the peptide bond formation by carbodiimide activation from low yields, undesired side reactions and loss of chirality.

In the last decade, the use of phosphonium and iminium/uronium salts, referred to herein in short as "onium salts", of hydroxybenzotriazole derivatives as peptide coupling agents, was introduced. Although these reagents have been rapidly adopted for research purposes, only a few of them have been found compatible with current industrial requirements and synthetic strategies and were adopted by the industry. The species that reacts with onium salts is the carboxylate of the amino/organic acid. Therefore, performing the coupling reaction in the presence of at least one equivalent of a base is essential while using these reagents. The most reactive iminium salt coupling agent at present is 1-[bis(dimethylamino)methylene]-1H-1,2,3-triazolo-[4,5-b]pyridinium hexafluorophosphate 3-oxide (HATU).

The misconception regarding the structure of these and other coupling agents was settled by Carpino, L. A. et al. [*Angew. Chem. Int. Ed.* 2002, 41, No. 3, p. 441], and it is now accepted that the leaving group in these agents is linked to the iminium moiety via the triazole nitrogen and not via the oxygen, which remains in its N-oxide form. The chemical structures of HATU and analogs thereof are presented in Scheme 1 below.

Scheme 1

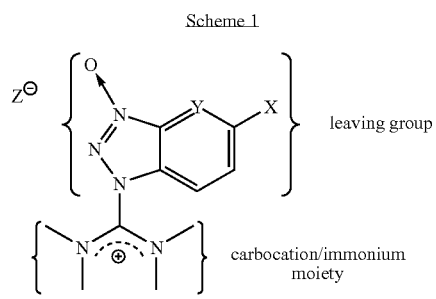

leaving group carbocation/immonium moiety

|      | X  | Y  | Z   |
|------|----|----|-----|
| HATU | H  | N  | $PF_6$ |
| HBTU | H  | CH | $PF_6$ |
| TBTU | H  | CH | $BF_4$ |
| HCTU | Cl | CH | $PF_6$ |
| TCTU | Cl | CH | $BF_4$ |

Iminium salts, such as HATU, TBTU, HBTU, HCTU, or TCTU, which are possibly the most powerful coupling agents known are formed by a leaving group and a carbocation skeleton. However, the presently known peptide coupling agents are typically limited by their low desired reactivity, side products formed thereby and/or high cost.

U.S. Pat. No. 6,825,347 and WO 94/07910 teach uronium and iminium salts and their use in effecting the acylation step in amide formation, especially during peptide synthesis. The coupling agents taught in these publications have a leaving group attached to an uronium and iminium moiety, which is characterized by having N-alkyl or P-alkyl substituted nitrogen or phosphor atoms. These coupling agents, while being innovative, still provide coupling efficiencies similar to previously known coupling agents.

Phosphonium-based coupling agents are gathering grounds in the industry, and include 7-azabenzotriazol-1-yl-N-oxy-tris(pyrrolidino)phosphonium hexafluorophosphate (PyAOP), and benzotriazol-1-yl-N-oxy-tris(pyrrolidino)phosphonium hexafluorophosphate (PyBOP). However, these are only marginally more effective than their carbocation/iminium counterparts and thus are oftentimes forbiddingly yet unjustifiably more expensive coupling agents. Recently, 6-chloro-1-hydroxybenzotriazol-1-yl-N-oxy-tris(pyrrolidino)phosphonium hexafluorophosphate (PyClock), one of the most effective phosphonium-based coupling agents, was introduced by the present assignee (see, for example, WO 2007/020620).

SUMMARY OF THE INVENTION

In a search for novel coupling agents, the present inventors have designed, prepared and successfully practiced a novel family of coupling agents which are more effective and safer than commonly used coupling agents, and are simple and safe to produce and use in modern peptide and oligonucleotide synthesis techniques.

Thus, according to an aspect of some embodiments of the present invention there is provided a coupling agent having a general formula selected from the group consisting of:

Formula I

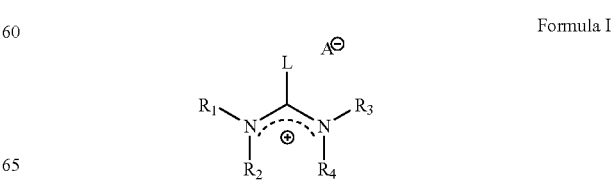

Formula II

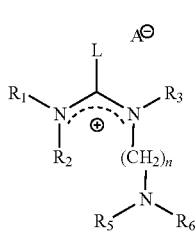

wherein:
A is an inorganic anion;
L is a leaving group;
n is an integer from 1 to 4,
each of $R_1$, $R_2$, $R_3$, $R_4$, $R_5$ and $R_6$ is independently selected from the group consisting of an alkyl having 1-4 carbon atoms and an alkyl having 1-4 carbon atoms interrupted, substituted and/or terminated by at least one heteroatom, or, alternatively, $R_1$ and $R_2$, and/or $R_3$ and $R_4$, and/or $R_5$ and $R_6$ are each independently joined to form a heteroalicyclic moiety, provided that at least one of $R_1$, $R_2$, $R_3$, $R_4$, $R_5$ and $R_6$ is an alkyl having 1-4 carbon atoms interrupted, substituted and/or terminated by at least one heteroatom and/or at least one of $R_1$ and $R_2$, and/or $R_3$ and $R_4$, and/or $R_5$ and $R_6$ are joined to form a heteroalicyclic moiety.

According to some embodiments of the invention, the heteroatom is selected from the group consisting of O, S, N, P and B.

According to some embodiments, the heteroalicyclic moiety is selected from the group consisting of a pyrrolidine, a piperidine, morpholine, a thiomorpholine, an imidazolidine, an azaphosphinane, an azaphospholidine, an azaborinane, an azaborolidine, an azaphosphinane, an azaphospholidine and a piperazine. For example, the heteroalicyclic moiety is morpholine.

According to some embodiments, the inorganic anion is selected from the group consisting of halide, hexahalophosphate, hexahaloantimonate, tetrahaloborate, trihalomethanesulfonate and bis(trihalomethylsulfonyl)imide. For example, the inorganic anion is hexafluorophosphate.

According to some embodiments, the leaving group is selected from the group consisting of halo, acetate, tosylate, triflate, sulfonate, azide, hydroxy, thiohydroxy, alkoxy, cyanate, thiocyanate, nitro, cyano, a benzotriazole, a benzotriazinone, a succinimide, a ketoxime, a pyridin-2(1H)-one-1-oxy, a quinazolin-4(3H)-one-3-oxy, a 1H-benzo[d]imidazol-1-oxy, an imidazole, an indolinone-1-oxy, pentafluorophenol, pentafluorothiophenol, 2-nitrophenol and 2-nitrobenzenethiol.

According to some embodiments, the benzotriazole has the general Formula III:

Formula III

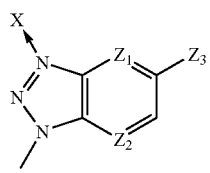

wherein:
X is O or S;
$Z_1$ and $Z_2$ are each independently CH or N; and
$Z_3$ is F, Cl, Br, $CF_3$ or $NO_2$.

According to some embodiments, X is O or S; $Z_1$ and $Z_2$ are each CH; and $Z_3$ is Cl. Preferably X is O.

According to some embodiments, X is O or S; $Z_1$ and $Z_2$ are each CH; and $Z_3$ is $CF_3$ or $NO_2$. For example, X is O; and $Z_3$ is $CF_3$ or $NO_2$.

According to some embodiments, the benzotriazinone has the general Formula IV:

Formula IV

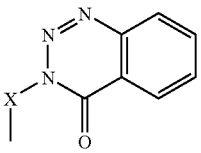

wherein X is O or S.

According to some embodiments, the succinimide has the general Formula V:

Formula V

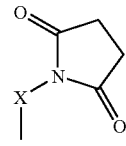

wherein X is O or S.

According to some embodiments, the ketoxime has the general Formula VI:

Formula VI

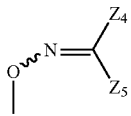

wherein:
$Z_4$ and $Z_5$ are each independently selected from the group consisting of F, Cl, Br, CORa, COORa, CONRa, CN, $CF_3$ or $NO_2$; and Ra is alkyl.

According to some embodiments, $Z_4$ is COORa; Ra is ethyl; and $Z_5$ is CN. According to other embodiments, both $Z_4$ and $Z_5$ are COORa with Ra as ethyl. According to other embodiments, both $Z_4$ and $Z_5$ are CN. According to still other embodiments, $Z_4$ and $Z_5$ are each independently COORa or CN and Ra is ethyl or methyl.

According to some embodiments, the pyridin-2(1H)-one-1-oxy has the general Formula VII:

Formula VII

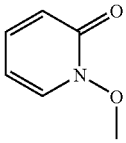

According to some embodiments, the quinazolin-4(3H)-one-3-oxy has the general Formula VIII:

Formula VIII

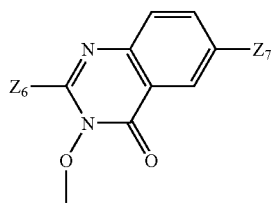

wherein $Z_6$ and $Z_7$ are each independently selected from the group consisting of H, F, Cl, Br, CN, $CF_3$, $NO_2$, aryl or alkyl. According to further features in some embodiments, $Z_6$ is $CH_3$; and $Z_7$ is Cl.

According to some embodiments, the 1H-benzo[d]imidazol-1-oxy has the general Formula IX:

Formula IX

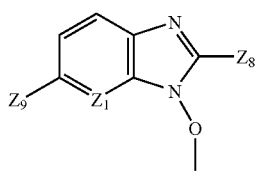

wherein $Z_1$ is CH or N, and $Z_8$ and $Z_9$ are each independently selected from the group consisting of H, F, Cl, Br, CN, $CF_3$, $NO_2$, aryl or alkyl. According to some embodiments $Z_1$ is CH, $Z_8$ is phenyl, and $Z_9$ is H or Cl. According to other embodiments, $Z_1$ is N, $Z_8$ is methyl and $Z_9$ is H.

According to some embodiments, the indolinone-1-oxy has the general Formula X:

Formula X

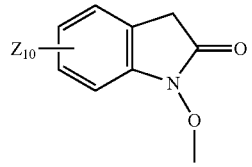

wherein $Z_{10}$ is selected from the group consisting of H, F, Cl, Br, CN, $CF_3$, $NO_2$, aryl or alkyl.

According to some embodiments of the present invention there is provided a coupling agent selected from the group consisting of:

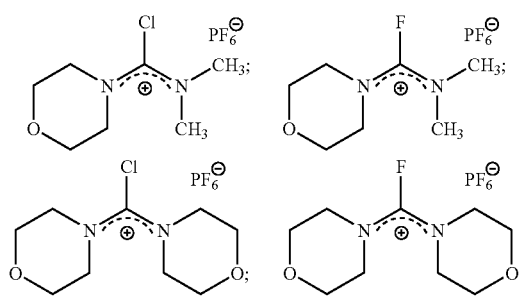

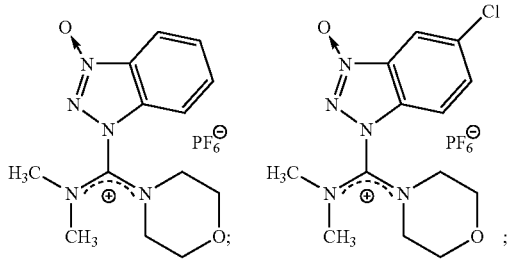

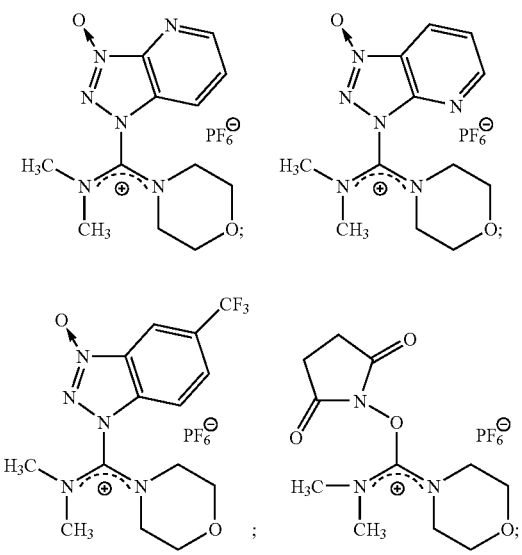

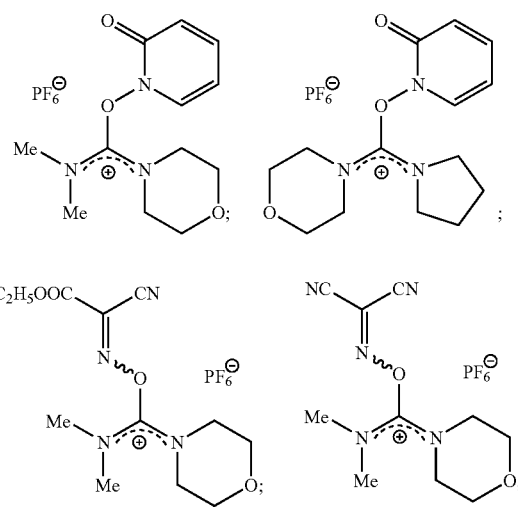

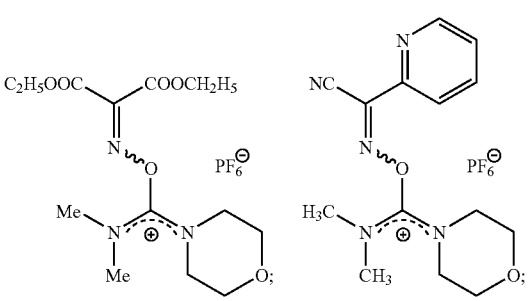

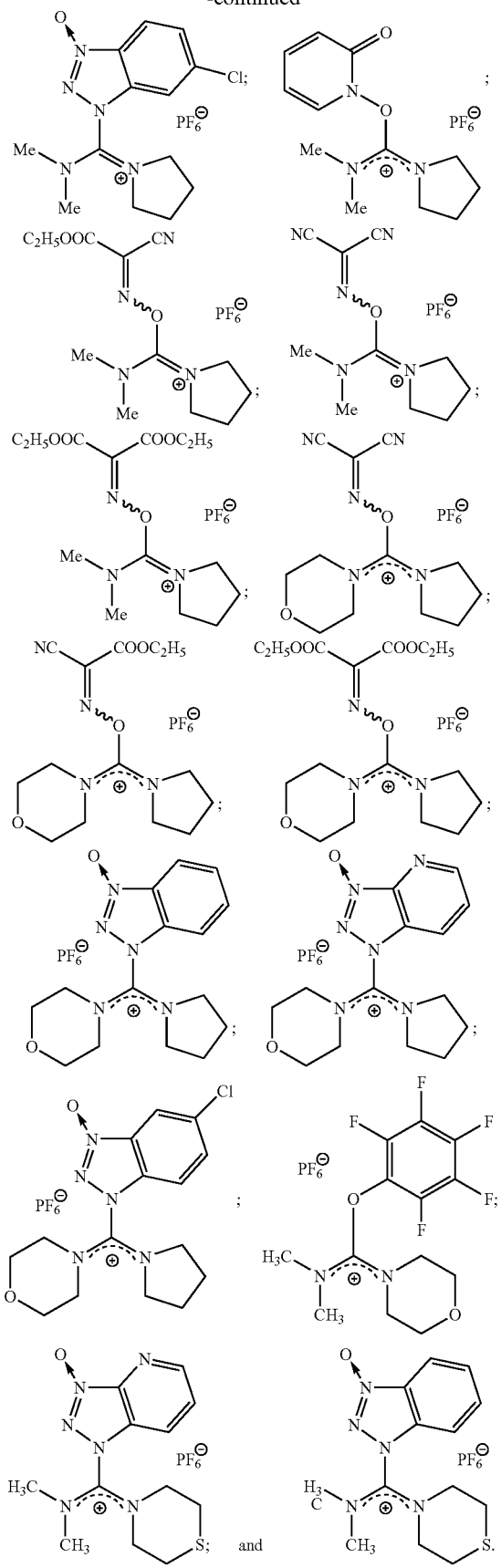

According to some embodiments of the present invention there is provided a process of preparing the coupling agent described herein, the process comprising:

contacting a compound having a general formula selected from the group consisting of:

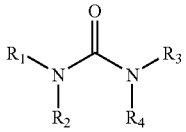

Formula XI

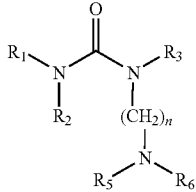

Formula XII wherein each of $R_1$, $R_2$, $R_3$, $R_4$, $R_5$ and $R_6$ is independently selected from the group consisting of an alkyl having 1-4 carbon atoms and an alkyl having 1-4 carbon atoms interrupted, substituted and/or terminated by at least one heteroatom, or, alternatively, $R_1$ and $R_2$, and/or $R_3$ and $R_4$, and/or $R_5$ and $R_6$ are each independently joined to form a heteroalicyclic moiety, provided that at least one of $R_1$, $R_2$, $R_3$, $R_4$, $R_5$ and $R_6$ is an alkyl having 1-4 carbon atoms interrupted, substituted and/or terminated by at least one heteroatom and/or at least one of $R_1$ and $R_2$, and/or $R_3$ and $R_4$, and/or $R_5$ and $R_6$ are joined to form a heteroalicyclic moiety; and n is an integer from 1 to 4;

with:

(i) a halogenating agent; and
(ii) a saturated aqueous solution of the inorganic anion;

to thereby obtain the coupling agent presented herein, wherein L is halo.

According to some embodiments, the process further includes, prior to the contacting:

reacting a compound having the general Formula XIII:

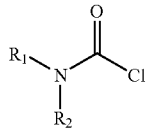

Formula XIII wherein each of $R_1$ and $R_2$ is independently selected from the group consisting of an alkyl having 1-4 carbon atoms and an alkyl having 1-4 carbon atoms interrupted, substituted and/or terminated by at least one heteroatom, or $R_1$ and $R_2$ are joined to form a heteroalicyclic moiety;

with a compound having the general Formula XIV:

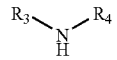

Formula XIV wherein each of $R_3$ and $R_4$ is independently selected from the group consisting of an alkyl having 1-4 carbon atoms and an alkyl having 1-4 carbon atoms interrupted, substituted and/or terminated by at least one heteroatom, or $R_3$ and $R_4$ are joined to form a heteroalicyclic moiety;

in the presence of a base, to thereby obtain the compound having the general Formula XI;

or with a compound having the general Formula XV:

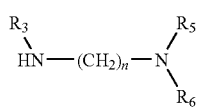

wherein:

wherein each of $R_3$, $R_5$ and $R_6$ is independently selected from the group consisting of an alkyl having 1-4 carbon atoms and an alkyl having 1-4 carbon atoms interrupted, substituted and/or terminated by at least one heteroatom, or $R_5$ and $R_6$ are joined to form a heteroalicyclic moiety;

n is an integer from 1 to 4;

in the presence of a base, to thereby obtain the compound having the general Formula XII.

According to some embodiments, the process further includes reacting the coupling agent wherein L is halo with a precursor compound of the leaving group in the presence of triethylamine.

According to some embodiments, the leaving group is selected from the group consisting of acetate, tosylate, triflate, sulfonate, azide, hydroxy, thiohydroxy, alkoxy, cyanate, thiocyanate, nitro, cyano, a benzotriazole, a benzotriazinone, a succinimide, a ketoxime, pentafluorophenol, pentafluorothiophenol, 2-nitrophenol and 2-nitrobenzenethiol.

According to some embodiments of the present invention there is provided a method of synthesizing a peptide, the method is effected by coupling a plurality of amino acids sequentially, one with another, in the presence of the coupling agent as presented herein, to thereby obtain a peptide containing the plurality of amino acids.

According to some embodiments, a rate of racemization per each coupling step ranges from 8% to 0.3%.

According to some embodiments, a yield of coupling per each coupling step ranges from 80% to 99%.

According to some embodiments of the present invention there is provided a method of synthesizing a polynucleotide, which is effected by coupling a plurality of nucleotides sequentially, one with another, in the presence of the coupling agent as presented herein, to thereby obtain a polynucleotide containing said plurality of nucleotides.

According to some embodiments, the synthesis of either a peptide or a polynucleotide is effected by a solid phase synthesis.

According to some embodiments, the synthesis of either a peptide or a polynucleotide is effected by a solution phase synthesis.

According to some embodiments of the present invention there is provided a crude composition of peptides, the peptides being synthesized in a C-terminus to N-terminus direction from a plurality of amino acids, the composition consisting essentially of a peptide having a desired amino acid sequence and a plurality of peptides having undesired amino acid sequences and being impurities to the peptide having the desired amino acid sequence, wherein a concentration of the peptide having the desired amino acid sequence in the composition is at least 5% above a concentration of an identical peptide having the desired amino acid sequence, in a composition of peptides being synthesized in the C-terminus to N-terminus direction using the coupling agent presented herein as a coupling agent, otherwise prepared under identical conditions.

According to some embodiments, the crude composition of peptides being in a form selected from the group consisting of a powdered composition, a lyophilized composition, a composition bound to a solid support, a solubilized composition and a dissolved composition.

According to some embodiments, at least one of the amino acids is selected from the group consisting of an amino acid having a secondary alpha amine, an amino acid having a tertiary alpha amine, an amino acid having a substituted alpha carbon atom, an amino acid having a substituted alpha amine, an amino acid having an amino-containing side chain, and any combination thereof.

According to some embodiments, the alpha carbon is substituted by an alkyl.

According to some embodiments, the amino acid having a substituted alpha carbon atom is α-aminoisobutyric acid (Aib)

According to some embodiments, the amino acid having a substituted alpha amine is phenylglycine (Phg).

According to some embodiments, the amino acid having an amino-containing side chain is arginine.

According to some embodiments, the synthesis of either a peptide or a polynucleotide is effected by a solid phase synthesis.

According to some embodiments, the synthesis of either a peptide or a polynucleotide is effected by a solution phase synthesis.

As used herein, the singular form "a", "an" and "the" include plural references unless the context clearly dictates otherwise. For example, the term "a protein" or "at least one protein" may include a plurality of proteins, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein throughout, the term "comprising" means that other steps and ingredients that do not affect the final result can be added. This term encompasses the terms "consisting of" and "consisting essentially of".

The term "method" or "process" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Herein throughout, the following abbreviations are used:

BOP for Benzotriazole-1-yl-oxy-tris-(dimethylamino)-phosphonium hexafluorophosphate;

Cl-HOBt for 6-chloro-1-hydroxybenzotriazole;

DCC for N,N'-dicyclohexylcarbodiimide, dicyclohexylcarbodiimide;

DIBOC for di-t-butyl dicarbonate;

DIEA for N,N-Diisopropylethylamine;

DIC, DIP or DIPCDI for N,N'-diisopropylcarbodiimide or 1,3-Diisopropylcarbodiimide;

DMAP for 4-Dimethylaminopyridine;

DMF for N,N-dimethylformamide;

EDC for 1-ethyl-3-(3'-dimethylaminopropyl)carbodiimide;

EDC HCl for 1-(3-Dimethylaminopropyl)-3-ethyl-carbodiimide hydrochloride;

Fmoc for 9-fluorenylmethoxycarbonyl;

HATU for 2-(7-Aza-1H-benzotriazole-1-yl)-1,1,3,3-tetramethyluronium hexafluorophosphate or 1-[bis(dimethylamino)methylene]-1H-1,2,3-triazolo-[4,5-b]pyridinium hexafluorophosphate 3-oxide;

HBTU for 2-(1H-Benzotriazole-1-yl)-1,1,3,3-tetramethyluronium hexafluorophosphate or 1-[bis(dimethylamino)methylene]-1H-benzotriazolium hexafluorophosphate 3-oxide;

HCTU, N-[(1H-6-chlorobenzotriazol-1-yl)-1,1,3,3-tetramethyluronium hexafluorophosphate HMPyOP for 1-(morpholino(2-oxopyridin-1(2H)-yloxy)methylene)pyrrolidinium hexafluorophosphate HDMOCC for 1-[(1-(cyano-2-ethoxy-2-oxoethylideneaminooxy)-dimethylamino-morpholinomethylene)]methanaminium hexafluorophosphate HDMODC for 1-[(1-(dicyanomethyleneaminooxy)-dimethylamino-morpholinomethylene)]methanaminium hexafluorophosphate HDMODeC for 1-[(1,3-diethyoxy-1,3-dioxopropan-2-ylideneaminooxy)-dimethylamino-morpholinomethylene)]methanaminium hexafluorophosphate HDMOPC for N-[(cyano(pyridine-2-yl)methyleneaminooxy)(dimethylamino) methylene)-N-morpholinomethanaminium hexafluorophosphate HOAt for 1-hydroxy-7-azabenzotriazole;

HOBt for 1-hydroxybenzotriazole;

HPTU for N-[(dimethylamino)-1H-1,2,3-triazolo-[4.5-beta]pyddino-1-ylmethylene]-N-methylmethanaminium hexafluorophosphate;

PyAOP for 7-azabenzotriazol-1-yl-N-oxy-tris(pyrrolidino)phosphonium hexafluorophosphate;

PyBOP for benzotriazol-1-yl-N-oxy-tris(pyrrolidino)phosphonium hexafluorophosphate;

TBTU for N-[(1H-benzotriazol-1-yl)(dimethylamino)methylene]-N-methylmethanaminium tetrafluoroborate N-oxide or 2-(1H-Benzotriazole-1-yl)-1,1,3,3-tetramethyluronium tetrafluoroborate;

TCTU, N-[(1H-6-chlorobenzotriazol-1-yl)(dimethylamino)methylene]-N-methylmethanaminium tetrafluoroborate N-oxide;

TFA for trifluoroacetic acid;

TFFH for Fluoro-N,N,N'',N''-tetramethylformamidinium hexafluorophosphate;

TCP for 2,4,6-trimethylpyridine (collidine); and

TNBSA for trinitrobenzenesulfonic acid.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
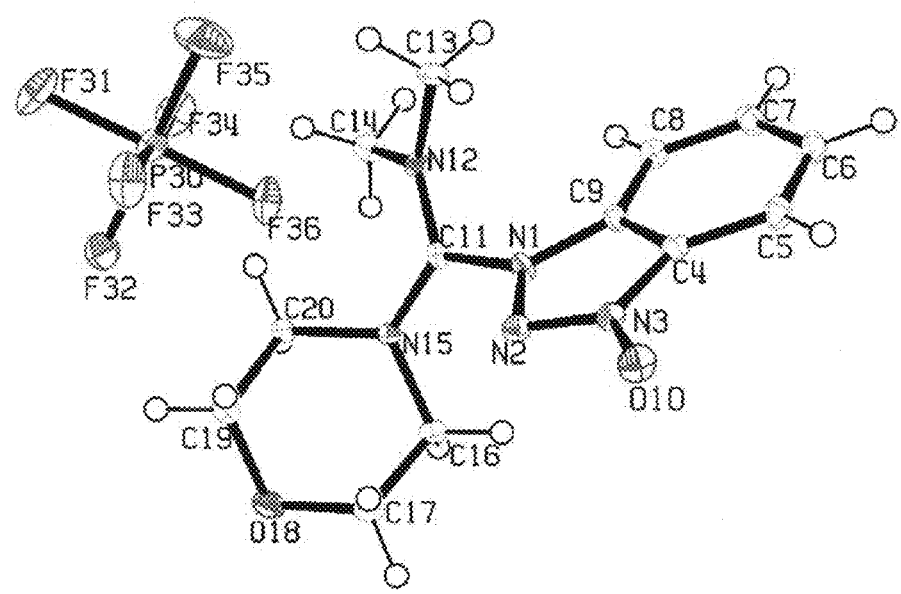
Figure 2:
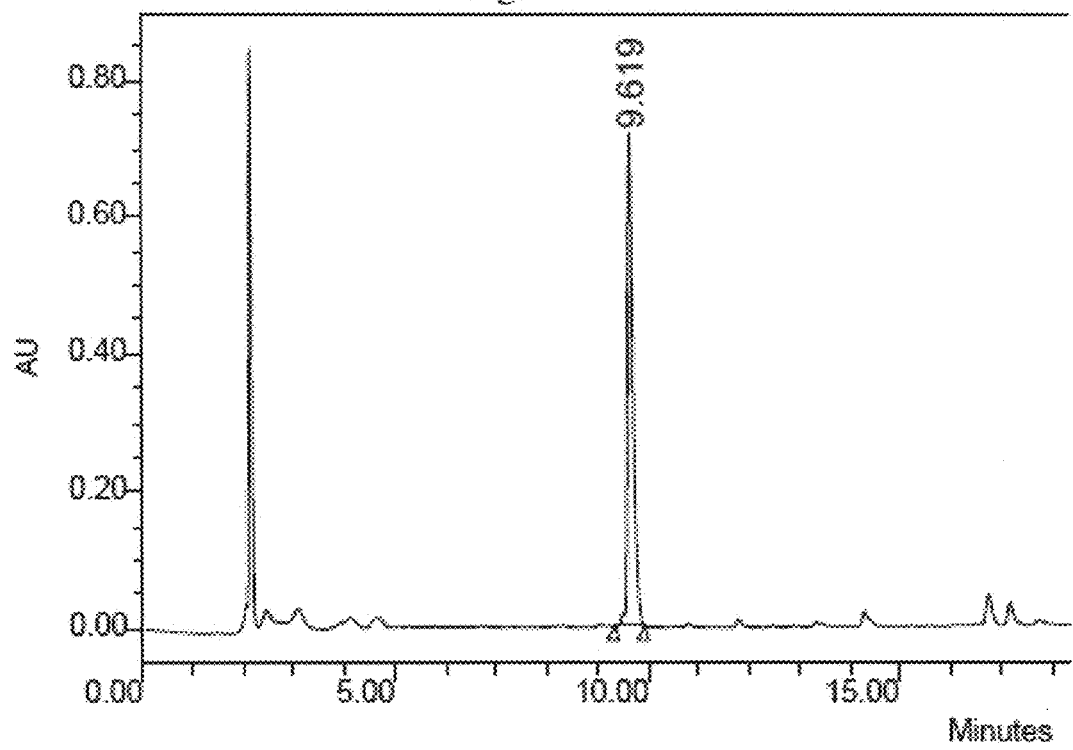

FIG. 1 presents the X-ray crystal structure of an exemplary peptide-coupling agent according to the present invention, 1-((dimethylimino)(morpholino)methyl)3-H-benzo[1,2,3] triazolo-1-ium-3-olate Hexafluorophosphate (HDMB), showing that the coupling agent is in the N-form thereof, in which the benzotriazole moiety is attached to the iminium moiety directly via one of the triazole nitrogen atoms and not via an oxygen atom; and FIG. 2 presents the HPLC chromatogram obtained for the penta-peptide Tyr-Gly-Gly-Phe-Leu.$NH_2$ prepared using an exemplary peptide-coupling agent according to the present embodiments, HDMB, showing that excellent product purity of the final product was obtained.

DESCRIPTION OF THE PREFERRED EMBODIMENTS

The present invention, in some embodiments thereof, is of novel iminium-type coupling agents containing proton acceptors in the carbocation moiety, which can be beneficially used as coupling agents in various chemical syntheses and are particularly useful as coupling agents for use in peptide and oligonucleotide syntheses. The present invention, in some embodiments thereof, is further of a process of preparing such coupling agents and of peptides and oligonucleotides prepared by utilizing same.

The principles and operation of the present invention may be better understood with reference to the figures and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As discussed in detail hereinabove, peptide-coupling agents are the most effective tools in the hands of the pharmaceutical peptide industry. Modern peptide-coupling agents are based on their ability to form a transient activate carboxyl entity at the carboxyl end of the emerging peptide while avoiding its racemization due to the effect of the leaving group part thereof. While the research in the field of coupling agent development in the recent years have focused on work towards the identification of the best leaving groups, less attention has been paid to the nature of the carbocation/iminium moiety.

As further discussed hereinabove, coupling agents which are used for peptide synthesis are typically also effective as coupling agents in oligonucleotide syntheses. Presently known oligonucleotide coupling reagents, such as 1,1-dioxide-3H-1,2-benzodithio-3-one (Beaucage reagent), 2-cyanoethyltetraisopropyl phosphorodiamidite (CAS No. 102691-36-1), 4,5-dicyanoimidazole (DCI), 4,4'-dimethoxytrityl chloride (DMT-Cl), di-tert-butyl N,N-diethylphosphoramidite (CAS No. 117924-33-1), di-tert-butyl N,N-diisopropylphosphoramidite CAS No. 137348-86-8), 4-methoxytrityl chloride CAS No. 14470-28-1) and phenylacetyl disulfide (PADS), are used typically to activate the end phosphate group of one nucleotide so as to react with a sugar moiety of another nucleotide. Thus, similar to the activation of a carboxyl group in peptide synthesis, the phosphate can be activated using the same type of peptide coupling agents.

While searching for more effective coupling agents, the present inventors have surprisingly found that incorporating proton acceptor groups to the iminium/carbocation moiety of uronium-type coupling agents leads to a much improved performance of said reagents, both in terms of coupling efficiency and of racemization suppression. The added proton acceptor group appears to facilitate the activation of the carboxyl intermediate at lower transition energies, substantially lowering the rate of amino-acid racemization while enhancing coupling reaction kinetics.

Without being bound by any particular theory, it is assumed that the presence of a basic point (the proton acceptor) in the iminium/carbocation moiety may assist in both the deprotonation of the carboxylic acid and the neutralization of the conjugated acid of the leaving group, increasing coupling yields and reducing racemization when compared with currently available coupling reagents. Furthermore, it is assumed that the proton acceptor may contribute to increasing the solubility of the coupling agent in common solvents used in peptide chemistry when compared with currently available coupling reagents.

As discussed hereinabove, peptide coupling agents are at large also effective in the coupling of nucleotides as well as derivatives and analogues thereof. It is thus noted herein that in the context of the present invention, any reference to the coupling capacity of peptide coupling agents also encompasses their capacity to activate phosphate groups in the coupling of nucleotides, as well as derivatives and analogues thereof.

Hence, according to one aspect of the present invention, there is provided a coupling agent having a general formula selected from the group consisting of:

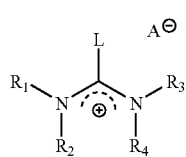

Formula I

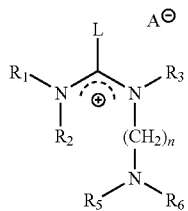

Formula II wherein:
A is an inorganic anion;
L is a leaving group;
n is an integer from 1 to 4,
each of $R_1$, $R_2$, $R_3$, $R_4$, $R_5$ and $R_6$ is independently selected from the group consisting of an alkyl having 1-4 carbon atoms and an alkyl having 1-4 carbon atoms interrupted, substituted and/or terminated by at least one heteroatom, or, alternatively, $R_1$ and $R_2$, and/or $R_3$ and $R_4$, and/or $R_5$ and $R_6$ are each independently joined to form a heteroalicyclic moiety,
whereas:
at least one of $R_1$, $R_2$, $R_3$, $R_4$, $R_5$ and $R_6$ is an alkyl having 1-4 carbon atoms interrupted, terminated and/substituted by at least one heteroatom and/or at least one of $R_1$ and $R_2$, and/or $R_3$ and $R_4$, and/or $R_5$ and $R_6$ are joined to form a heteroalicyclic moiety.

The term "heteroatom", as used herein, refers to a non-carbon and non-hydrogen atom, which can act as a proton acceptor. A heteroatom can therefore be, for a non-limiting example, nitrogen (N), oxygen (O), sulfur (S), phosphorus (P), boron (B) and selenium (Se). For example, the heteroatom is O, S, N, P or B, and alternatively, the heteroatom is O, S or N.

The phrase "proton acceptor", as used herein, refers to a heteroatom which can be protonated at a pH range which is common to coupling reactions, and change its form, from -Ä- to the form -AH$^+$—, wherein -Ä- is the heteroatom before being protonated and -AH$^+$— is its protonated form. In general, a proton accepting heteroatom possesses at least one lone pair of valence electrons, which can attract a proton (H$^+$) and hence are known as a proton acceptor.

The phrase "an alkyl interrupted, substituted and/or terminated by at least one heteroatom", as used herein, describes an alkyl, as defined herein, which contains a heteroatom in one or more positions within the alkyl hydrocarbon chain, at the end of the alkyl hydrocarbon chain and/or as a substituent of one of the carbon atoms in the alkyl. Examples of an alkyl interrupted by heteroatom(s) include, without limitation, ethers such as methoxymethyl, thioethers such as 3-thiobutane, amines such as diethylamine and phosphines such as triethylphosphine; examples of an alkyl substituted by the heteroatom(s) include, without limitation, alcohols (alkyls substituted with a hydroxyl group) such as isopropanol, amines such as 2-aminobutane, and thiols (alkyls substituted with a thiohydroxyl group) such as butane-3-thiol; an alkyl terminated by heteroatoms is a particular case in which the alkyl hydrocarbon backbone is substituted by a heteroatom at a terminal carbon.

According to some embodiments, in at least one of the pairs of N-substituents, i.e., the pair of $R_1$ and $R_2$, the pair $R_3$ and $R_4$, and the pair $R_5$ and $R_6$, the substituents are joined to form a heteroalicyclic moiety. Hence, the nitrogen atom of the doubly-substituted amine and the substituents attached thereto form a heteroalicyclic ring containing at least two heteroatoms.

The heteroalicyclic moiety therefore contains at least the nitrogen atom bearing the $R_1$ and $R_2$, and/or $R_3$ and $R_4$, and/or $R_5$ and $R_6$ substituents and further contains another heteroatom, as defined herein. Exemplary heteroatoms include, but are not limited to, oxygen, sulfur or nitrogen.

Examples of heteroalicyclic moieties include, without limitation, morpholines, thiomorpholines, oxazolidines, imidazolidines, 1,4-azaphosphinane (e.g. 4-methyl-1,4-azaphosphinane), azaphospholidines, azaborinanes (e.g. 4-methyl-1,4-azaborinane), azaborolidines (e.g. 2-methyl-1,2-azaborolidine) and piperazines (e.g., 4-methylpiperazine). For example, $R_1$ and $R_2$ can each be ethyl, joined together via an oxygen atom to form, together with the nitrogen they are attached to, a morpholine moiety, as illustrated in Scheme 2 below.

Scheme 2

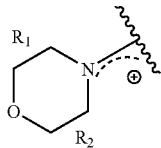

In cases where such $R_1$ and $R_2$ are joined together via a sulfur atom, a thiomorpholine moiety is formed. In cases where such $R_1$ and $R_2$ are joined together via a nitrogen atom, a piperazine moiety is formed.

Similarly, when $R_1$ is an ethyl and $R_2$ is a methyl joined together via a nitrogen atom, an imidazolidine is formed together with the nitrogen they are attached to. When $R_1$ is B-methylboroethane and $R_2$ is ethyl joined together via a boron atom, a 4-methyl-1,4-azaborinane is formed together with the nitrogen they are attached to, and so forth.

These embodiments can be applied also to $R_3$ and $R_4$, and $R_5$ and $R_6$.

As used herein, the phrase "moiety" describes a part of a chemical entity or compound, which typically has certain functionality or distinguishing features.

As used herein, the term "amine" describes a —NR'R" group where each of R' and R" is independently hydrogen, alkyl, cycloalkyl, heteroalicyclic, aryl or heteroaryl, as these terms are defined herein.

As used herein, the term "alkyl" describes an aliphatic hydrocarbon including straight chain and branched chain groups. For example, the alkyl group has 1 to 20 carbon atoms or 1-10 carbon atoms. Whenever a numerical range; e.g., "1-10", is stated herein, it implies that the group, in this case the alkyl group, may contain 1 carbon atom, 2 carbon atoms, 3 carbon atoms, etc., up to and including 10 carbon atoms. The alkyl can be substituted or unsubstituted. When substituted, the substituent can be, for example, an alkyl, an alkenyl, an alkynyl, a cycloalkyl, an aryl, a heteroaryl, a halide, a hydroxy, an alkoxy and a hydroxyalkyl as these terms are defined hereinbelow. The term "alkyl", as used herein, also encompasses saturated or unsaturated hydrocarbon, hence this term further encompasses alkenyl and alkynyl.

The term "alkenyl" describes an unsaturated alkyl, as defined herein, having at least two carbon atoms and at least one carbon-carbon double bond. The alkenyl may be substituted or unsubstituted by one or more substituents, as described hereinabove.

The term "alkynyl", as defined herein, is an unsaturated alkyl having at least two carbon atoms and at least one carbon-carbon triple bond. The alkynyl may be substituted or unsubstituted by one or more substituents, as described hereinabove.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted by one or more substituents, as described hereinabove.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted by one or more substituents, as described hereinabove. Representative examples are thiadiazole, pyridine, pyrrole, oxazole, indole, purine and the like.

The term "heteroalicyclic", as used herein, describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Substituted heteroalicyclic may have one or more substituents, whereby each substituent group can independently be, for example, alkyl cycloalkyl, alkenyl, alkynyl, aryl, heteroaryl and heteroalicyclic. Representative examples are morpholine, piperidine, piperazine, tetrahydrofurane, tetrahydropyrane and the like.

As used herein, the term "phosphine" describes a —PR'R"R'" group where each of R', R" and R'" is independently hydrogen, alkyl, cycloalkyl, heteroalicyclic, aryl or heteroaryl, as these terms are defined herein.

The terms "hydroxyl" and "thiohydroxyl" refer to a —OH and —SH groups respectively.

Exemplary inorganic anions include, without limitation, halide, hexahalophosphate, hexahaloantimonate, tetrahaloborate, trihalomethanesulfonate and bis(trihalomethylsulfonyl)imide.

The term "halide", as used herein, refers to the anion of a halo atom, i.e. $F^-$, $Cl^-$, $Br^-$ and $I^-$.

The term "halo" refers to F, Cl, Br and I atoms.

The term "hexahalophosphate" refers to the inorganic anion $PX_6^-$, wherein X is halo. An exemplary hexahalophosphate is hexafluorophosphate or $PF_6^-$, which is an exemplary inorganic anion according to the present embodiments.

The term "hexahaloantimonate" refers to the inorganic anion $SbX_6^-$, wherein X is halo.

The term "tetrahaloborate" refers to the inorganic anion $BX_4^-$, wherein X is halo.

The term "trihalomethanesulfonate" refers to the inorganic anion $CX_3SO_3^-$, wherein X is halo.

The term "bis(trihalomethylsulfonyl)imide" refers to the inorganic anion $N(SO_2CX_3)_2^-$, wherein X is halo.

As discussed herein, the type and characteristics of the leaving group, denoted L in formulae I and II, plays an important role in the effectiveness of the compound as a coupling agent, as well as in its safety.

As used herein, the phrase "leaving group" describes a labile atom, group or chemical moiety that readily undergoes detachment from an organic molecule during a chemical reaction, while the detachment is facilitated by the relative stability of the leaving atom, group or moiety thereupon. Typically, any group that is the conjugate base of a strong acid can act as a leaving group. Representative examples of suitable leaving groups according to the present embodiments therefore include, without limitation, halide, acetate, tosylate, triflate, sulfonate, azide, hydroxy, thiohydroxy, alkoxy, cyanate, thiocyanate, nitro and cyano.

The term "acetate" refers to acetic acid anion.

The term "tosylate" refers to toluene-4-sulfonic acid anion.

The term "triflate" refers to trifluoro-methanesulfonic acid anion.

The term "sulfonate" refers to a sulfonic acid anion.

The term "azide" refers to an $N_3^-$.

The terms "hydroxy" and "thiohydroxy" refer to the $OH^-$ and $SH^-$ anions respectively.

The term "alkoxy" refers to an $R'\!-\!O^-$ anion, wherein R' is as defined hereinabove.

The term "cyanate" and "thiocyanate" refer to $[O\!=\!C\!=\!N]^-$ and $[S\!=\!C\!=\!N]^-$ anions respectively.

The term "nitro" refers to $NO_2^-$.

The term "cyano" refers to $[C\!\equiv\!N]^-$.

According to some embodiments, the leaving group is selected from the group consisting of a benzotriazole, a benzotriazinone, a succinimide, a ketoxime, a pyridin-2(1H)-one-1-oxy, a quinazolin-4(3H)-one-3-oxy, a 1H-benzo[d]imidazol-1-oxy, an imidazole, an indolinone-1-oxy, pentafluorophenol, pentafluorothiophenol, 2-nitrophenol and 2-nitrobenzenethiol.

According to some embodiments, a benzotriazole has the general Formula III:

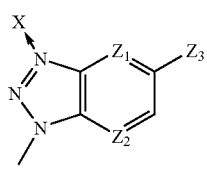

Formula III wherein:

X is O or S;

$Z_1$ and $Z_2$ are each independently CH or N; and $Z_3$ is F, Cl, Br, $CF_3$ or $NO_2$.

An exemplary benzotriazole is one wherein X is O or S; $Z_1$ and $Z_2$ are each CH; and $Z_3$ is Cl, resulting in a leaving group having the following formula:

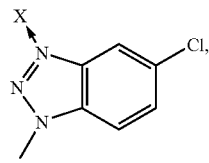

in which X is O, and the leaving group is:

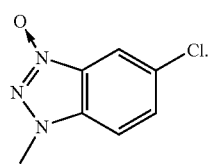

Another exemplary benzotriazole is one wherein X is O or S; $Z_1$ and $Z_2$ are each CH; and $Z_3$ is $CF_3$ or $NO_2$. For example X is O; and $Z_3$ is $CF_3$ or $NO_2$, and alternatively $Z_3$ is $CF_3$, resulting in a leaving group:

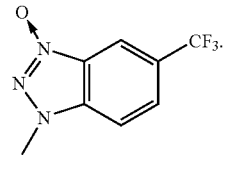

According to other embodiments, a benzotriazinone has the general Formula IV:

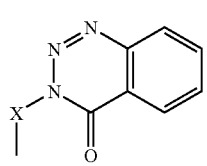

Formula IV wherein X is O or S, or X is O.

The present inventors have also considered the need for a coupling agent which will be as safe for use as it is effective. It has been recognized that substances containing a triaza moiety are potentially exposive. Recent reports [Wehourstedt et al., *J. Hazard. Mat.* A126 (2005) 1] have confirmed that HOBt derivatives exhibit explosive properties under certain conditions, presumably due to the explosive properties of 1-hydroxy-benzotriazole and of benzotriazole derivatives in general. Similarly, coupling agents based on other triaza-containing groups (e.g., triazine, triazole) have been associated with explosiveness.

To this effect, the present inventors have developed several series of coupling agents which are based on less hazardous leaving groups, such as succinimide-, ketoxime-, pyridine-, quinazoline-, imidazole- and indolinone-based leaving groups. These coupling agents are highly advantageous by being safe in terms of their preparation, storage, transportation and use.

Hence, according to some embodiments, a succinimide-type leaving group has the general Formula V:

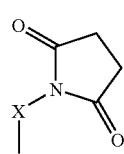

Formula V wherein X is O or S, or X is O.

According to still further features in some embodiments, the ketoxime has the general Formula VI:

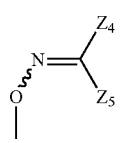

Formula VI wherein:

$Z_4$ and $Z_5$ can each independently be any one of F, Cl, Br, CORa, COORa, CONRa, CN, $CF_3$ or $NO_2$; with Ra being hydrogen or alkyl.

For example, $Z_4$ is COORa; Ra is ethyl; and $Z_5$ is CN, resulting in the leaving group:

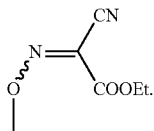

Alternatively, $Z_4$ and $Z_5$ are both COORa with Ra being ethyl, resulting in the leaving group:

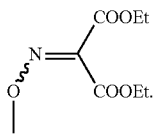

Alternatively, $Z_4$ and $Z_5$ are both CN, resulting in the leaving group:

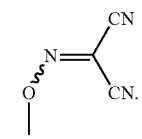

According to still further features in some embodiments, the pyridine-2(1H)-one-1-oxy has the general Formula VII:

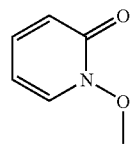

Formula VII

According to still further features in some embodiments, the quinazolin-4(3H)-one-3-oxy has the general Formula VIII:

Formula VIII

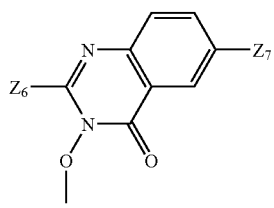

wherein:

$Z_6$ and $Z_7$ can each independently be any one of H, F, Cl, Br, CN, $CF_3$, $NO_2$, aryl or alkyl.

For example, $Z_6$ is $CH_3$; and $Z_7$ is Cl.

According to some embodiments, the -benzo[d]imidazol-1-oxy has the general Formula IX:

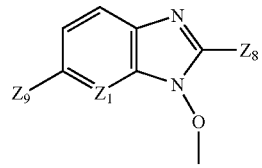

Formula IX wherein:

$Z_8$ and $Z_9$ can each independently be any one of H, F, Cl, Br, CN, $CF_3$, $NO_2$, aryl or alkyl.

For example, $Z_1$ is CH, $Z_8$ is phenyl; and $Z_9$ is Cl.

Alternatively, $Z_1$ is N, $Z_8$ is methyl; and $Z_9$ is H.

According to some embodiments, the indolinone-1-oxy has the general Formula X:

Formula X

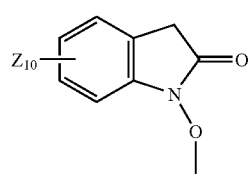

wherein:

$Z_{10}$ can be any one of H, F, Cl, Br, CN, $CF_3$, $NO_2$, aryl or alkyl.

According to another aspect of the present invention there is provided a process of preparing the coupling agents presented herein, the process is effected by:

contacting a compound, which is also referred to herein a urea derivative, having the general formula selected from the group consisting of:

Formula XI

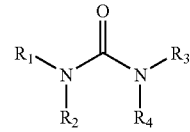

Formula XII

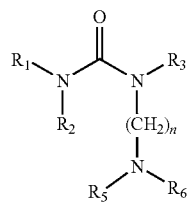

wherein:

each of $R_1$, $R_2$, $R_3$, $R_4$, $R_5$ and $R_6$ is independently selected from the group consisting of an alkyl having 1-4 carbon atoms and an alkyl having 1-4 carbon atoms interrupted, substituted and/or terminated by at least one heteroatom, or, alternatively, $R_1$ and $R_2$, and/or $R_3$ and $R_4$, and/or $R_5$ and $R_6$ are each independently joined to form a heteroalicyclic moiety, and wherein:

at least one of $R_1$, $R_2$, $R_3$, $R_4$, $R_5$ and $R_6$ is an alkyl having 1-4 carbon atoms interrupted, substituted and/or terminated by at least one heteroatom and/or at least one of $R_1$ and $R_2$, and/or $R_3$ and $R_4$, and/or $R_5$ and $R_6$ are joined to form a heteroalicyclic moiety;

with: (i) halogenating agent; and (ii) saturated aqueous solution of an inorganic anion as presented hereinabove, to thereby obtain the coupling agent presented herein wherein L is halo.

The first step (i) uses a halogenating agent, which is capable of halogenating the urea derivative and replace the carbonyl with a halo.

The phrase "halogenating agent", as used in this context of the present embodiments, therefore refers to a reagent which is used to introduce a halo substituent in place of a carbonyl.

Exemplary halogenating agents include an oxalyl halide, a phosgene such as $COCl_2$, a thionyl halide ($SOX_2$) such as thionyl chloride and phosphorus oxyhalide ($POX_3$) such as phosphorus oxychloride ($POCl_3$). An exemplary halogenating agent, according to the present embodiments, is oxalyl halide.

The phrase "oxalyl halide", as used herein, refers to the halogenating agent $(COX)_2$ or $X(C=O)(C=O)X$, wherein X is halo. For example, the oxalyl halide used is oxalyl chloride. Thionyl halide ($X_2S=O$, wherein X is halo), such as thionyl chloride can also be used to effect the same conversion.

The second step (ii) using a saturated aqueous solution containing the selected inorganic anion affords a coupling agent in the form of a salt having the iminium/carbonium cation and the inorganic anion of choice, wherein the leaving group is the halo stemming from the oxalyl halide.

As used herein, the term "iminium" describes a $=N^+R'R''$ group where R' and R'' are as defined herein.

The phrase "iminium/carbonium cation" as used herein describes a $-\{C(NR'R'')(NR'''R'''')\}^+$ group, where R', R'' and R''' are as defined herein, and R'''' as defined for R'.

It should be noted that the order of performing steps (i) and (ii) can be reversed or, optionally, steps (i) and (ii) can be performed simultaneously.

The urea derivative, having either the general Formula XI or XII, is afforded by reacting a compound having the general Formula XIII:

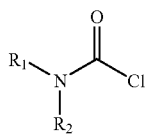

Formula XIII wherein each of $R_1$ and $R_2$ is independently selected from the group consisting of an alkyl having 1-4 carbon atoms and an alkyl having 1-4 carbon atoms interrupted, substituted and/or terminated by at least one heteroatom, or $R_1$ and $R_2$ are joined to form a heteroalicyclic moiety;

with a compound having the general Formula XIV:

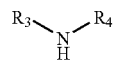

Formula XIV wherein each of $R_3$ and $R_4$ is independently selected from the group consisting of an alkyl having 1-4 carbon atoms and an alkyl having 1-4 carbon atoms interrupted, substituted and/or terminated by at least one heteroatom, or $R_3$ and $R_4$ are joined to form a heteroalicyclic moiety;

in the presence of a base, to thereby obtain the compound having the general Formula XI;

or with a compound having the general Formula XV:

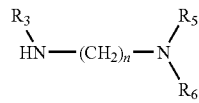

Formula XV wherein each of $R_3$, $R_5$ and $R_6$ is independently selected from the group consisting of an alkyl having 1-4 carbon atoms and an alkyl having 1-4 carbon atoms interrupted, substituted and/or terminated by at least one heteroatom, or $R_5$ and $R_6$ are joined to form a heteroalicyclic moiety; and n is an integer from 1 to 4;

in the presence of a base, to thereby obtain the compound having the general Formula XII.

The base can be an organic base, such as triethylamine, or an inorganic base such as NaOH.

Once the basic coupling agent, having a halo for a leaving group is prepared, the leaving group can be replaced with a variety of leaving groups and presented hereinabove. This step is effected by reacting the basic coupling agent wherein L is halo with a precursor compound of the leaving group of choice in the presence of a base such as, for example, triethylamine.

The phrase "precursor compound of the leaving group", as used herein, refers to a compound, typically an acid, which is the conjugated acid of the leaving group. For example, acetic acid is the precursor compound of the leaving group acetate, toluene-4-sulfonic acid is the precursor compound of the leaving group tosylate, trifluoro-methanesulfonic acid is the precursor compound of the leaving group triflate and so on.

For other examples, in cases where the selected leaving group is benzo[1,2,3]triazolo-1-ium-3-olate, the precursor compound of this leaving group is 1-hydroxybenzotriazole, also known as HOBt.

In cases where the selected leaving group is 6-chloro-benzo[1,2,3]triazolo-1-ium-3-olate, the precursor compound of this leaving group is 6-Cl-HOBt.

In cases where the selected leaving group is [1,2,3]triazolo[4,5-b]pyridine-1-3-olate, the precursor compound of this leaving group is 1-hydroxy-7-azabenzotriazole.

In cases where the selected leaving group is [1,2,3]triazolo[2,3-b]pyridine-1-ium-3-olate, the precursor compound of this leaving group is 4-HOAt.

In cases where the selected leaving group is pyrrolidine-2,5-dione, the precursor compound of this leaving group is 1-hydroxypyrrolidine-2,5-dione. Similarly pentafluorophenol is the precursor compound for the leaving group oxypentafluorophenyl.

In cases where the selected leaving group is 2-(oxyiminoate)malononitrile, the precursor compound of this leaving group is 2-(hydroxyiminoate)malononitrile, also referred to herein as KONDC.

In cases where the selected leaving group is pyridin-2(1H)-one-1-oxy, the precursor compound of this leaving group is N-hydroxypyridin-2(1H)-one.

In cases where the selected leaving group is 3-oxy-2-methylquinazolin-4(3H)-one, the precursor compound of this leaving group is 3-hydroxy-2-methylquinazolin-4(3H)-one, also referred to herein as HOMQ.

In cases where the selected leaving group is 6-chloro-2-phenyl-1H-benzo[d]imidazol-1-oxy, the precursor compound of this leaving group is 6-chloro-2-phenyl-1H-benzo[d]imidazol-1-ol, also referred to herein as 6-Cl-HOPBI.

In cases where the selected leaving group is 2-methyl-3H-imidazo[4,5-b]pyridin-3-oxy, the precursor compound of this leaving group is 2-methyl-3H-imidazo[4,5-b]pyridin-3-ol, also referred to herein as HOMPI, and so forth.

As demonstrated in the Examples section that follows, coupling agents which are based on an iminuim/carbonium moiety that is substituted with heteroalicyclic moieties as presented herein have been prepared and used successfully in peptide syntheses.

Exemplary coupling agents according to some embodiments of the invention are listed in Table 1 below.

TABLE 1

| Name and abbreviation of the coupling agent | Chemical structure of the coupling agent |
| --- | --- |
| 4-((dimethyamino)chloromethylene)morpholin-4-iminium hexaflurophosphate (DCMH) | |
| 4-((dimethylamino)fluoromethylene)morpholin-4-iminium hexafluorophosphate (DFMH) | |
| 4-(chloro(morpholino)methylene)morpholin-4-iminium Hexafluorophosphate (CMMH) | |
| 4-(Fluoro(morpholino)methylene)morpholin-4-iminium hexafluorophosphate (FMMH) | |
| 1-((dimethylimino)(morpholino)methyl)3-H-benzo[1,2,3]triazolo-1-ium-3-olate Hexafluorophosphate (HDMB) | |
| 1-((dimethylimino)(morpholino)methyl)3-H-6-chlorobenzo[1,2,3]triazolo-1-ium-3-olate hexafluorophosphate (6-Cl-HDMB or 6-HMDCB) | |
| 1-((dimethylimino)(morpholino)methyl)3-H-[1,2,3]triazolo[4,5-b]pyridine-1-3-olate hexafluorophosphate (HDMA) | |

TABLE 1-continued

| Name and abbreviation of the coupling agent | Chemical structure of the coupling agent |
|---|---|
| 1-((dimethylimino)(morpholino)methyl)3-H-[1,2,3]triazolo[2,3-b]pyridine-1-ium-3-olate hexafluorophosphate (4-HDMA) | |
| 1-((dimethylimino)(morpholino)methyl)3-H-6-trifluoromethylbenzo[1,2,3]triazolo-1-ium-3-olate hexafluorophosphate (6-$CF_3$HDMB or 6-HDMFB) | |
| 1-((dimethyamino)(morpholino))pyrrolidine-2,5-dione metheniminium hexafluorophosphate (HDMS) | |
| 1-((dimethyamino)(morpholino))oxypentafluorophenyl metheniminium hexafluoro phosphate (HDMPfp) | |
| 1((dimethylimino)(thiomorpholino)methyl)3-H-[1,2,3]triazolo[4,5-b]pyridine-1-3-olate hexafluorophosphate (HDTMA) | |
| 1((dimethylimino)(thiomorpholino)methyl)3-H-benzo[1,2,3]triazolo-1-ium-3-olate Hexafluorophosphate (HDTMB) | |

TABLE 1-continued

| Name and abbreviation of the coupling agent | Chemical structure of the coupling agent |
|---|---|
| 1-(N-methyl-N-morpholinomethylene)-(2-oxopyridin-1(2H)-yloxyl)methanaminium Hexafluorophosphate (HDMOP) | |
| 1-[(1-(Cyano-2-ethoxy-2-oxoethylideneaminooxy)-dimethylamino-morpholinomethylene)] methanaminium hexafluorophosphate (HDMOCC) | |
| 1-[(1-(cyano-2-ethoxy-2-oxoethylideneaminooxy)-dimethylamino-morpholinomethylene)] methanaminium Hexafluorophosphate (HDMOCC) | |
| 1-[(1-(dicyanomethyleneaminooxy)-dimethylamino-morpholinomethylene)] methanaminium Hexafluorophosphate (HDMODC) | |
| 1-[(1,3-diethyoxy-1,3-dioxopropan-2-ylideneaminooxy)-dimethylamino-morpholinomethylene)] methanaminium Hexafluoorphosphate (HDMODeC) | |
| N-[(cyano(pyridine-2-yl)methyleneaminooxy)(dimethylamino)methylene)-N-morpholinomethanaminium Hexafluorophosphate (HDMOPC) | |

TABLE 1-continued

| Name and abbreviation of the coupling agent | Chemical structure of the coupling agent |
|---|---|
| 6-Chloro-1-((dimethylamino)(pyrrolidinium-1-ylidene)methyl)-1H benzo[d][1,2,3]triazole 3-oxide hexafluorophospahte (6-Cl-HDmPyB) | 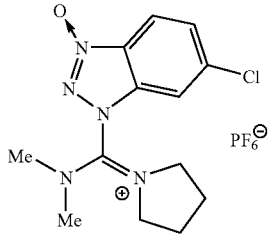 |
| 1-((Dimethylamino)(2-oxopyridin-1(2H)-yloxy)methylene)pyrrolidinium hexafluorophosphate (HDmPyOP) | 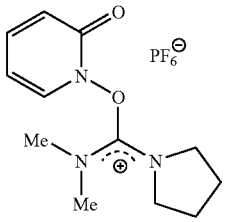 |
| 1-[(1-(Cyano-2-ethoxy-2-oxoethylideneaminooxy)-dimethylamino-pyrrolodinomethylene)] methanaminium hexafluorophosphate (HDmPyOCC) | 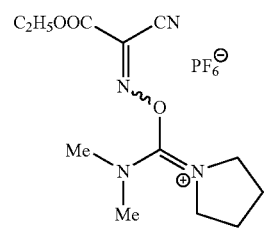 |
| 1-[(1-(dicyanomethylideneaminooxy)-dimethylamino-pyrrolodinomethylene)] methanaminium hexafluorophosphate (HDmPyODC) | 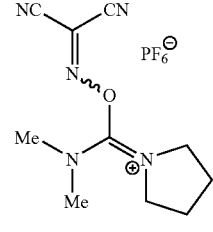 |
| 1-[(1,3-diethyoxy-1,3-dioxopropan-2-ylideneaminooxy)-dimethylamino-pyrrolodinomethylene)] methanaminium hexafluorophosphate | 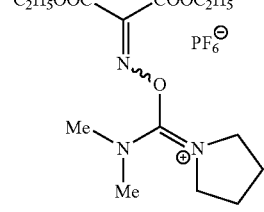 |
| 1-((dicyanomethyleneaminooxy)(morpholino)methylene)pyrrolidinium hexafluorophosphoate (HMPyODC) | 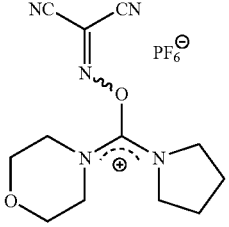 |

TABLE 1-continued

| Name and abbreviation of the coupling agent | Chemical structure of the coupling agent |
|---|---|
| 1-((1-Cyano-2-ethoxy-2-oxoethylideneaminooxy)(morpholino)methylene)pyrrolidinium hexafluorophosphate (HMPyOCC) | 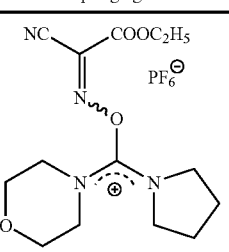 |
| 1-[(1,3-diethyoxy-1,3-dioxopropan-2-ylideneaminooxy)-(morpholino)methylene)pyrrolidinium hexafluorophosphoate | 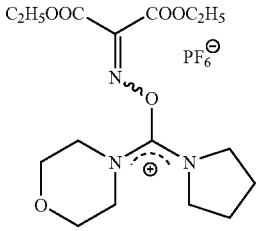 |
| 1-(morpholino(pyrrolidinium-1-ylidene)methyl)-1H-benzo[d][1,2,3]triazole 3-oxide hexafluorophosphate (HMPyB) | 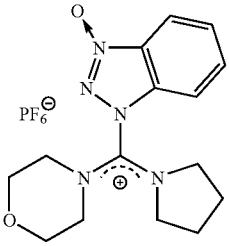 [SMILES: "PF6" ; [O-][n+]1nn(C(N2CCCC2)N2CCOCC2)c2ccccc21] |
| 1-(morpholino(pyrrolidinium-1-ylidene)methyl)-1H-[1,2,3]triazolo[4,5-I]pyridine 3-oxide hexafluorophospahte (HMPyA) | 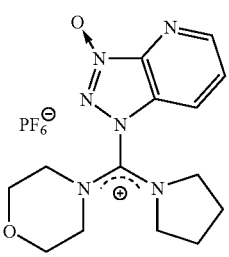 [SMILES: "PF6" ; [O-][n+]1nn(C(N2CCCC2)N2CCOCC2)c2cccnc21] |
| 5-chloro-1-(morpholino(pyrrolidinium-1-ylidene)methyl)-1H-benzo[d][1,2,3]triazole 3-oxide hexafluorophosphate (6-HMPyCB) | 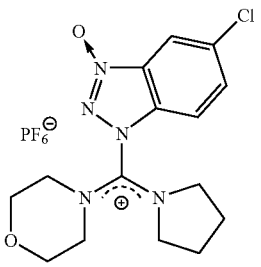 [SMILES: "PF6" ; [O-][n+]1nn(C(N2CCCC2)N2CCOCC2)c2ccc(Cl)cc21] |

As discussed hereinabove, coupling agents are ranked according to several criteria which are important in peptide synthesis and these are: yield of peptide-bond formation in general and the yield of peptide-bond formation between amino acids which present particular steric coupling hindrance, and the rate of racemization of the activated amino acid on which the coupling agent exerts its activity.

As used herein, the term "peptide" encompasses a biomolecule that comprises a plurality of amino acid residues, linked one to another via a peptide bond or a modification thereof. A peptide includes at least 2 amino acid residues and up to 200 amino acid residues and even more. This term, as used herein, encompasses also polypeptides, peptidomimetics, as well as peptoids and semipeptoids which are peptide analogs, which may have, for example, modifications rendering the peptides more stable while in a body or more capable of penetrating into cells.

As used herein throughout, the phrase "amino acid residue" describes a residue of an amino acid which forms a part of a peptide, namely, which is coupled to at least one another amino acid residue.

As is well accepted in the art, the term "residue", as used herein, refers to a portion, and typically a major portion of a molecular entity, such as molecule or a part of a molecule such as a group, which has underwent a chemical reaction and is now covalently linked to another molecular entity. For example, the molecular entity can be an amino acid molecule, and the portion of the amino acid which forms a part of a peptide chain after the formation of the peptide chain, is an amino acid residue. An amino acid residue is therefore that part of an amino acid which is present in a peptide sequence upon reaction of, for example, an alpha-amine group thereof with a carboxylic group of an adjacent amino acid in the peptide sequence, to form a peptide amide bond and/or of an alpha-carboxylic acid group thereof with an alpha-amine group of an adjacent amino acid in the peptide sequence, to form a peptide amide bond.

The term "side-chain", as used herein with reference to amino acids, refers to a chemical group which is attached to the α-carbon atom of an amino acid. The side-chain is unique for each type of amino acid and does not take part in forming the peptide bond which connects the amino acids in a polypeptide. For example, the side chain for glycine is hydrogen, for alanine it is methyl, for valine it is isopropyl and for methionine it is methylsulfanyl-ethyl. For the specific side chains of all amino acids reference is made to A. L. Lehninger's text on Biochemistry (see, chapter 4).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Abbreviations used herein for amino acids and the designations of peptides follow the rules of the IUPAC-IUB Commission of Biochemical Nomenclature in J. Biol. Chem. 1972, 247, 977-983.

Tables 2 and 3 below list naturally occurring amino acids (Table 2) and non-conventional, modified and unnatural amino acids (Table 3) which can be used in the context of the present invention.

TABLE 2

| Amino Acid | Three-Letter Abbreviation | One-letter Symbol |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophane | Trp | W |
| Tyrosine | Tyr | Y |
| Valine | Val | V |
| Any amino acid as above | Xaa | X |

TABLE 3

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |

TABLE 3-continued

| Non-conventional amino acid | Code | Non-conventional amino acid | Code |
|---|---|---|---|
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylaspartate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine | Mval Nnbhm | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino)cyclopropane | Nmbc | phenylglycine | Phg |
| Aminocyclopropane-Carboxylate | Cpro | Aminonorbornyl-Carboxylate | Norb |

The yield of peptide-bond formation can be determined simply by measuring the amount of product (for example an elongated peptide) versus the amount of starting material and/or side-reaction impurities. In cases of coupling of particular sterically-hindered amino acids, such as phenylglycine, or otherwise more difficult-to-couple amino acids such as 2-aminoisobutyric acid, the length and sequence of the resulting peptide will serve as an indication of coupling yield.

During the process of peptide-bond formation which is mediated by a coupling agent, the carboxylic part of the amino acid interacts with the coupling agent to form an activated intermediate, which in turn interacts with the amino part of the next amino acid. During this process a full inversion of the stereo-configuration of the activated amino acid may occur, and more likely a partial inversion may occur which leads to racemization of the chiral center of that particular amino acid.

The rate of racemization, which is one of the most prevailing technological problems in peptide synthesis, is also the most difficult to measure. The term "racemization", as used herein, refers to partial conversion of one enantiomer of a chiral molecule into its other stereoisomeric form, or its "mirror image" inversion.

As used herein, the term "enantiomer" refers to a stereoisomer of a compound, such as an amino acid, that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems.

As demonstrated in the Example section that follows, the coupling agents presented herein were tested in some of the most challenging peptide synthesis tasks, and were rated according to their peptide-bond formation yield and rate of racemization.

Hence, according to another aspect of the present invention, there is provided a method of synthesizing a peptide, the method is effected by sequentially coupling a plurality of amino acids, one with another, in the presence of the coupling agent presented herein, to thereby obtain a peptide containing a plurality of amino acids.

The quality of a coupling agent is therefore measured according to the quality of the resulting peptide, namely the efficiency of its production (the yield of the reaction) and the rate of internal racemization of each of the chiral centers therein (the purity of the product). This assessment of quality can be quantified as a stepwise indicator, per each elongation step, or as an overall rate per the complete peptide. Obviously when trying to compare coupling agents it is best to avoid criteria in which the peptide sequence plays a key role in the efficiency of its synthesis, and therefore a stepwise criteria, looking at particular amino-acid pairs, will serve as an indicative coupling agent quality ranking criteria.

According to some embodiments the yield of coupling per each general coupling step ranges from 80% to 99%, depending on the coupling agent and other conditions. In essence, a coupling agent having a proton acceptor substituent will be more efficient as compared to its presently known counterpart not having such substituent by at least 5%, or at least 10%.

Of particular importance is the effectiveness of the coupling agent presented herein when used in the syntheses of peptides that incorporate amino acid residues that are otherwise incorporated in relatively low yields and sometimes are particularly difficult to be incorporated.

Exemplary amino acids that are considered difficult to be incorporated in common peptide syntheses include, but are not limited to, amino acids having a secondary alpha amine, amino acids having a tertiary alpha amine, amino acids having a substituted alpha carbon atom and amino acids having an amino-containing side chain.

The incorporation of amino acids that have a secondary or tertiary alpha amine into a synthetically prepared peptide is exceptionally difficult to perform, due to the hindrance of the amine that participates in the coupling reaction.

The incorporation of amino acids having a substituted alpha carbon atom also substantially affects the synthesis yield due to the steric interactions induced by the substituent, which interfere with the coupling reaction. The incorporation of two consecutive such amino acids are even more complicated. As is well known in the art, amino acids that are substituted at the alpha carbon even by a low alkyl such as methyl are difficult to be incorporated in a peptide sequence.

The incorporation of amino acids that have an amino-containing side chain is oftentimes complicated by the unselective reaction of a coupling agent with the side chain amine group. Such an unselective reaction leads to termination of the peptide chain.

As mentioned above, the method, according to this aspect of the present invention, is therefore particularly useful for synthesizing peptides that include one or more residues of the amino acids cited above.

Thus, in some embodiments of the present invention, at least one of the pluralities of amino acids that are used for synthesizing the peptide is an amino acid having a secondary alpha amine, an amino acid having a tertiary alpha amine, an amino acid having a substituted alpha carbon atom and/or an amino acid having an amino-containing side chain. The peptides prepared by this method therefore include at least one residue of such amino acids.

According to some embodiments of the present invention, one or more of the plurality of amino acids in an amino acid having a substituted alpha carbon.

In one embodiment the alpha carbon is substituted by an alkyl such as methyl. An exemplary amino acid in this respect is α-amino-isobutyric acid (Aib).

In another embodiment, at least two such amino acids are sequentially incorporated in the peptide prepared by the method presented herein, such that the peptide comprises two such amino acids that are coupled one to another.

According to another embodiment of the present invention, a peptide containing two or more residues of such an amino acid, coupled one to another is obtained in a yield greater than 80%, greater than 85%, greater than 90%, greater than 95%, and even greater than 98%.

In an exemplary embodiment of this aspect of the present invention, one or more of the plurality of amino acids is an amino acid having a substituted alpha carbon which is chiral. As discussed hereinabove, coupling agent mediated peptide synthesis is prone to inversion of the stereo-configuration of the activated amino acid, and more likely a partial inversion may occur which leads to racemization of the chiral center of that particular amino acid, and eventually leads to formation of heterogeneous mixture of peptides when considering stereoisomers thereof. Any amino acid which exhibits a chiral center at the alpha-carbon is sensitive to the coupling reaction with respect to preservation of stereo-configuration. Examples of such amino acids include all D/L-amino acids except glycine, D/L-α-methyl-amino acids such as D-α-methylisoleucine and the likes. According to another embodiment of the present invention, a peptide containing one or more residues of such an amino acid is obtained in a yield greater than 80%, greater than 85%, greater than 90% and even greater than 95%.

As demonstrated in the Examples section that follows, the coupling agents presented herein are superior over presently known coupling agents with respect to the yield of the challenging stereo-hindered couplings reaction of α-aminoisobutyric acid (Aib), even in the coupling of two consecutive Aib residues. The exemplary coupling agents, 6-Cl-HDMB, HDMA and HDMB as presented herein exhibited from 98.7%, 98% and 89% yield per a particular Aib-Aib coupling step respectively, as compared to 83% yield measured for HATU and 47% measured for HBTU, two known coupling agents.

As further demonstrated in the Examples section that follows, the coupling agents presented herein are superior over presently known coupling agents with respect to the yield of the challenging couplings reaction of more than 10 amino acids in one sequence. As demonstrated in the Examples section, the coupling agents presented herein were used to form a peptide having a specific sequence of 15 amino acids, the peptide H-Glu-Lys-Ile-Thr-Thr-Val-Gln-Ala-Ala-Ile-Asp-Tyr-Ile-Asn-Gly-$NH_2$. According to this embodiment of the present invention, a peptide containing more than 10 residues is obtained in a yield greater than 40%, greater than 50% and even greater than 60%.

According to some embodiments, the rate of racemization per each coupling step is not higher than 10%, and can range from about 10% to about 0.5%, or from about 5% to about 0.1%.

As demonstrated in the Examples section that follows, the coupling agents presented herein are superior over presently known coupling agents with respect to the rate of racemization which occurred upon use of the coupling agents at the chiral center which the coupling agent activates for the coupling reaction. This criterion was estimated for phenylglycine (Phg) after coupling of a proline residue thereto; and for valine after coupling of a proline residue thereto.

In another embodiment of this aspect of the present invention, in each of the sequential attachments of the amino acids, the coupling agent is used in an amount that ranges from 0.2 mol equivalent to 5 mol equivalents relative to the molar amount of the amino acid, or from about 0.5 mol equivalent to 3 mol equivalents relative to the molar amount of the amino acid, or alternatively a stoichiometric amount of the coupling agent is used.

Using the above described method, which utilizes the high reactivity and selectivity of the coupling agent presented herein, peptides compositions which comprise a high concentration of the desired peptide, namely, a peptide having the desired sequence, can be obtained. Such compositions typically have a concentration of a desired peptide which is higher than that obtained using presently known coupling agents.

Thus, according to a further aspect of the present invention there is provided a crude composition of peptides, which is synthesized in a C-terminus to N-terminus direction, and which consists essentially of a peptide having a desired amino acid sequence and a plurality of peptides having undesired amino acid sequences, which are impurities of the peptide that has the desired amino acid sequence. According to this aspect of the present invention, the concentration of the peptide having the desired amino acid sequence in the composition is at least 5% above a concentration of an identical peptide having the desired amino acid sequence, in a composition of peptides being synthesized in a C-terminus to N-terminus direction using the coupling agents described herein, as compared to a composition otherwise prepared under the same conditions using presently known coupling agents.

As used herein, the phrase "a peptide having a desired sequence" describes a peptide that comprises a desired sequence in terms of the order and the composition of amino acids in the peptide chain and a desired chain length in terms of the number of amino acids in the peptide chain.

The phrase "a peptide having an undesired sequence" describes a peptide that comprises a different sequence, in terms of order and composition of the amino acids in the peptide chain and a different chain length in terms of the number of amino acids in the peptide chain, as compared with a peptide having a desired sequence.

The phrase "a crude composition of peptides" describes a crude product of a peptide synthesis (in which the peptides are prepared in a C-terminus to N-terminus direction). As is well known ion the art, such a crude product is consisted of a peptide having a desired sequence, as defined herein, which is contaminated by peptides having an undesired sequence, as defined herein. Depending on the synthetic method used for preparing the peptide and the conditions and procedures employed therewithin, such a crude composition can be in a form of a solid or a solution. Solid compositions can be, for example, powdered or lyophilized. The composition can further be bound to a solid support, onto which the peptide was synthesized. Solutions may include the composition solubilized or dissolved in, a liquid media. Such a liquid media is typically an aqueous media, which comprises, in addition to water, various salts, buffers and the like.

In some embodiments of this aspect of the present invention, the concentration of the peptide having the desired amino acid sequence in the composition is at least 5%, at least 8%, at least 10%, at least 12%, at least 15%, at least 18%, at least 20%, at least 22%, at least 25%, and even at least 30% above a concentration of an identical peptide having the desired amino acid sequence in a composition of peptides being synthesized in a C-terminus to N-terminus direction using presently known coupling agents otherwise prepared under the same conditions.

Exemplary crude compositions according to this aspect of the present invention are those in which the peptide having the desired amino acid sequence comprises at least one amino acid residue selected from the group consisting of a residue of an amino acid having a secondary alpha amine, a residue of an amino acid having a tertiary alpha amine, a residue of an amino acid having a substituted alpha carbon atom and a residue of an amino acid having an amino-containing side chain, as is defined and detailed hereinabove.

Other crude compositions according to this aspect of the present invention are those in which the peptide having the desired amino acid sequence comprises at least two coupled amino acid residues, whereby at least one of the at least two amino acid residues is selected from the group consisting of a residue of an amino acid having a secondary alpha amine and a residue of an amino acid having a tertiary alpha amine.

Other crude compositions according to this aspect of the present invention are those in which the peptide having the desired amino acid sequence comprises at least two coupled amino acid residues acids having a substituted alpha carbon atom (e.g., Aib residues).

Any of the presently known techniques for chemically synthesizing a peptide can be used in this context of the present embodiments. These include, for example, standard solid phase techniques including exclusive solid phase synthesis, partial solid phase synthesis methods, and fragment condensation, and classical solution synthesis. Solid phase peptide synthesis procedures are well known in the art and further described by John Morrow Stewart and Janis Dillaha Young, Solid Phase Peptide Syntheses (2nd Ed., Pierce Chemical Company, 1984).

The obtained peptides can be further purified, using, for example, preparative high performance liquid chromatography [Creighton T. (1983) Proteins, structures and molecular principles. WH Freeman and Co. N.Y.]. Other exemplary purification procedures may include hydroxyapatite, size exclusion and immobilized metal ion adsorption (IMAC) chromatography.

Suitable chromatographic media include derivatized dextrans, agarose, cellulose, polyacrylamide, specialty silicas, and the like. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like.

Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of peptides by amino groups, carboxyl groups, sulfhydryl groups, hydroxyl groups and/or carbohydrate moieties. These and other solid media are well known and widely used in the art, and are available from commercial suppliers. Selection of a particular method is determined by the properties of the chosen support. See, for example, Affinity Chromatography: Principles & Methods, Pharmacia LKB Biotechnology, Uppsala, Sweden, 1988.

The peptides prepared by the method according to this aspect of the present invention are linear, although cyclic forms of the peptide can also be obtained.

Cyclic peptides can either be synthesized in a cyclic form or configured so as to assume a cyclic form under desired conditions (e.g., physiological conditions).

As discussed hereinabove, the coupling agents presented herein can also be used in the synthesis of various nucleic acids, oligonucleotides, polynucleotides, analogues and derivatives thereof. The coupling agents activate the phosphate group of nucleotides in a similar way they activate the carboxyl group of amino acids, thereby effecting the coupling of one nucleotide to another.

Thus, according to another aspect of the present invention, there is provided a method of synthesizing a polynucleotide or oligonucleotide, the method is effected by either a solid phase technique or a solution phase technique, and by sequentially coupling a plurality of nucleotides, one with another, in the presence of the coupling agent presented herein, to thereby obtain a polynucleotide containing a plurality of nucleotides.

As used interchangeably herein, the terms "polynucleotides", "oligonucleotides" and "nucleic acids", are collectively referred to as "polynucleotides", and include, for example, RNA, DNA, or RNA/DNA hybrid sequences of more than one nucleotide in either single chain or duplex form. However, in the context of the present embodiments, since the chemical synthesis of an oligonucleotide typically involves single stranded species, the oligonucleotide is essentially a single stranded species at least in the part which is being chemically synthesized using a coupling agent. Hence, nucleotides are monomeric units of a polynucleotide or nucleic acids such as DNA and RNA.

As used herein, the term "nucleotide" refers to molecule which comprises a nucleobase-sugar-phosphate combination, meaning a molecule, or an individual unit in a larger nucleic acid molecule, comprising a purine, a pyrimidine or an analogue thereof, a ribose, deoxyribose sugar moiety or an analogue thereof, and a phosphate group or phosphodiester linking group in the case of nucleotides within an oligonucleotide or polynucleotide. Hence, the term "nucleotide" encompasses naturally occurring nucleotides as well as "modified nucleotides" which comprise at least one modification in the linking phosphate-containing group, the purine or the pyrimidine, or the sugar moieties.

The term "nucleotide" includes deoxyribonucleoside triphosphates ("dNTPs") such as dATP (2'-deoxyadenosine 5'-triphosphate), dCTP (2'-deoxycytidine 5'-triphosphate), dITP (2'-deoxyinosine 5'-triphosphate), dUTP (2'-deoxyuridine 5'-triphosphate), dGTP (2'-deoxyguanosine 5'-triphosphate), dTTP (2'-deoxythymidine 5'-triphosphate), or derivatives thereof. Such derivatives include, for example, α-dATP, 7-deaza-dGTP, 7-deaza-dATP, Aminoallyl-UTP (5-[3-aminoallyl]-uridine-5'-triphosphate), Aminoallyl-dUTP, Aminoallyl-dUTP, Biotin-11-dUTP (biotin-e-aminocaproyl-[5-{3-aminoallyl}-2'-deoxyuridine-5'-triphosphate]), Fluorescein-12-dUTP (fluorescein-6-carboxaminocaproyl-[5-{3-aminoallyl}-2'-deoxyuridine-5'-triphosphate]), $dm^6ATP$ (2'-deoxy-N6-methyladenosine 5'-triphosphate), $dm^4CTP$ (2'-deoxy-N4-methylcytidine 5'-triphosphate) or $dm^5CTP$ (2'-deoxy-5-methylcytidine 5'-triphosphate). The term "nucleotide" as used herein also refers to dideoxyribonucleoside triphosphates ("ddNTPs") and their derivatives, including, but not limited to, ddATP, ddCTP, ddGTP, ddITP, and ddTTP. In addition, the term "nucleotide" includes ribonucleoside triphosphates (rNTPs) such as rATP, rCTP, rITP, rUTP, rGTP, rTTP and their derivatives, which are analogous to the above-described dNTPs and ddNTPs except that the rNTPs comprise ribose instead of deoxyribose or dideoxyribose in their sugar-phosphate backbone.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate some embodiments of the invention in a non limiting fashion.

Materials and Methods

Solvents were procured from Carlo Erba Reactifs-Sds and used without further purification unless indicated.

N,N-dimethylformamide was bubbled with nitrogen for 2 hours and kept over molecular sieves.

Acetonitrile was distilled before use from anhydrous potassium carbonate and kept over molecular sieves.

Diisopropylethylamine was refluxed for 2 hours with nihydrine, and then distilled and kept over molecular sieves.

Potassium hexafluorophosphate, morpholine, triphosgene, thiomorpholine, 4-chloro-3-nitrotrifluorobenzene, and 2-chloro-3-notropyridine, N-hydroxysuccinimide, pentafluorophenol were procured from Sigma-Aldrich.

Oxalyl chloride, N,N,N-trimethylethylenediamine, N,N-dimethylcarbamoyl chloride, N,N-diethylcarbamoyl chloride, potassium fluoride were procured from Fluka.

Potassium fluoride was kept in the oven at 100° C. for 24 hours for drying before use.

HOBt, HOAt, and Rink Amide resin were procured from Biotech GMBH.

6-Cl-HOBt was procured from Luxembourg industries.

Other starting materials and reagents were procured from Carlo Erba Reactifs-Sds, Sigma-Aldrich, Fluka, Biotech GMBH or Luxembourg industries Ltd.

TLC was performed on silica plates (8×4 cm) from Albet using suitable solvent systems and visualization by a Spectroline UV Lamp Model CM-10 (254 nm).

Melting points were obtained in open capillary tubes using a Buchi melting point B-540 Apparatus.

Infrared spectra (IR) were recorded on a FT-IR Thermo Nicolet series Fourrier Transformer instrument as KBr pellets. The absorption bands ($v_{max}$) were given in wave numbers ($cm^{-1}$).

UV-Vis spectra were recorded on a Shimadzu UV-250/PC spectrophotometer.

NMR spectra were recorded on Varian Mercury 400 MHz spectrometer at room temperature with chemical shifts reported as ppm relative to internal solvent used.

HPLC analysis was carried out by using a Waters Symmetry Column C18, 5μ, 4.6×150 mm with dual wavelength absorbance detector.

Mass spectrometry measurements were carried out on MALDI mass spectrometer with ACH as internal matrix.

X-ray crystallographic analysis was carried out using a Bruker Appex-II CCD diffractometer, using 3363 reflections with a four circle diffractometer.

Example 1

Chemical Syntheses of Various Urea Derivatives Designated as Uronium/Immonium Type Coupling Agents Preparation of Urea Derivatives—General Procedure A N,N-Dialkyl-carbamoyl chloride (0.6 mol) is added dropwise to a stirred mixture of a secondary amine compound (0.5 mol) and triethylamine (0.5 mol) in DCM (400 ml) at 0° C. The mixture is stirred for 3-4 hours at room temperature and is thereafter basified with 10% NaOH. The organic layer is collected and the aqueous layer is washed with dichloromethane (DCM, 100 ml). The combined DCM phase is washed with $H_2O$ (2×100 ml) and with a saturated solution of NaCl (2×100 ml), dried over anhydrous $MgSO_4$, filtered, and the solvent removed under reduced pressure. Typically an oily residue is obtained and purified by vacuum distillation.

Preparation of Urea Derivatives—General Procedure B

The urea derivative is prepared by using a two phase system consisting of DCM and 10% NaOH. A secondary amine (0.5 mole) is dissolved in DCM (300 ml) and 10% NaOH (300 ml). An N,N-dialkyl-carbamoyl chloride (0.6 mol in 200 ml of DCM) is added dropwise for 10 minutes. The reaction mixture is stirred at room temperature for 3 hours and the organic layer is collected. The NaOH layer is washed with DCM (200 ml) and the combined DCM is washed with water (2×100 ml), saturated NaOH (2×100 ml), dried ($MgSO_4$), filtered and the solvent is removed under reduced pressure to give the urea derivatives typically as pure colorless oil.

A series of exemplary urea derivatives was prepared according to General Procedure A or B (see Scheme 3 below) using a variety of cyclic secondary amines (represented as $R_1R_2NH$ in Scheme 3), such as pyrrolidine, morpholine, thiomorpholine, N-methyl-2-(pyrrolidin-1-yl)ethanamine, N-methyl-2-(piperidin-1-yl)ethanamine and N-methyl-2-morpholinoethanamine.

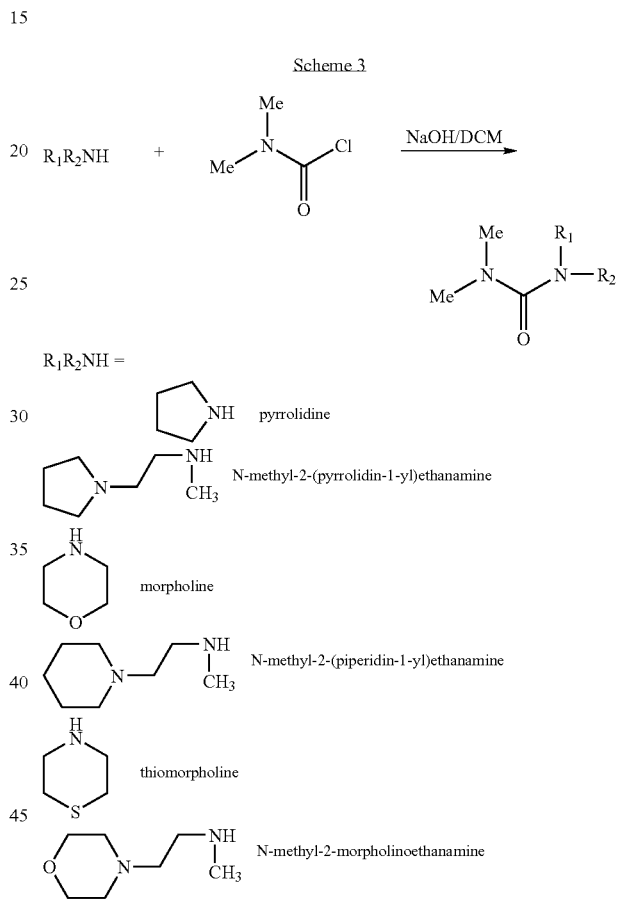

Preparation of N,N-dimethylpyrrolidine-1-carboxamide

N,N-dimethylpyrrolidine-1-carboxamide, a urea derivative, was distilled and collected at 98-100° C. as a colorless oil at 85.5% yield according to General Procedure A or B using pyrrolidine as a secondary amine.

$^1$H NMR (CDCl$_3$): δ=1.81-2.10 (m, 4H, 2CH$_2$), 2.81 (s, 6H, 2CH$_3$), 3.15-3.18 (m, 4H, 2CH$_2$) ppm Preparation of
N,N-Dimethylmorpholine-4-carboxamide

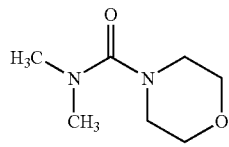

N,N-dimethylmorpholine-4-carboxamide, a urea derivative, was distilled and collected at 127-129° C. as a colorless oil at 92.4% yield (73 grams from 0.5 mole reaction) according to General Procedure A or B using morpholine as a secondary amine.

$^1$H NMR (CDCl$_3$): δ=2.84 (s, 6H, 2 CH$_3$), 3.22-3.2 (m, 4H, 2CH$_2$), 3.68-3.70 (m, 4H, 2CH$_2$) ppm;
$^{13}$C NMR (CDCl$_3$): δ=38.62, 47.51, 66.89, 164.96 ppm.

Preparation of
N,N-Dimethylthiomorpholine-4-carboxamide

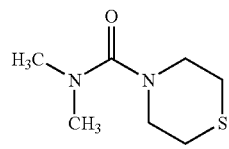

N,N-dimethylthiomorpholine-4-carboxamide, another urea derivative, was obtained as light brown crystals in 89.5% yield according to General Procedure A or B using thiomorpholine as a secondary amine.

m.p.: 61-62° C.;
$^1$H NMR (CDCl$_3$): δ=2.62-2.65 (m, 4H, 2CH$_2$), 2.81 (s, 6H, 2CH$_3$), 3.48-3.50 (m, 4H, 2CH$_2$) ppm;
$^{13}$C NMR (CDCl$_3$): δ=27.41, 38.77, 49.38, 165.17 ppm.

Preparation of Dimorpholinomethanone

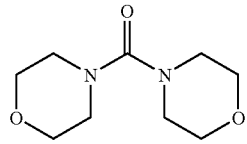 [SMILES: O=C(N1CCOCC1)N1CCOCC1]

Dimorpholinomethanone, another urea derivative, was synthesized by condensation of morpholine and triphosgene (BTC) in dichloromethane (DCM).

Morpholine (0.4 mol) in DCM (200 ml) was placed in a 250 ml three necked flask fitted with a dropping funnel, and a solution of BTC (0.033 mol), dissolved in DCM (100 ml), was added thereto under nitrogen atmosphere at 0° C. The reaction mixture was stirred at 0° C. for 1 hour, and for additional 3-4 hours at room temperature. Water (100 ml) was added to dissolve the white solid, the organic layer was collected and then washed with saturated Na$_2$CO$_3$ (50 ml), 1 N HCl (50 ml), saturated NaCl (50 ml), dried (MgSO$_4$), and filtered, and then the solvent was removed under reduced pressure to give a pure white solid in 86% yield.

m.p. 141-142° C.;
$^1$H NMR (CDCl$_3$): δ=3.19-3.21 (m, 8H, 4CH$_2$), 3.59-3.62 (m, 8H, 4CH$_2$) ppm;
$^{13}$C NMR (CDCl$_3$): δ=47.39, 66.75, 163.94 ppm.

Preparation of
1,1,3-trimethyl-3-(2-(pyrrolidin-1-yl)ethyl)urea

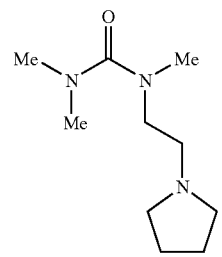 [SMILES: CN(C)C(=O)N(C)CCN1CCCC1]

1,1,3-trimethyl-3-(2-(pyrrolidin-1-yl)ethyl)urea, another urea derivative, was distilled and collected at 134-135° C. as pale yellow oil in 74.2% yield (11.6 grams from 78 mmol) according to General Procedure A or B using N-methyl-2-(pyrrolidin-1-yl)ethanamine as a secondary amine.

$^1$H NMR (CDCl$_3$): δ=1.75-1.78 (m, 4H, 2 CH$_2$), 2.52-2.56 (m, 4H, 2 CH$_2$), 2.65 (t, 2H, CH$_2$), 2.79 (s, 6H, 2 CH$_3$), 2.84 (s, 3H, CH$_3$), 3.12 (t, 2H, CH$_2$), ppm.
$^{13}$C NMR (CDCl$_3$): δ=23.67, 37.18, 38.91, 49.80, 53.94, 54.54, 165.68 ppm. m/z: 199.17.

Preparation of
1,1,3-trimethyl-3-(2-(piperidin-1-yl)ethyl)urea

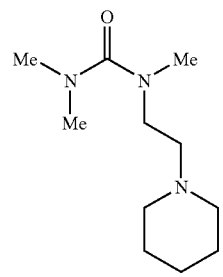 [SMILES: CN(C)C(=O)N(C)CCN1CCCCC1]

1,3-trimethyl-3-(2-(piperidin-1-yl)ethyl)urea, another urea derivative, was distilled and collected at 89-91° C. as colorless oil in 81.7% yield (34.8 grams from 0.3 mole) according to General Procedure A or B using N-methyl-2-(piperidin-1-yl)ethanamine as a secondary amine.

$^1$H NMR (CDCl$_3$): δ=1.39-1.45 (m, 2H, CH$_2$), 1.54-1.59 (m, 4H, 2 CH$_2$), 1.60-1.65 (br, 1H, NH), 2.35-2.41 (m, 4H, 2 CH$_2$), 2.37-2.44 (m, 5H, CH$_2$, CH$_3$), 2.66 (t, 2H, CH$_2$) ppm.

Preparation of 1,1,3-trimethyl-3-(2-morpholinoethyl)urea

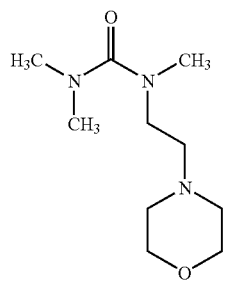

1,1,3-trimethyl-3-(2-morpholinoethyl)urea, another urea derivative, was distilled and collected at 152-154° C. as pale yellow oil in 76.8% yield according to General Procedure A or B using N-methyl-2-morpholinoethanamine as a secondary amine.

$^1$H NMR (CDCl$_3$): δ=2.45 (t, 4H, 2CH$_2$), 2.54 (t, 2H, CH$_2$), 2.77 (s, 6H, 2CH$_3$), 2.82 (s, 3H, CH$_3$), 3.29 (t, 2H, CH$_2$), 3.66 (t, 4H, 2CH$_2$) ppm.

$^{13}$C NMR (CDCl$_3$): δ=37.33, 38.91, 47.36, 54.04, 56.47 ppm.

Preparation of Chloroiminium Derivatives—General Procedure C

The preparation of chloroiminium derivatives was carried out as depicted in Scheme 4 below:

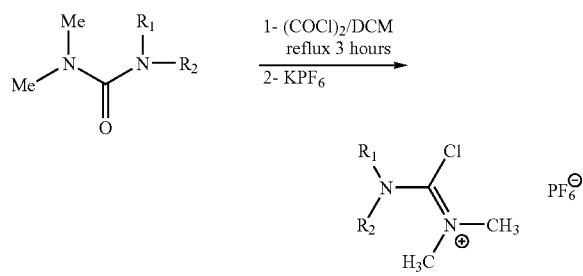

Scheme 4

Oxalyl chloride (100 mmol) in DCM (100 ml) is added dropwise to a solution of urea derivative (100 mmol) in dry DCM (200 ml) at room temperature over a period of 5 minutes. The reaction mixture is stirred under reflux for 3 hours, and the solvent is removed under reduced pressure, the residue is washed with anhydrous ether (2×100 ml), and then bubbled with N$_2$ to remove excess of ether. The residue obtained is typically very hygroscopic, and therefore it is dissolved directly in DCM, and a saturated aqueous potassium hexafluorophosphate (100 mmol in 50 mL water, KPF$_6$) solution is added at room temperature with vigorous stirring for 10-15 minutes. The organic layer is collected, washed once with water (100 ml), dried over anhydrous MgSO$_4$, filtered and the solvent is removed under reduced pressure to give typically a white solid which can be recrystallized from DCM-ether or acetonitrile-ether to afford typically white crystals.

Preparation of 4-((dimethylamino)chloromethylene)morpholin-4-iminium hexafluorophosphate (DCMH)

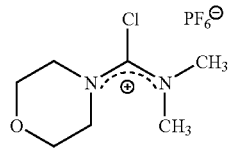

Oxalyl chloride (100 mmol) in DCM (100 ml) was added dropwise to a solution of N,N-Dimethylmorpholine-4-carboxamide (100 mmol), prepared according to General Procedure A. or B, in dry DCM (200 ml) at room temperature over a period of 5 minutes. The reaction mixture was stirred under reflux for 3 hours, the solvent was thereafter removed under reduced pressure and the residue was washed with anhydrous ether (2×100 ml), and then bubbled with N$_2$ to remove excess of the ether. The obtained white solid was dissolved in DCM (500 ml), and a saturated aqueous KPF$_6$ (18.4 grams in 50 ml H$_2$O) was added at room temperature with vigorous stirring for 10-15 minutes. The organic layer was collected, washed once with H$_2$O (50 ml), dried over anhydrous MgSO$_4$, filtered and the solvent was removed under reduced pressure to give a white solid, which was recrystallized from DCM-ether to give white crystals in 89.6% yield (28.9 grams).

m.p. 94-95° C.;

$^1$H NMR (CD$_3$COCD$_3$): δ=3.39 (s, 6H, 2CH$_3$), 3.75 (t, 4H, 2CH$_2$), 3.86 (t, 4H, 2CH$_2$) ppm;

$^{13}$C NMR (CD$_3$COCD$_3$): δ=44.36, 52.82, 65.99, 162.79 ppm.

Preparation of N-(Chloro(pyrrolidin-1-yl)methylene)-N-methylmethanaminium hexafluorophosphate (DmPyCH)

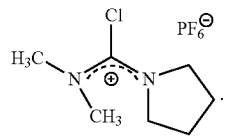

N-(chloro(pyrrolidin-1-yl)methylene)-N-methylmethanaminium hexafluorophosphate (DmPyCH) was prepared according to General Procedure C and as described for DCMH hereinabove, and obtained as white solid in 89.0%, yield.

m.p. 93-95° C.;

$^1$H NMR (CD$_3$COCD$_3$): δ=2.00-2.13 (m, 4H, 2CH$_2$), 3.49 (s, 6H, 2CH$_3$), 3.90-4.02 (m, 4H, 2CH$_2$) ppm.

Preparation of 1-(chloro(morpholino)methylene)pyrrolidinium hexafluorophosphate 1-(chloro(morpholino)methylene)pyrrolidinium hexafluorophosphate was prepared as depicted in Scheme 5 below:

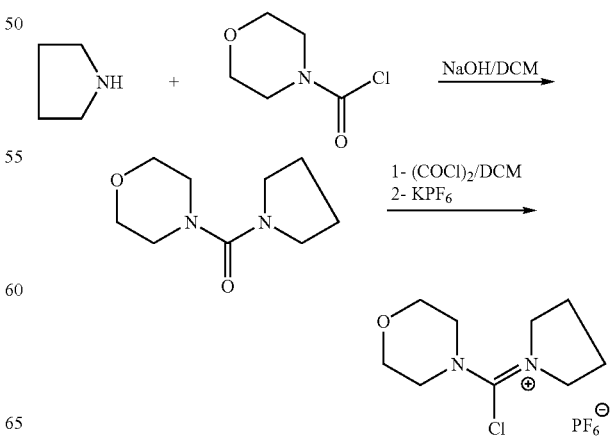

Scheme 5

4-Morpholino carbonyl chloride (36 grams, 1.2 equivalents) in 100 ml DCM was added over a period of time 10 minutes oo a stirred solution of pyrrolidine (0.2 mole, 17 ml) in 100 ml DCM and 100 ml of 10% NaOH. The reaction mixture was stirred at room temperature for 3 hours and then the organic layer was collected and then the NaOH layer was washed with 100 ml DCM. The combined DCM was washed with water (2×100 ml), dried (MgSO$_4$), filter and the solvent was removed under vacuum to give colorless oil at a yield of 92.4% (34 grams) which solidified at room temperature.

The crude urea derivatives further purified by vacuum distillation and collect the fraction at 165-169° C.

$^1$H NMR (CDCl$_3$): δ=1.76-1.81 (m, 4H, 2CH$_2$), 3.24 (t, 4H, 2 CH$_2$), 3.32-3.35 (m, 4H, 2 CH$_2$), 3.64 (t, 2H, CH$_2$) ppm;

$^{13}$C NMR (CDCl$_3$): δ=25.72, 46.84, 48.52, 66.97, 162.84 ppm;

The chloroiminium salt was prepared according to General Procedure C as described hereinabove. The product was obtained as white solid at a yield of 83.9%.

m.p. 99-100° C.

$^1$H NMR (acetone-d$_6$): δ=2.10-2.14 (m, 4H, 2CH$_2$), 3.87 (t, 4H, 2CH$_2$), 4.00 (t, 4H, 2CH$_2$), 4.04-4.06 (m, 4H, 2CH$_2$) ppm;

$^{13}$C NMR (CDCl$_3$): δ=25.80, 51.75, 55.97, 65.97, 154.85 ppm.

Example 2

Chemical Syntheses of Various Compounds Designated as Leaving Groups in Coupling Agents Preparation of N-hydroxyindolin-2-one (HOI)

The synthesis is adapted from the art [Kenneth H. Collins, *J. Amer. Chem. Soc.*, 78, 221-224 (1956)] and illustrated in Scheme 6 below.

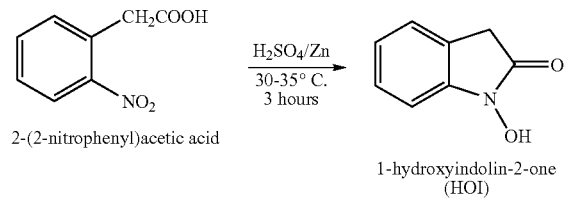

2-nitrophenylacetic acid (9 grams, 50 mmol) was dissolved in 50% H$_2$SO$_4$ (40 ml) and then 7 grams of zinc powder was added over a period of time 1 hour. The reaction mixture was stirred for 3 hours at 30-35° C. and the insoluble portion was filtered off. The product was dissolved in Na$_2$CO$_3$ solution and reprecipitated with HCl, filtered, dried and recrystallized from water to afford pale yellow solid at a yield of 20% (1.5 grams).

m.p. 198-199° C.;

$^1$H NMR (DMSO-d$_6$): δ=3.97 (s, 2H, CH$_2$), 7.51-7.56 (m, 2H, ar) 7.68 (t, 1H, ar), 8.04 (d, 1H, ar), 12.51 (br, 1H, OH) ppm.

Preparation of 3-hydroxy-2-methylquinazolin-4-one (HOMQ)

The synthesis is adapted from the art [F. Gutierrez, C. Tedeschi, L. Maron, J-P. Daudey, R. Poteau, J. Azema, P. Tisnes, and C. Picard, *Dalt. Trans.* 1334-1347 (2004)] and illustrated in Scheme 7 below.

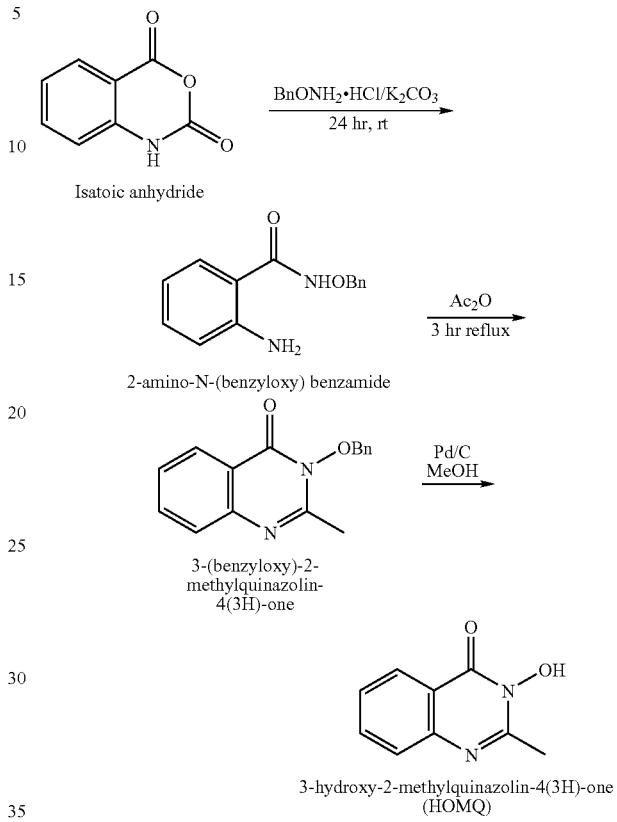

K$_2$CO$_3$ (0.93 gram) was slowly added to a solution of o-benzyl hydroxylamine/HCl (2.16 grams, 12.58 mmol) in water (60 ml). This mixture was stirred for 30 minutes and then isatoic acid anhydride (2 grams, 12.3 mmol) was added thereto. The reaction mixture was kept at room temperature under stirring for 24 hours and then filtered. The solid was dried under reduced pressure and then recrystallized form dichloromethane-hexane to give light brown solid at a yield of 89.7% (5.34 grams).

m.p. 105-106° C.;

$^1$H NMR (CDCl$_3$): δ=5.02 (s, 2H, CH$_2$), 6.58-6.62 (m, 1H, ar), 6.67-6.69 (m, 1H, ar), 7.1-7.25 (m, 3H, ar), 7.37-7.46 (m, 6H, ar, NH), 8.37-8.46 (brs, 1H, NH) ppm.

A mixture of 2-amino-N-benzyloxy benzamide (2 grams, 8.25 mmol) and acetic anhydride (9.12 ml, 8.5 mmol) was heated under reflux for 2 hours. After cooling, water (3.9 ml) and activated carbon were added while it is hot and the mixture was boiled for a further 30 minutes, followed by filtration through Celite pad. The Celite pad was washed with methanol and the combined filtrates were evaporated under reduced pressure. The residue was filtered through a silica gel using (DCM-MeOH, 9:1), and then the solvent was evaporated under reduced pressure. The crude residue was dissolved in MeOH and treated with (0.02 gram) of Pd/C for 30 minutes. at room temperature, filter through Celite and wash with MeOH. The combined MeOH was evaporated under vacuum to afford the product at a yield of 48.1%.

m.p. 161-162° C.;

$^1$H NMR (DMSO-d6): δ=2.27 (s, 3H, CH$_3$), 7.13 (t, 1H, ar), 7.61 (t, 1H, ar), 8.13 (d, 1H, ar), 8.73 (d, 1H, ar), 11.04 (s, 1H, OH) ppm.

The same compound was prepared using Acetyl chloride-triethylamine in acetic acid as follows.

2-Amino-N-hydroxybenzamide (10 mmole) of was suspended in 10 mmol of triethylamine (exothermic dissolution) and then acetic acid (10 ml) was added followed by adding acetyl chloride (1 ml) at room temperature. The reaction mixture was stirred at room temperature for 1 hour and then 20 ml of water were added thereto. The precipitate was collected by filtration, dried to give the pure product at a yield of 78.5%.

Preparation of 3-hydroxyquinazolin-4-one (HOQ)

The synthesis was adapted from the art [Robert H. Clark and E. C. Wagner, *J. Org. Chem.*, 1, 55-67 (1944)], and started with the synthesis of 2-amino-N-hydroxybenzamide, as illustrated in Scheme 8 below.

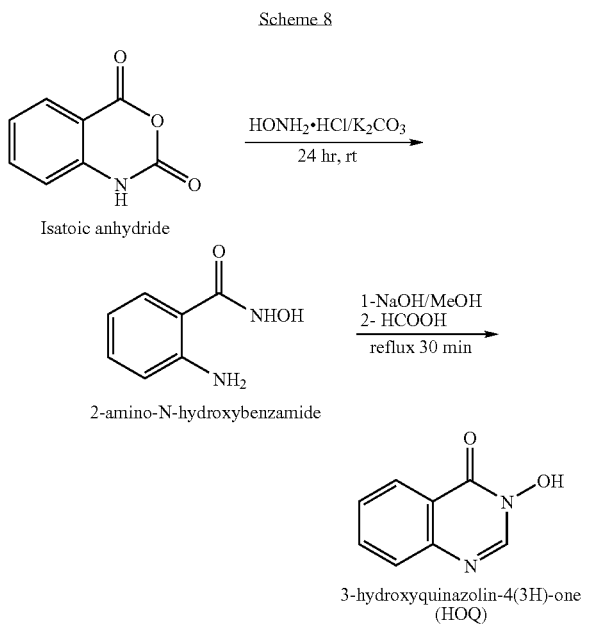

Na$_2$CO$_3$ (5.5 grams, 0.55 mole, 1 equivalent) was added to a solution of hydroxylamine hydrochloride (6.9 g, 0.1 mole, 1 equivalent) in 250 ml of water. Isatoic anhydride (8.15 grams, 0.05 mole) was added to the solution, which started the reaction spontaneously. The reaction mixture was allowed to stand at room temperature overnight. The solid product was filtered and recrystallized from water at 40° C., dried briefly in the air and completely under reduced pressure (this compound is sensitive for moist air) to afford the product at a yield of 85.8%.

m.p 86° C.

The procedure proceeded with the synthesis of 3-hydroxyquinazolin-4-one (HOQ), effected by two methods as follows.

Method (A):

A mixture of 1.52 grams (10 mmol) of the hydroxamic acid and 4 ml of 98% formic acid was heated under reflux for 15 minutes, after which 10 ml of water was added and the whole mixture was boiled for 15 minutes and cooled to room temperature. The precipitate was collected by filtration and washed with cold water (2×5 ml) dried to afford 0.35 grams (22% yield) of yellowish white solid.

m.p. 272-274° C. (decomposed);

$^1$H NMR (DMSO-d$_6$): δ=7.54 (td, 1H, ar), 7.71 (dd, 1H, ar), 7.82 (td, 1H, ar), 8.17 (dd, 1H, ar), 8.53 (s, 1H, ar), 11.92 (br, 1H, OH) ppm.

Method (B):

8 mmol of the hydroxamic acid was dissolved in 20 ml of MeOH contained 8 mmol of NaOH, and the solution was stirred at room temperature for 30 minutes. The solvent was evaporated to dryness and the residual solid was dissolved in 8 ml of 98% formic acid. The reaction mixture was refluxed for 30 minutes and then cooled to room temperature. Dilute with water (20 ml) to afford a yellowish white solid, filtered, dried and then recrystallized from water to afford light brown solid 0.59 grams (37% yield).

m.p. 270-272° C. (decomposed);

$^1$H NMR (DMSO-d$_6$): δ=7.54 (td, 1H, ar), 7.71 (dd, 1H, ar), 7.82 (td, 1H, ar), 8.17 (dd, 1H, ar), 8.53 (s, 1H, ar), 11.92 (br, 1H, OH) ppm.

Preparation of 6-Chloro-3-hydroxyquinazolin-4-one (6-Cl-HOQ)

The compound was prepared according to the Method (B) described hereinabove and illustrated in Scheme 9 below.

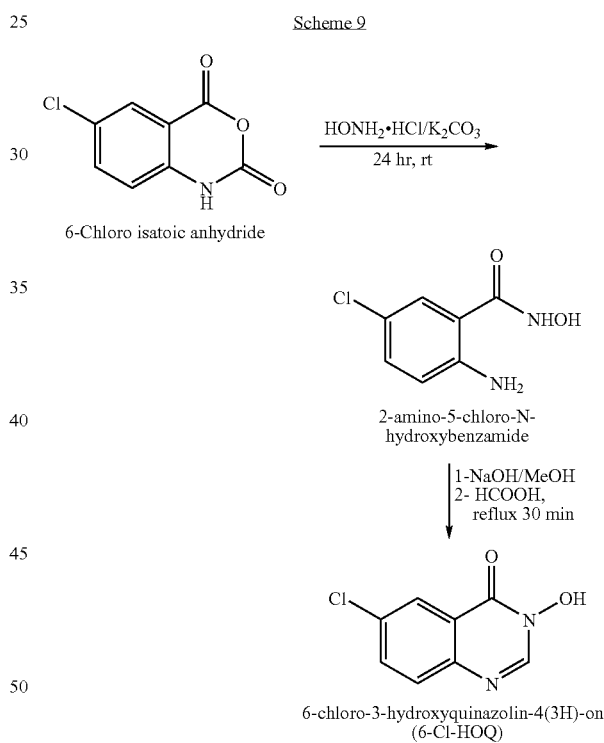

The product was obtained in 0.71 grams (36.6% yield from 10 mmol reaction) as light brown solid.

m.p. 268-269° C.;

$^1$H NMR (DMSO-d$_6$): δ=7.74 (d, 1H), 7.85 (dd, 1H), 8.09 (d, 1H), 8.56 (s, 1H), 12.02 (s, 1H, OH, exchangeable with D$_2$O).

Preparation of 6-Chloro-3-hydroxy-2-methylquinazolin-4-one (6-Cl-HOMQ)

The synthesis of 6-Chloro-3-hydroxyl-methylquinazolin-4-one (6-Cl-HOMQ) is illustrated in Scheme 10 below.

Scheme 10

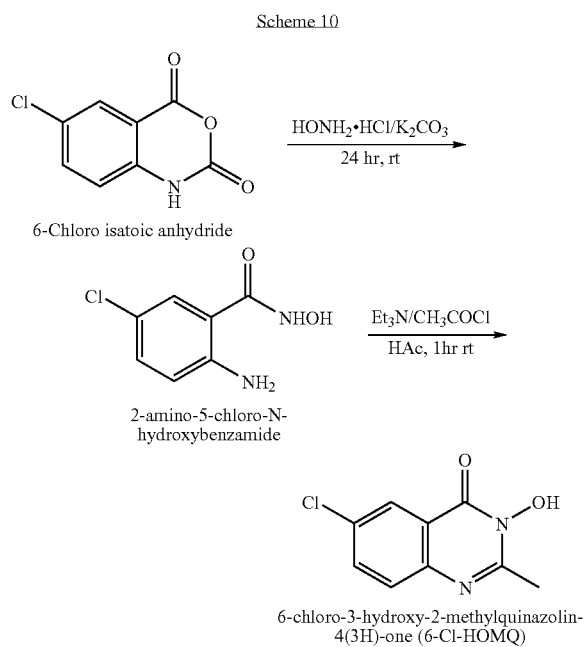

2-amino-5-chloro-N-hydroxybenzamide (1.86 grams, 10 mmole) was suspended in triethylamine (1.3 ml, 10 mmole) and then acetic acid (10 ml) was added followed by the addition of acetyl chloride (1 ml) at room temperature. The reaction mixture was stirred at room temperature for 1 hour and then 20 ml of water were added thereto. The precipitate was collected by filtration, washed with cold water, dried to give 1.69 grams of the pure product at a yield of 80.3%.

m.p. 183-185° C.;

$^1$H NMR (DMSO-d$_6$): δ=2.11 (s, 3H, CH$_3$), 7.63 (dd, 1H), 7.87 (d, 1H), 8.45 (d, 1H), 10.93 (s, 1H, OH) ppm.

Preparation of N-hydroxy-2-phenylbenzimidazole (HOPBI)

The synthesis of N-hydroxy-2-phenylbenzimidazole (HOPBI) is illustrated in Scheme 11 below:

Scheme 11

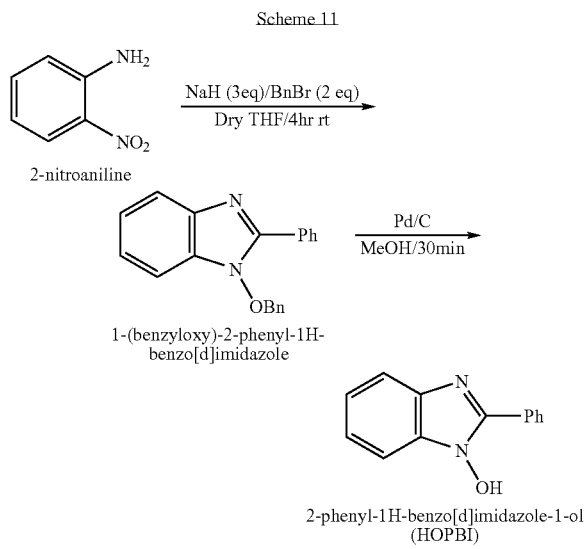

Method (A):

Adapted from the art [N. D. Kokare, R. R. Nagwade, V. P. Rane, D. B. Shinde, *Synthesis*, 766-772 (2007)] is effected as follows. NaH (48 mmol, 3.25 grams of 60% dispersed in mineral oil, washed three times with dry THF before use) suspended in THF dry (30 ml) and 2-nitroaniline (2.68 grams, 20 mmol) was added portion-wise with cooling. After 15 minutes, benzyl bromide (5.8 grams, 50 mmol) was added slowly and the reaction mixture was heated at 80° C. for 4 hours. The reaction mixture was cooled to room temperature, quenched with water (25 ml) and extracted into ethylacetate (2×15 ml). The organic layer wad dried (Na$_2$SO$_4$) and concentrated under vacuum. The product was isolated by trituration with hexane and filtration to afford an off-white solid, at a yield of 87.2% (5.1 grams). The NMR showed some traces of starting materials (about 12-15%), and further recrystallized or purified by column was required.

$^1$H NMR (CDCl$_3$): δ=5.10 (s, 2H), 7.20-7.40 (m, 5H), 7.60-7.80 (m, 5H), 7.8 (d, 2H), 8.20 (d, 2H) ppm.

Method (B):

Adapted from the art [J. M. Gardiner, C. R. Loyns, C. H. Schwallabe, G. C. Barrett, P. R. Lowe, *Tetrahedron*, 51, 4101-4110 (1995)] is effected as follows. O-Nitroaniline (14.5 mmol) was dissolved in dry THF (100 ml), and NaH (60% in oil, 1.45 mmol) added at ambient temperature. Benzyl bromide (14.5 mmol) was added slowly, and the reaction was refluxed for 4 hours. The reaction was cooled to ambient temperature, and further 14.5 mmol of NaH were added slowly, the reaction heated a further 4 hours, and the second portion of benzyl bromide (14.5 mmol) was added. After a further 4 hours, the reaction was again cooled to ambient temperature, a third portion of NaH (14.5 mmol) was added and the reaction heated for further 4 hours (NaH must be washed three times with THF before used). The reaction was cooled and quenched with NaCl solution, extracted with DCM (3×100 ml). The organic extracts were combined, washed with saturated NaCl solution (100 ml), dried (Na$_2$SO$_4$), filter and the solvent was removed under vacuum. The crude solid product was triturated with hexane three times (3×100 ml) to afford a white solid at a yield of 88.4%.

The crude product (5.3 grams, 0.17 mol) was dissolved in MeOH (50 ml), Pd/C (10%, 500 mg) was added and the reaction mixture was stirred under H$_2$ atmosphere at room temperature for 15-30 minutes (TLC, AcOEt, hexane 1:1). The reaction mixture was filtered through high-flow Celite and the filtrate was concentrated and purified by column chromatograph (MeOH—CHCl$_3$, 1:9) to yield the N-hydroxy compound as a white solid at a yield of 75.9% (2.75 grams).

$^1$H NMR (DMSO-d$_6$): δ=7.23-7.46 (m, 2H), 7.61-7.83 (m, 5H, Ph), 8.22 (d, 2H), 12.22 (s, 1H, OH) ppm.

Preparation of 6-Chloro-N-hydroxy-2-phenylbenzimidazole (6-Cl-HOPBI)

6-Chloro-N-hydroxy-2-phenylbenzimidazole (6-Cl-HOPBI) was prepared as illustrated in Scheme 12 below.

Scheme 12

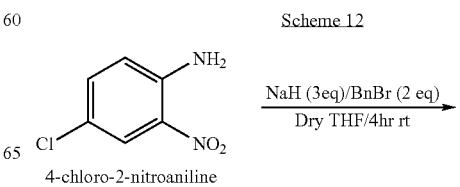

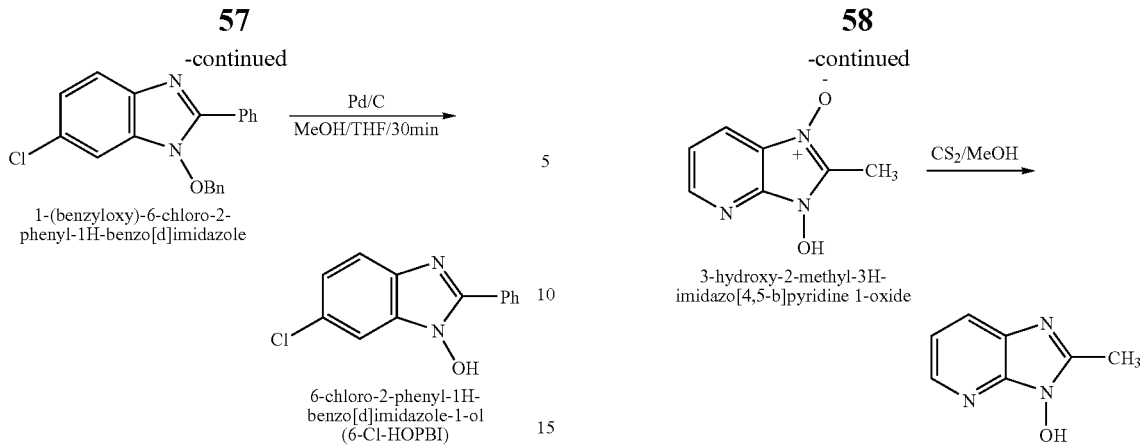

The product was obtained using Method (B) as light brown crystals to afford 4.22 grams from 20 mmol (65.8% yield).

m.p. 123-124° C.;

$^1$H NMR (CDCl$_3$): δ=5.03 (s, 2H, CH$_2$), 7.19-7.38 (m, 7H), 7.51 (t, 3H), 7.68 (d, 1H), 8.13-8.16 (m, 2H).

The OBn derivative (3.345 grams, 10 mmol) was dissolved in 10 ml MeOH and 10 ml THF. Thereafter Pd/C (10%, 500 mg) was added and the reaction mixture was stirred under H$_2$ atmosphere at room temperature for 15-30 minutes (TLC, AcOEt, hexane 1:1). The reaction mixture was filtered through high-flow Celite and the filtrate was concentrated and purified washing with ether (2×10 ml) to afford the pure product as off white solid at a yield of 73% (1.78 grams).

m.p. 262-264° C.;

$^1$H NMR (DMSO-d$_6$): δ=7.25 (dd, 1H), 7.53-7.57 (m, 4H, Ph), 7.68 (d, 1H), 8.20-8.25 (m, 2H), 12.19 (s, 1H, OH) ppm.

$^{13}$C NMR (DMSO-d$_6$): δ=123.72, 125.90, 130.35, 131.35, 132.36, 133.87, 134.88, 135.58, 136.35, 147.34, 148.17, 159.99, 165.26 ppm.

Preparation of 2-methyl-3H-imidazole[4,5-b]pyridine-3-ol (HOMPI)

2-methyl-3H-imidazole[4,5-b]pyridine-3-ol (HOMPI) was prepared as illustrated in Scheme 13 below.

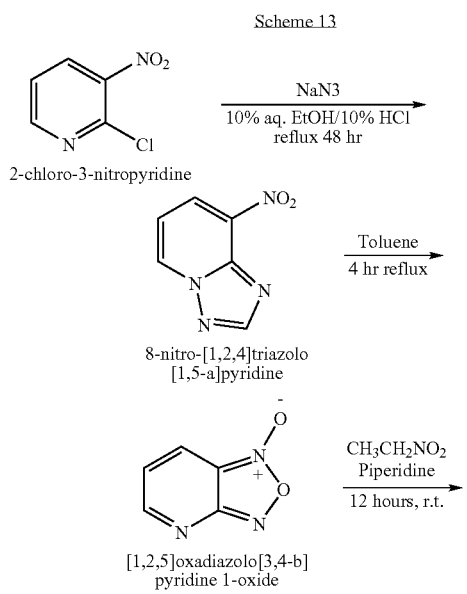

8-Nitro-[1,2,4]triazole[1,5-a]pyridine was prepared according to a published procedure [Charlotte K. Lowe-Ma, Robin A. Nissan, William S. Wilson, *J. Org. Chem.*, 55, 3755-3761 (1990)] as follows. 2-chloro-3-nitropyridine (4 grams, 25.6 mmol) and sodium azide (4 grams, 61.6 mmol) were dissolved in 10% aqueous ethanol (400 ml) at ambient temperature, and 10% HCl (40 ml) was added. The solution was then heated under reflux for 48 hours. Evaporation to dryness, addition of water (80 ml) and filtration afforded buff solid residue which recrystallized from ethanol to afford light brown crystals 2.4 g (74.1% yield).

m.p. 176-178° C.;

$^1$H NMR (DMSO-d$_6$): δ=7.65 (t, 1H), 8.88 (d, 1H), 9.76 (d, 1H) ppm.

[1,2,5]-Ioxadiazoleo[3,4-b]pyridine 1-oxide was prepared as follows. 8-nitro-[1,2,4]triazole[1,5-a]pyridine (1 gram, 6 mmol) was dissolved in toluene (100 ml) and heated under reflux for 4 hours. The solution was decolorized with charcoal and filtered, evaporation to dryness to produce a pale yellow solid which recrystallized from cyclohexane to afford a yellow crystals at a yield of 62.4% (0.52 grams).

m.p. 54-56° C.;

$^1$H NMR (acetone-d$_6$): δ=7.47 (dd, 1H), 8.25 (dd, 1H), 8.65 (dd, 1H) ppm.

3-Hydroxy-2-methyl-3H-imidazole[4,5,b]pyridine 1-oxide was prepared according to a published procedure [M. Boiani, L. Boiani, A. Denicola, S. Torres de Ortiz, E. Serna, N. Verade Bilbao, L. Sanabria, G. Yaluff, H. Nakayama, A. Rojasde Arias, C. Vega, M. Rolan, A. Gömez-Barrie, H. Cerecette, M. Gonzàlez, J. Med. Chem., 49, 3215-3224 (2006)] as follows. [1,2,5]oxadiazoleo[3,4-b]pyridine 1-oxide (3 mmol) and nitroethane (3 mmol) were dissolved in 5 ml of THF. Piperidine (3 mmol) was added drop-wise (exothermic reaction). After complete addition the reaction mixture was left to stand at room temperature for 12 hours. Filter for the brown precipitate which recrystallized from DCM-hexane.

Preparation of Potassium Salt of Hydroxycarbonimidoyl Dicyanide

The synthesis was effected according to a published procedure [Mitsuru Kitamura, Shunsuke Chiba, Koichi Narasaka, *Bull. Chem. Soc. Jpn*, 76, 1063-1070 (2003)] as illustrated in Scheme 14 below.

Scheme 14

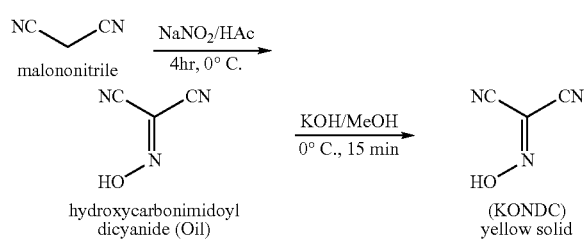

Sodium nitrite (14.2 grams, 206 mmol) was added slowly at ° C. over 20-30 minutes to a solution of malononitrile (9.06 grams, 138 mmol) in acetic acid (20 ml) and water (50 ml) and then the mixture was stirred at the same temperature for 45 minutes. After quenching the reaction with 2N HCl (100 ml), the reaction was extracted three times with ether (3×100 ml). The extracts were dried over anhydrous $Na_2SO_4$, and the ether was removed under vacuum to give an oily residue. The oily product was added slowly to a cold solution of KOH (8.0 grams) in MeOH (100 ml), and then the reaction mixture was stirred at ° C. for 20 minutes. Excess ether was added to afford the pot salt as yellow crystals at a yield of 77.5% (14.1 grams).

Preparation of potassium salt of diethyl 2-(hydroxyimino)malonate

Potassium salt of diethyl 2-(hydroxyimino)malonate was prepared according to a published procedure [Kenneth N. F. Shaw and Chis Nolan, *J. Org. Chem.*, 22, 1668-1670 (1957)] as illustrated in Scheme 15 below.

Scheme 15

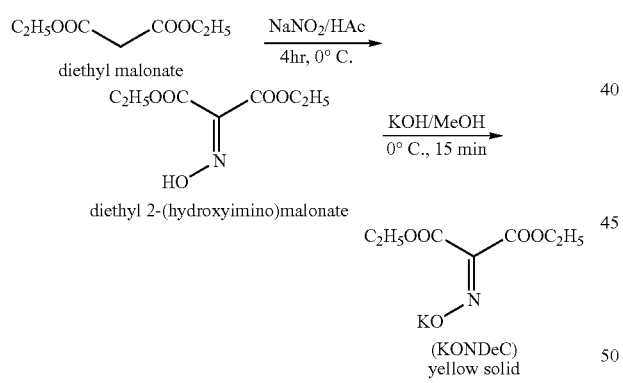

A solution of 16 grams (0.1 mole) of diethylmalonate in 17.5 ml (0.3 mole) of glacial acetic acid was stirred vigorously at 0-5° C. while addition of a solution of 20.7 grams of $NaNO_2$ (0.3 mole) in 250 ml of water was added drop-wise during 3-4 hours. The ice bath was removed and the mixture was stirred vigorously for additional 20 hours. The nitrosation was carried out in three nicked flask with appropriate fitting and a small vent to permit escape of nitric oxide. The reaction mixture was extracted with 400 ml and then three 100 ml portions of DCM. The combined DCM extracts were dried over anhydrous $Na_2SO_4$. The DCM was removed under vacuum and the resulting oily product was dissolved in 400 ml of DCM, stirred with anhydrous $K_2CO_3$ (32 grams) for 15 minutes and filtered, and the DCM was concentrated until 200 ml. Thereafter ether was added until the solution became cloudy, and then kept in the refrigerator over night to afford off white crystals at a yield of 63.4% m.p. 116-118° C.;
$^1H$ NMR ($CDCl_3$): δ=1.24-1.29 (q, 6H, 2 $CH_3$), 4.20-4.29 (m, 4H, 2$CH_2$) ppm.

Preparation of 2-Pyridylhydroxyiminoacetonitrile

2-Pyridylhydroxyiminoacetonitrile was prepared according to a published procedure [Jan Izdebski, *Polish J. Chem.*, 53, 1049-1057 (1979)] as illustrated in Scheme 16 below.

Scheme 16

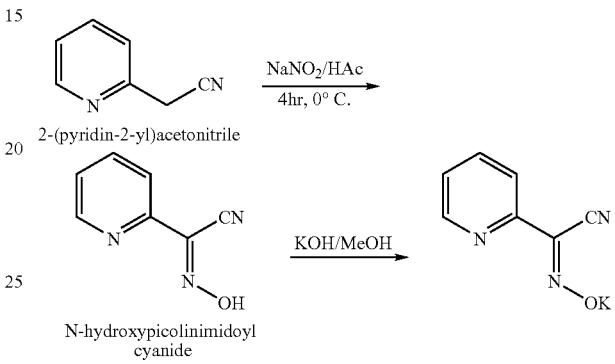

A solution of sodium nitrite (4.5 grams, 0.065 mole in 5 ml water) was added slowly to a solution of 2.2 grams (0.019 mole) of 2-pyridylacetonitrile in 4.5 ml of glacial acetic acid. After 12 hours standing the precipitate was filtered off, washed with water, dried and then recrystallized from ethanol to afford the product at a yield of 65% m.p 220-222° C.;
$^1H$ NMR (DMSO-$d_6$): δ=7.45-7.52 (1H), 7.87-7.90 (2H), 8.67 (d, 1H), 14.12 (OH) ppm.

Example 3

Chemical Syntheses of Various Uronium/Immonium Type Coupling Agents

Preparation of 1-((dimethylimino)(morpholino)methyl)3-H-benzo[1,2,3]triazolo-1-ium-3-olate Hexafluorophosphate (HDMB)

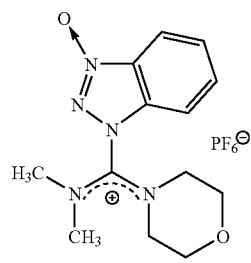

4-((Dimethylamino)chloromethylene) morpholin-4-iminium hexafluorophosphate (6.45 grams) was added to a solution of HOBt (20 mmol, 2.7 grams) and triethylamine (20 mmol, 2.8 grams) in DCM (50 ml) at 0° C. The reaction mixture was stirred at this temperature and allowed to warm up to room temperature overnight. The obtained white precipitate was filtered, washed with cooled DCM, and re-crystallized from acetonitrile-ether to give white crystals at 88.27% yield (7.54 grams).

m.p.: 196-197° C. (decomposed);

$^1$H NMR (CD$_3$COCD$_3$): δ=3.22 (s, 3H, CH$_3$), 3.51 (s, 3H, CH$_3$), 3.66-3.88 (m, 4H, 2CH$_2$), 4.03-4.06 (m, 4H, 2CH$_2$), 7.65-7.96 (dt, 1H, ar), 7.86-7.92 (dm, 2H, ar), 7.98.7.99 (dd, 1H, ar) ppm.;

$^{13}$C NMR (CD$_3$COCD$_3$): δ=41.76, 42.23, 50.81, 51.51, 66.19, 66.41, 109.99, 114.56, 127.52, 133.54 ppm.

MS (MALDI with ACH matrix): m/z=421.23

FIG. 1 presents the X-ray crystal structure of HDMB, showing that the coupling agent in the N-form thereof, as opposed to the O-form, meaning that the benzotriazole moiety is attached to the iminium moiety directly via one of the triazole nitrogen atoms and not via an oxygen atom as in the case of the known coupling agent, HBTU.

Preparation of 1-((dimethylimino)(morpholino)methyl)3-H-6-chlorobenzo[1,2,3]triazolo-1-ium-3-olate hexafluorophosphate (6-Cl-HDMB)

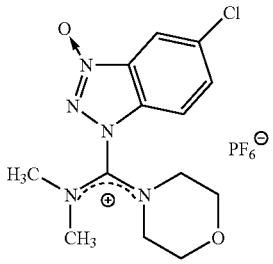

6-Cl-HDMB was prepared according to the method described hereinabove for the preparation of HDMB, using 6-Cl-HOBt instead of HOBt. The product was obtained at 93.5% yield.

m.p.: 193-194° C. (decomposed);

$^1$H NMR (CD$_3$COCD$_3$): δ=3.31 (s, 3H, CH$_3$), 3.69 (s, 3H, CH$_3$), 3.94-3.951 (m, 4H, 2CH$_2$), 4.12-4.14 (m, 4H, 2CH$_2$), 7.96-8.03 (qd, 2H, ar), 8.12-8.13 (dd, 1H, ar) ppm;

$^{13}$C NMR (CD$_3$COCD$_3$): δ=41.78, 42.30, 50.84, 51.58, 66.21, 66.39, 115.77, 116.18, 132.85, 133.93, 150.49 ppm.

Preparation of 1-((dimethylimino)(morpholino)methyl)3-H-[1,2,3]triazolo[4,5-b]pyridine-1-3-olate hexafluorophosphate (HDMA)

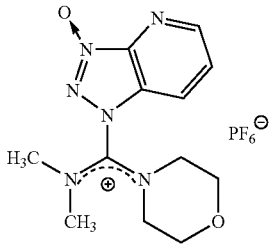

HDMA was prepared according to the method described hereinabove for the preparation of HDMB, using HOAt instead of HOBt. The white solid was recrystallized from acetonitrile-ether to give white crystals at 91% yield.

m.p. 194-195° C. (decomposed);

$^1$H NMR (CD$_3$COCD$_3$): δ=3.27 (s, 3H, CH$_3$), 3.64 (s, 3H, CH$_3$), 3.85-3.89 (m, 4H, 2CH$_2$), 4.00-4.07 (m, 4H, 2CH$_2$), 7.93-7.96 (dd, 1H, ar), 8.44-8.47 (dd, 1H, ar), 8.76-8.77 (dd, 1H, ar) ppm;

$^{13}$C NMR (CD$_3$COCD$_3$): δ=41.74, 42.35, 50.82, 51.58, 66.19, 66.42, 124.37, 127.84, 149.65 ppm;

MS (MALDI with ACH matrix): m/z=422.2.

Preparation of 1-((dimethylimino)(morpholino)methyl)3-H-[1,2,3]triazolo[2,3-b]pyridine-1-ium-3-olate hexafluorophosphate (4-HDMA)

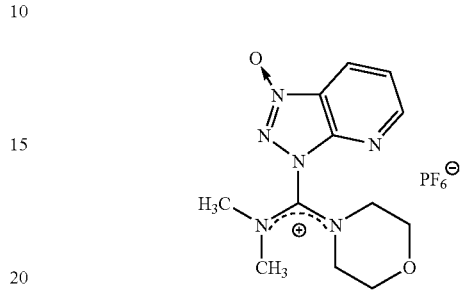

4-HDMA was prepared according to the method described hereinabove for the preparation of HDMB, using 4-HOAt instead of HOBt. The white solid was recrystallized from acetonitrile-ether, giving pale yellow solid at a yield of 88.9% (7.5 grams).

m.p.: 208-210° C. (decomposed);

$^1$H NMR (CD$_3$COCD$_3$): δ=3.30 (s, 3H, CH$_3$), 3.71 (s, 3H, CH$_3$), 3.75-4.02 (m, 4H, 2CH$_2$), 4.11-4.16 (m, 4H, 2CH$_2$), 7.86-7.89 (dd, 1H, ar), 8.58-8.61 (dd, 1H, ar), 9.09-9.11 (dd, 1H, ar) ppm;

$^{13}$C NMR (CD$_3$COCD$_3$): δ=42.09, 42.52, 50.66, 51.78, 66.14, 123.25, 126.34, 155.36 ppm.

Preparation of 1-((dimethylimino)(morpholino)methyl)3-H-6-trifluoromethylbenzo[1,2,3]-triazolo-1-ium-3-olate hexafluorophosphate (6-CF$_3$HDMB or 6-HDMFB)

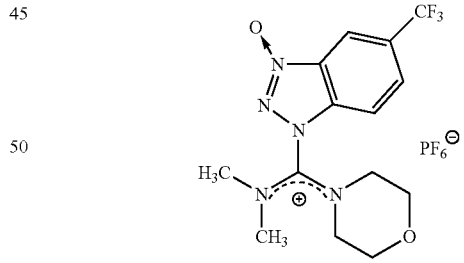

6-CF$_3$HDMB was prepared according to the method described hereinabove for the preparation of HDMB, using 6-CF$_3$-HOBt instead of HOBt. The product was obtained at 81.5% yield.

m.p.: 194-195° C.;

$^1$H NMR (CD$_3$COCD$_3$): δ=3.34 (s, 3H, CH$_3$), 3.72 (s, 3H, CH$_3$), 3.95-3.961 (m, 4H, 2CH$_2$), 4.08-4.15 (m, 4H, 2CH$_2$), 8.24-8.27 (qd, 2H, ar), 8.43 (t, 1H, ar) ppm;

$^{13}$C NMR (CD$_3$COCD$_3$): δ=41.84, 42.42, 50.88, 51.66, 66.21, 66.35, 114.45, 116.35, 129.9, 150.47 ppm.

Preparation of 1-((dimethylamino)(morpholino))pyrrolidine-2,5-dione metheniminium hexafluorophosphate (HDMS)

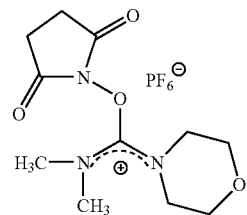

HDMS was prepared according to the method described hereinabove for the preparation of HDMB, using N-hydroxy succinimide (NHS) instead of HOBt. The white solid was recrystallized from acetonitrile-ether to give the product 78% yield.

m.p.: 192-194° C.;
$^1$H NMR (CD$_3$COCD$_3$): δ=3.03 (s, 4H, 2CH$_2$), 3.35 (s, 6H, 2CH$_3$), 3.82-3.85 (m, 8H, 4CH$_2$) ppm;
$^{13}$C NMR (CD$_3$COCD$_3$): δ=25.88, 49.42, 65.78, 161.5, 170.16 ppm.

Preparation of 1-((dimethylamino)(morpholino))oxypentafluorophenyl metheniminium hexafluoro phosphate (HDMPfp)

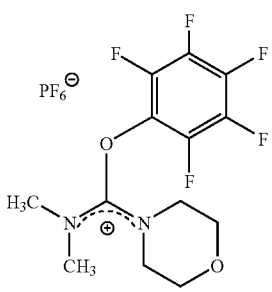 [SMILES: "PF6" ; CN(C)C(Oc1c(F)c(F)c(F)c(F)c1F)N1CCOCC1]

HDMPfp was prepared according to the method described hereinabove for the preparation of HDMB, using pentafluorophenol (Pfp-OH) instead of HOBt. The product was obtained at 91% yield.

m.p.: 202-203° C.;
$^1$H NMR (CD$_3$COCD$_3$): δ=3.38 (s, 6H, CH$_3$), 3.80-3.83 (m, 4H, CH$_2$), 3.86-3.89 (m, 4H, 2CH$_2$) ppm;
$^{13}$C NMR (CD$_3$COCD$_3$): δ=40.58, 49.25, 65.69, 159.72 ppm.

Preparation of Tetramethyl Uronium/Immonium Type Coupling Reagents—General Procedure D The chloroiminium salt, prepared as illustrated in Scheme 4 hereinabove (20 mmol) is added to a solution of the potassium salt of the leaving group hydroxyl-precursor (denoted KOL$_1$ in Scheme 17, 20 mmol) in acetonitrile (50 ml) at 0° C. The reaction mixture is stirred at this temperature for 30 minutes and allowed to warm to room temperature while stirring for 6 hours. The resulting precipitate is filtered and washed with acetonitrile, the solvent is concentrated to small volume (1/4) under reduced pressure, and then dry ether is added to afford the product typically as a white solid in pure state.

Scheme 17

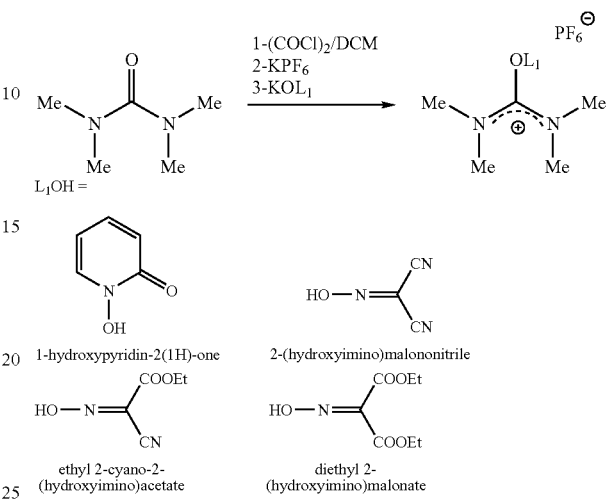

Preparation of 1,1,3,3-tetramethyl-2-(2-oxopyridin-1(2H)-yl)isouronium hexafluorophosphate (HTOP)

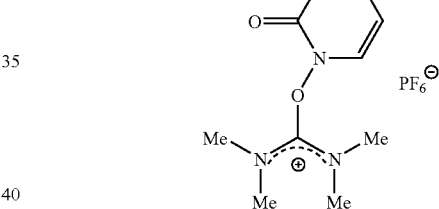

1,1,3,3-tetramethyl-2-(2-oxopyridin-1(2H)-yl)isouronium hexafluorophosphate (HTOP) was prepared according to General Procedure D, and obtained as a white solid at a yield of 85.6% (6.08 grams).

m.p. 204-205° C.;
$^1$H NMR (acetone-d$_6$): δ=3.12 (s, 12H, 4 CH$_3$), 6.49 (d, 1H), 6.74 (dd, 1H), 7.63 (td, 1H), 8.42 (dd, 1H) ppm;
$^{13}$C NMR (acetone-d$_6$): δ=40.76, 107.11, 122.05, 135.98, 142.14, 156.66, 162.22 ppm.

Preparation of O-[Cyano(ethoxycarbonyl)methylidene)amino]-1,1,3,3-tetramethyluronium Hexafluorophosphate (HTOCC)

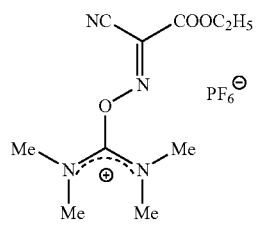

O-[Cyano(ethoxycarbonyl)methylidene)amino]-1,1,3,3-tetramethyluronium hexafluorophosphate was prepared according to General Procedure D, and obtained as a white solid at a yield of 82.1% (6.32 grams).

m.p. 135-137° C. (decomposed);

$^1$H NMR (acetone-$d_6$): δ=1.37 (1, 3H, CH$_3$), 3.37 (s, 12H, 4 CH$_3$), 4.82 (q, 2H, CH$_2$) ppm;

$^{13}$C NMR (acetone-$d_6$): δ=13.46, 40.71, 64.56, 106.78, 135.09, 156.11, 161.43 ppm.

Preparation of O-[(dicyanomethylidene)amino]-1,1,3,3-tetramethyluronium hexafluorophosphate (HTODC)

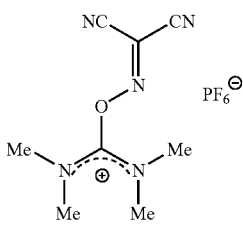

O-[(dicyanomethylidene)amino]-1,1,3,3-tetramethyluronium hexafluorophosphate (HTODC) was prepared according to General Procedure D, and obtained as a white solid at a yield of 74.0% (5.0 grams).

m.p. 180-181° C. (decomposed);

$^1$H NMR (acetone-d6): δ=3.27 (s, 12H, 4CH3) ppm;

$^{13}$C NMR (acetone-d6): δ=40.80, 105.10, 108.21, 119.65, 160.67 ppm.

Preparation of O-[(diethoxycarbonylmethylidene)amino]-1,1,3,3-tetramethyluronium hexafluorophosphate (HTODeC)

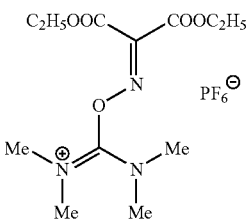

O-[(diethoxycarbonylmethylidene)amino]-1,1,3,3-tetramethyluronium hexafluorophosphate (HTODeC) was prepared according to General Procedure D, and obtained as pale yellow oil at a yield of 84.5%.

$^1$HNMR (CDCl3): δ=1.35 (t, 6H, 2CH$_3$), 3.18 (s, 12H, 4CH$_3$), 4.39-4.48 (q, 4H, 2CH2) ppm.

Preparation of Dimethyl Morpholino Uronium/Immonium Type Coupling Reagents—General Procedure E The preparation of a series of dimethyl morpholino uronium/immonium type coupling reagents is carried out as illustrated in Scheme 18 below.

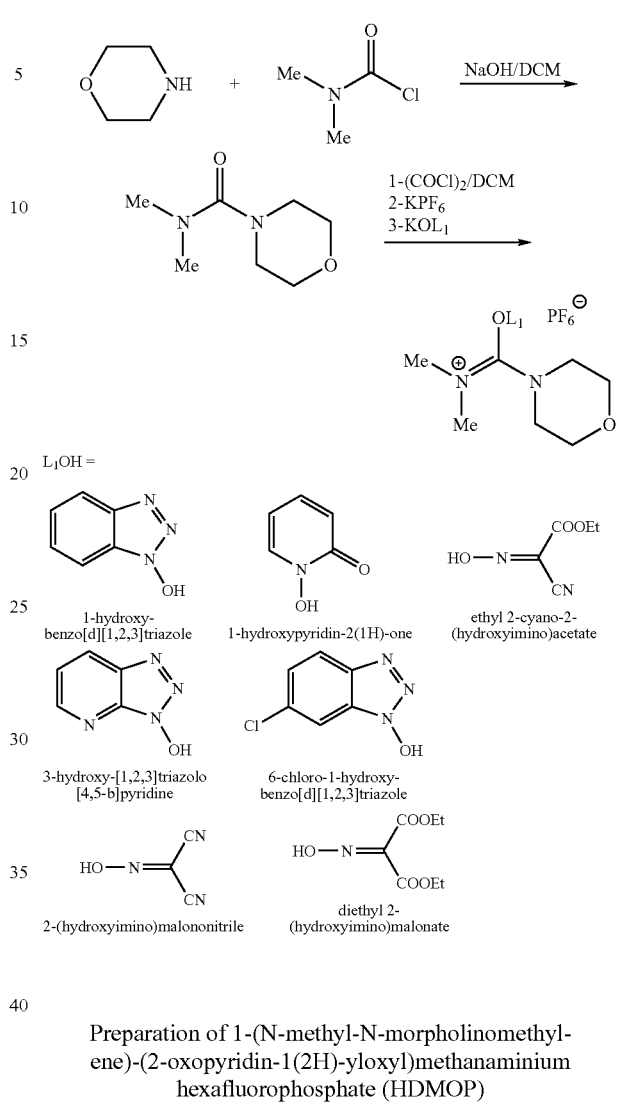

Preparation of 1-(N-methyl-N-morpholinomethylene)-(2-oxopyridin-1(2H)-yloxyl)methanaminium hexafluorophosphate (HDMOP)

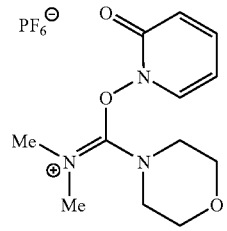

1-(N-methyl-N-morpholinomethylene)-(2-oxopyridin-1(2H)-yloxyl)methanaminium hexafluorophosphate (HDMOP) was prepared according to General Procedure E, and obtained as a white solid at a yield of 78.1% (6.2 grams).

$^1$H NMR (acetone-$d_6$): δ=3.21 (s, 6H, 2CH$_3$), 3.51 (brs, 4H, 2CH$_2$), 3.61-3.64 (m, 4H, 2CH$_2$), 6.44 (td, 1H), 6.71 (dd, 1H), 7.58 (td, 1H), 8.13 (dd, 1H) ppm;

$^{13}$C NMR (acetone-$d_6$): δ=49.33, 65.47, 106.98, 122.22, 134.98, 141.73, 156.94, 162.06 ppm.

Preparation of 1-[(1-(Cyano-2-ethoxy-2-oxoethylideneaminooxy)-dimethylamino-morpholinomethylene)]methanaminium hexafluorophosphate (HDMOCC)

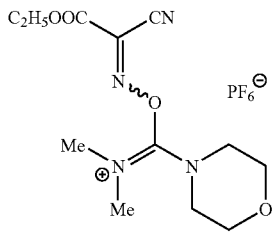

1-[(1-(Cyano-2-ethoxy-2-oxoethylideneaminooxy)-dimethylamino-morpholinomethylene)]methanaminium hexafluorophosphate (HDMOCC) was prepared according to General Procedure E, and obtained as white crystals at a yield of 88.8% (7.6 grams).

m.p. 143-144° C.;
$^1$HNMR (acetone-$d_6$): δ=1.38 (t, 3H, $CH_3$), 3.41 (s, 6H, $2CH_3$), 3.82 (t, 4H, $2CH_2$), 3.89 (t, 4H, $2CH_2$), 4.48 (q, 2H, $CH_2$) ppm;
$^{13}$C NMR (acetone-$d_6$): δ=13.48, 40.70, 49.94, 64.59, 66.04, 106.76, 135.03, 156.14, 160.61 ppm.

Preparation of 1-[(1-(dicyanomethyleneaminooxy)-dimethylamino-morpholinomethylene)]methanaminium hexafluorophosphate (HDMODC)

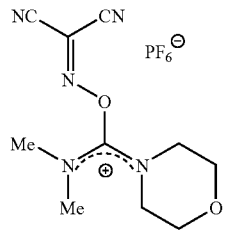

1-[(1-(dicyanomethyleneaminooxy)-dimethylamino-morpholinomethylene)]methanaminium hexafluorophosphate (HDMODC) was prepared according to General Procedure E, and obtained as white solid at a yield of 74.8% (5.7 grams).

m.p. 118-119° C.;
$^1$HNMR (acetone-$d_6$): δ=3.42 (s, 6H, $2CH_3$), 3.80-3.88 (m, 8H, $4CH_2$) ppm;
$^{13}$C NMR (acetone-$d_6$): δ=40.97, 49.93, 65.92, 105.13, 108.15, 119.84, 159.77 ppm.

Preparation of 1-[(1,3-diethyoxy-1,3-dioxopropan-2-ylideneaminooxy)-dimethylamino-morpholinomethylene)]methanaminium hexafluorophosphate (HDMODeC)

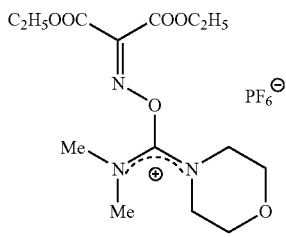

1-[(1,3-diethyoxy-1,3-dioxopropan-2-ylideneaminooxy)-dimethylamino-morpholinomethylene)]methanaminium hexafluorophosphate (HDMODeC) was prepared according to General Procedure E, and obtained as pale yellow oil at a yield of 84.3%.

$^1$HNMR (CDCl$_3$): δ=1.35 (t, 6H, $2 CH_3$), 3.21 (s, 6H, $2 CH_3$), 3.35 (t, 2H, CH2), 3.61 (t, 2H, CH2), 3.78 (t, 2H, CH2), 3.87 (t, 2H, CH2), 4.37-4.50 (q, 4H, $2CH_2$) ppm.

Preparation of Dimethyl Pyrrolidino Uronium/Immonium Type Coupling Reagents—General Procedure F The preparation of a series of dimethyl pyrrolidino uronium/immonium type coupling reagents is carried out as illustrated in Scheme 19 below using the same type of leaving group moieties (OL$_1$) as shown in Scheme 17 and Scheme 18 above.

Scheme 19

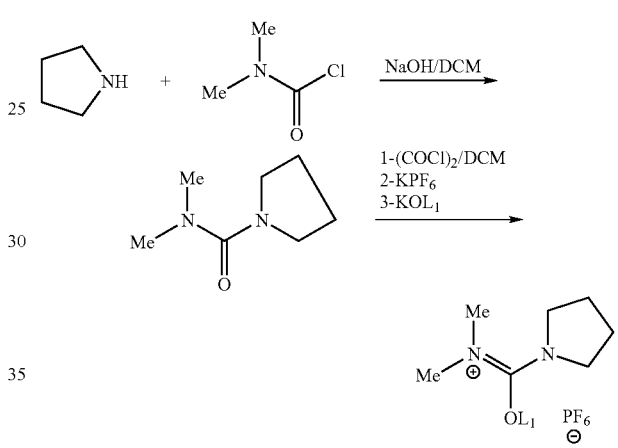

Preparation of 6-chloro-1-((dimethylamino)(pyrrolidinium-1-ylidene)methyl)-1H benzo[d][1,2,3]triazole 3-oxide hexafluorophosphate (6-Cl-HDmPyB)

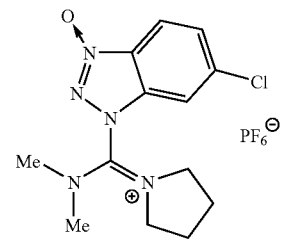

6-Chloro-1-((dimethylamino)(pyrrolidinium-1-ylidene)methyl)-1H benzo[d][1,2,3]triazole 3-oxide hexafluorophosphate (6-Cl-HDmPyB) was prepared according to General Procedure F, and obtained as white solid at a yield of 88.6% (7.8 grams).

m.p. 192-193° C.;
$^1$HNMR (acetone-$d_6$): δ=1.98 (bs, 3H, $CH_3$), 2.14 (brs, 3H, $CH_3$), 2.70 (t, 4H, $2CH_2$), 4.10 (t, 4H, $2CH_2$), 7.83-7.84 (m, 2H, ar), 7.99 (q, 1H, ar) ppm;
$^{13}$C NMR (acetone-$d_6$): δ=24.52, 26.02, 41.60, 52.83, 115.76, 132.50, 132.59, 134.06, 137.34, 148.32 ppm.

Preparation of 1-((dimethylamino)(2-oxopyridin-1(2H)-yloxy)methylene)pyrrolidinium hexafluorophosphate (HDmPyOP)

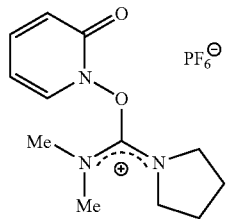

1-((Dimethylamino)(2-oxopyridin-1(2H)-yloxy)methylene)pyrrolidinium hexafluorophosphate (HDmPyOP) was prepared according to General Procedure F, and obtained as white solid at a yield of 6.6 g (86.7%).

m.p. 146-147° C. (decomposed).
¹HNMR (acetone-d₆): δ=1.98-2.15 (m, 4H, 2CH₂), 3.06 (s, 6H, 2CH₃), 3.71-3.80 (m, 4H, 2CH₂), 6.41 (td, 1H), 6.73 (dd, 1H), 7.50 (td, 1H), 7.94 (dd, 1H) ppm;
¹³C NMR (acetone-d₆): δ=25.16, 39.77, 51.25, 106.70, 122.04, 135.40, 156.73, 159.84 ppm.

Preparation of 1-[(1-(Cyano-2-ethoxy-2-oxoethylideneaminooxy)-dimethylamino-pyrrolodinomethylene)]methanaminium hexafluorophosphate (HDmPyOCC)

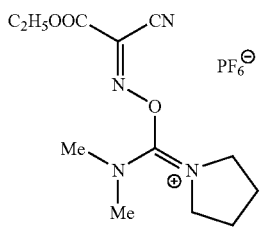

1-[(1-(Cyano-2-ethoxy-2-oxo ethylideneamino oxy)-dimethylamino-pyrrolodinomethylene)]methanaminium hexafluorophosphate (HDmPyOCC) was prepared according to General Procedure F, and obtained as white solid at a yield of 82.7% (6.8 grams).

m.p. 126-127° C. (decomposed);
¹HNMR (acetone-d₆): δ=1.37 (t, 3H, CH₃), 2.10, 2.13 (m, 4H, 2CH₂), 3.36 (s, 6H, 2CH₃), 3.95-3.99 (m, 4H, 2CH₂), 4.48 (q, 2H, CH₂) ppm;
¹³C NMR (acetone-d₆): δ=13.47, 25.09, 40.40, 51.58, 64.52, 106.74, 134.82, 156.12, 158.66 ppm.

Preparation of 1-[(1-(dicyanomethylideneaminooxy)-dimethylamino-pyrrolodinomethylene)]methanaminium hexafluorophosphate (HDmPyODC)

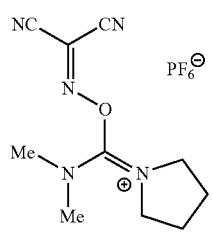

1-[(1-(dicyanomethylideneaminooxy)-dimethylamino-pyrrolodinomethylene)]methanaminium hexafluorophosphate (HDmPyODC) was prepared according to General Procedure F, and obtained as a light yellow solid at a yield of 74% (5.4 grams).

m.p. 146-147° C. (decomposed);
¹HNMR (acetone-d₆): δ=1.97-2.00 (m, 4H, 2CH₂), 3.28 (s, 6H, 2CH₃), 3.96-4.04 (m, 4H, 2CH₂) ppm;
¹³C NMR (acetone-d₆): δ=25.07, 40.41, 51.77, 105.06, 108.23, 119.30, 157.86 ppm.

Preparation of Pyrrolidino Porpholino Uronium/Immonium Type Coupling Reagents—General Procedure G The preparation of a series of dimethyl pyrrolidino uronium/immonium type coupling reagents is carried out as illustrated in Scheme 20 below using the same type of leaving group moieties (OL1) as shown in Scheme 18 above.

Scheme 20

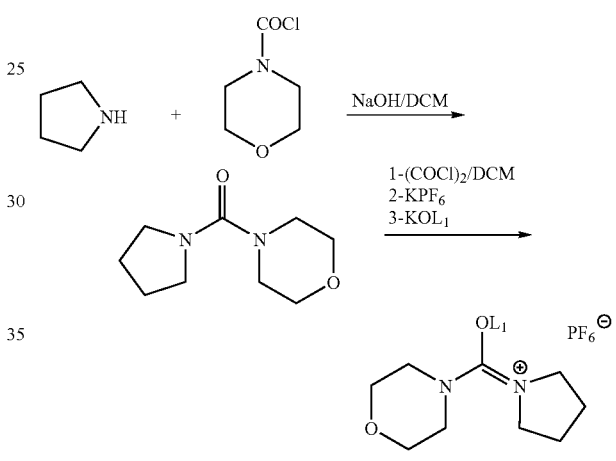

Preparation of 1-(morpholino(pyrrolidinium-1-ylidene)methyl)-1H-benzo[d][1,2,3]triazole 3-oxide hexafluorophosphate (HMPyB)

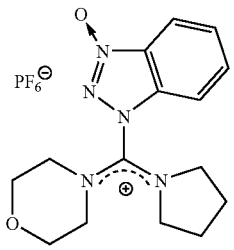 [SMILES: "PF6" ; [O-][n+]1nn(C(N2CCCC2)N2CCOCC2)c2ccccc21]

1-(morpholino(pyrrolidinium-1-ylidene)methyl)-1H-benzo[d][1,2,3]triazole 3-oxide hexafluorophosphate (HMPyB) was prepared according to General Procedure G, and obtained as white solid at a yield of 82.8% (7.4 grams).

mp 203-204° C. (decomposed);
¹HNMR (acetone-d₆): δ=2.12-2.15 (m, 2H, CH₂), 2.16-2.29 (m, 2H, CH₂), 3.42-3.58 (m, 2H, CH₂), 3.80-4.26 (m, 10H, 5CH₂), 7.75 (td, 1H), 7.97-8.02 (m, 2H), 8.07 (d, 1H) ppm;
¹³C NMR (acetone-d₆): δ=25.09, 41.76, 42.23, 50.81, 51.51, 66.19, 66.41, 109.99, 114.56, 127.52, 143.54 ppm.

Preparation of 1-(morpholino(pyrrolidinium-1-ylidene)methyl)-1H-[1,2,3]triazolo[4,5-I]pyridine 3-oxide hexafluorophosphate (HMPyA)

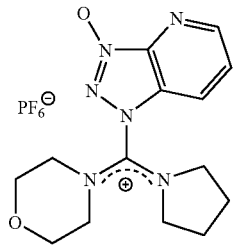

1-(morpholino(pyrrolidinium-1-ylidene)methyl)-1H-[1,2,3]triazolo[4,5-I]pyridine 3-oxide hexafluorophosphate (HMPyA) was prepared according to General Procedure G, and obtained as white solid at a yield of 81.3% (7.3 grams).
mp 206-208° C. (decomposed);
$^1$HNMR (acetone-d$_6$): δ=2.11-2.15 (m, 2H, CH$_2$), 2.18-2.30 (m, 2H, CH$_2$), 3.48-3.63 (m, 2H, CH$_2$), 3.79-4.16 (m, 10H, 5CH$_2$), 8.02 (dd, 1H), 8.53 (dd, 1H), 8.85 (dd, 1H) ppm;
$^{13}$C NMR (acetone-d$_6$): δ=25.09, 41.74, 42.35, 50.82, 51.58, 66.19, 66.42, 124.37, 127.84, 149.65 ppm.

Preparation of 5-chloro-1-(morpholino(pyrrolidinium-1-ylidene)methyl)-1H-benzo[d][1,2,3]-triazole 3-oxide hexafluorophosphate (6-HMPyCB)

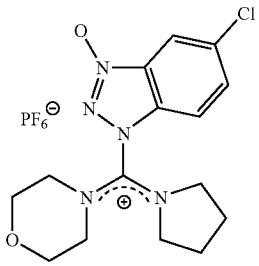

5-chloro-1-(morpholino(pyrrolidinium-1-ylidene)methyl)-1H-benzo[d][1,2,3]triazole 3-oxide hexafluorophosphate (6-HMPyCB) was prepared according to General Procedure G, and obtained as white solid at a yield of 82.7% (7.96 grams).
m.p. 217-218° C. (decomposed);
$^1$HNMR (acetone-d$_6$): δ=2.10-2.15 (m, 2H, CH$_2$), 2.19-2.29 (m, 2H, CH$_2$), 3.45-3.65 (m, 2H, CH$_2$), 3.81-4.09 (m, 10H, 5CH$_2$), 7.99 (d, 1H), 8.02 (d, 1H), 8.12 (dd, 1H) ppm;
$^{13}$C NMR (acetone-d$_6$): δ=25.93, 52.89, 53.36, 66.09, 66.42, 115.79, 115.84, 132.57, 132.62, 134.06, 134.12, 147.38 ppm.

Preparation of 1-(morpholino(2-oxopyridin-1(2H)-yloxy)methylene)pyrrolidinium hexafluorophosphate (HMPyOP)

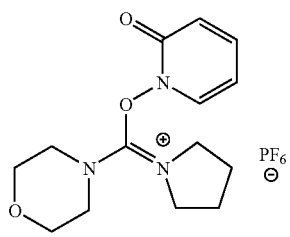

1-(morpholino(2-oxopyridin-1(2H)-yloxy)methylene) pyrrolidinium hexafluorophosphate (HMPyOP) was prepared according to General Procedure G, and obtained as white solid at a yield of 70% (5.9 grams).
m.p. 145-146° C. (decomposed);
$^1$HNMR (acetone-d$_6$): δ=2.05-2.13 (m, 4H, 2CH$_2$), 3.54 (t, 4H, 2CH$_2$), 3.65 (t, 4H, 2CH$_2$), 3.94-3.98 (m, 4H, 2CH$_2$), 6.85 (dd, 1H), 7.72 (td, 1H), 8.21 (dd, 1H) ppm;
$^{13}$C NMR (acetone-d$_6$): δ=25.16, 39.77, 51.25, 52.87, 106.70, 122.04, 135.44, 156.76, 159.94 ppm.

Preparation of 1-((1-cyano-2-ethoxy-2-oxoethylideneaminooxy)(morpholino)methylene) pyrrolidinium hexafluorophosphate (HMPyOCC)

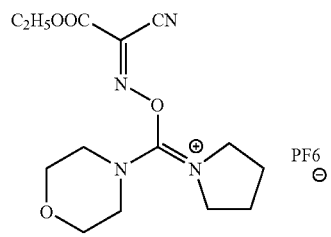

1-((1-Cyano-2-ethoxy-2-oxoethylideneaminooxy)(morpholino)methylene) pyrrolidinium hexafluorophosphate (HMPyOCC) was prepared according to General Procedure G, and obtained as white solid at a yield of 90.3% (8.2 grams).
mp 171-172° C.;
$^1$HNMR (acetone-d$_6$): δ=1.26 (t, 3H, CH$_3$), 1.98-2.02 (m, 4H, 2CH$_2$), 3.65-3.68 (m, 4H, 2CH$_2$), 3.74-3.76 (m, 4H, 2CH$_2$), 3.84-3.87 (m, 4H, 2CH$_2$), 4.37-4.40 (q, 2H, CH$_2$) ppm;
$^{13}$C NMR (acetone-d$_6$): δ=13.49, 25.09, 49.20, 51.57, 55.98, 51.76, 64.54, 66.06, 106.69, 134.63, 156.11, 157.88 ppm.

Preparation of 1-((dicyanomethyleneaminooxy)(morpholino)methylene)pyrrolidinium hexafluorophoate (HMPyODC)

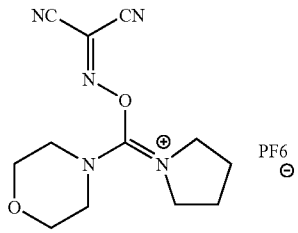

1-((dicyanomethyleneaminooxy)(morpholino)methylene) pyrrolidinium hexafluorophoate (HMPyODC) was prepared according to General Procedure G, and obtained as light yellow solid at a yield of 78.6% (6.4 grams).
m.p. 158-159° C.;
$^1$HNMR (acetone-d$_6$): δ=2.11-2.14 (m, 4H, 2CH$_2$), 3.79.3.85 (m, 4H, 2CH$_2$), 3.86-3.88 (m, 4H, 2CH$_2$), 3.98-4.01 (m, 4H, 2CH$_2$) ppm;
$^{13}$C NMR (acetone-d$_6$): δ=25.28, 49.15, 65.95, 105.07, 108.17, 119.48, 157.00 ppm.

Preparation of ethyl 2-cyano-2-(diphenoxyphosryloxyimino)acetate

The preparation of ethyl 2-cyano-2-(diphenoxyphosryloxyimino)acetate was adapted from a published procedure [F. Hoffmann, L. Jager, C. Criehl, *Phosphorus, sulfur, and silicon*, 178, 299-309 (2003)] and carried out as illustrated in Scheme 21 below.

Scheme 21

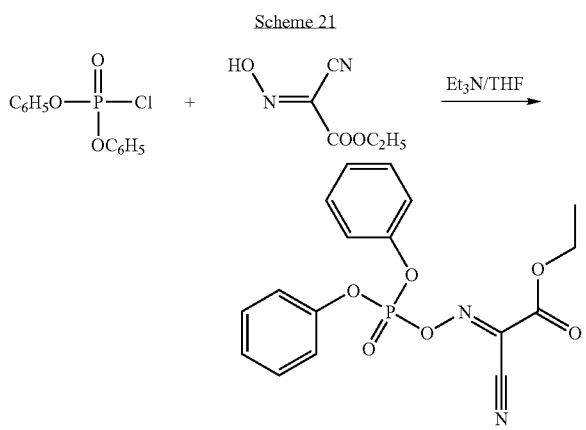

TEA (1.3 ml, 10 mmol) was added under argon atmosphere to a solution of diphenylchlorophosphate (2.69 grams, 10 mmol) and the corresponding additive (10 mmol) in anhydrous THF (50 ml). After 3 hours stirring at room temperature the reaction mixture was filtered off and the solvent was removed under reduced pressure. The resulting oil was washed with n-pentane and dried under vacuum. The product was obtained as oil at a yield of 64.5% (2.42 grams).

$^1$HNMR (CDCl$_3$): δ=1.41 (t, 3H, CH$_3$), 4.47 (q, 2H, CH$_2$), 7.22-7.44 (m, 10H, 2Ph) ppm.

Preparation of 2-Pyridylacetonitrile Oxime Containing Coupling Reagents—General Procedure H The preparation of a series of 2-pyridylacetonitrile oxime containing coupling reagents is carried out as illustrated in Scheme 22 below.

Scheme 22

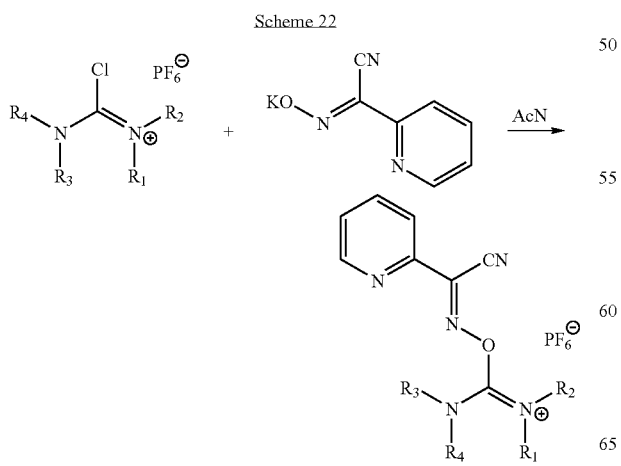

Preparation of N-[(cyano(pyridine-2-yl)methyleneaminooxy)(dimethylamino) methylene)-N-Methylmethanaminium hexafluorophosphate (HTOPC)

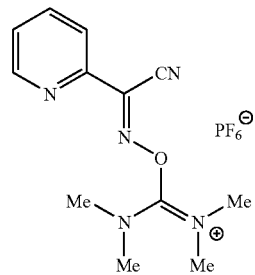

N-[(cyano(pyridine-2-yl)methyleneaminooxy)(dimethylamino) methylene)-N-Methylmethanaminium hexafluorophosphate (HTOPC) was prepared according to General Procedure H, and obtained as a light reddish brown solid at a yield of 82.7% (6.2 grams).

m.p. 169-171° C.;

$^1$HNMR (acetone-d$_6$): δ 3.30 (s, 12H, 4CH$_3$), 7.57-7.61 (m, 1H), 7.94 (td, 1H), 8.10 (dd, 1H), 8.70 (dd, 1H) ppm.

$^{13}$C NMR (acetone-d$_6$): δ 40.48, 107.56, 122.52, 127.87, 138.18, 142.46, 146.67, 150.68, 162.03 ppm.

Preparation of N-[(cyano(pyridine-2-yl)methyleneaminooxy)(dimethylamino) methylene)-N-morpholinomethanaminium hexafluorophosphate (HDMOPC)

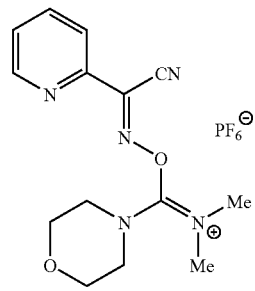

N-[cyano(pyridine-2-yl)methyleneaminooxy)(dimethylamino) methylene)-N-morpholinomethanaminium hexafluorophosphate (HDMOPC) was prepared according to General Procedure H, and obtained as a light brown solid at a yield of 89.4% (7.74 grams).

m.p. 154-155° C.;

$^1$H NMR (acetone-d$_6$): δ=3.34 (s, 12H, 4CH$_3$), 3.79-3.83 (m, 8H, 4 CH$_2$) 7.58-7.62 (m, 1H), 7.96 (td, 1H), 8.12 (dd, 1H), 8.71 (dd, 1H) ppm;

$^{13}$C NMR (acetone-d$_6$): δ 40.76, 49.79, 66.13, 107.60, 122.53, 127.92, 138.23, 142.74, 146.63, 150.69, 161.06 ppm.

Preparation of 4-((dimethylamino)fluoromethylene)morpholin-4-iminium hexafluorophosphate (DFMH)

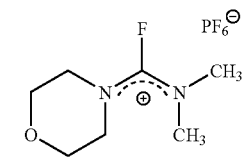

DFMH was obtained by treatment of 4-((dimethyamino)chloromethylene)-morpholin-4-iminium hexafluorophosphate (DCMH), prepared according to General Procedure C described hereinabove and for the preparation of DCMH, with KF in acetonitrile at 90% yield.

m.p.: 92-93° C.;
$^1$H NMR (acetone-d6): δ=3.31 (d, 6H, 2CH$_3$), 3.70-3.81 (m, 4H, 2CH$_2$) 3.84-3.86 (m, 4H, 2CH$_2$) ppm;
$^{13}$C NMR (acetone-d6): δ=39.15, 48.11, 65.57, 157.09 ppm.

Preparation of
4-(chloro(morpholino)methylene)morpholin-4-iminium
Hexafluorophosphate (CMMH)

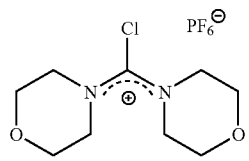

CMMH was prepared according to General Procedure C described hereinabove and for the preparation of DCMH, using dimorpholinomethanone, at a yield of 72.6% (white crystals).

m.p.: 136-137° C.;
$^1$H NMR (CD$_3$COCD$_3$): δ=3.27 (t, 8H, 4CH$_2$), 3.68 (t, 8H, 4CH$_2$) ppm;
$^{13}$C NMR (CD$_3$COCD$_3$): δ=47.44, 66.60, 163.99 ppm.

Preparation of
4-(Fluoro(morpholino)methylene)morpholin-4-iminium
hexafluorophosphate (FMMH)

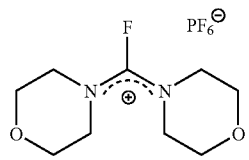

FMMH was obtained by treatment of 4-(chloro(morpholino)methylene) morpholin-4-iminium hexafluorophosphate (CMMH), prepared according to General Procedure C described hereinabove, at 84% yield.

m.p.: 168-170° C.;
$^1$H NMR (acetone-d6): δ=3.21-2.38 (m, 8H, 4CH$_2$), 3.61 (t, 8H, 4CH$_2$) ppm.

Preparation of HDTMA

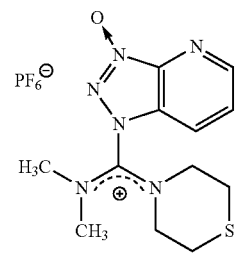 [SMILES: "PF6" ; CN(C)C(N1CCSCC1)n1n[n+]([O-])c2ncccc21]

4-((dimethyamino)chloromethylene)thiomorpholin-4-iminium hexafluoro phosphate (20 mmol) was added to a solution of HOAt (20 mmol, 2.72 grams), and triethylamine (20 mmol) in DCM (50 ml) at 0° C. The reaction mixture was stirred at 0° C. under N$_2$, and thereafter the temperature was allowed to warm up to room temperature overnight. The pale yellow solid was filtered and washed with cooled DCM and recrystallized from acetonitrile-ether to give white crystals at 76% yield.

m.p.: 197-199° C. (decomposed);
$^1$H NMR (CD$_3$COCD$_3$): δ=2.76-2.77 (m, 1H, CH), 2.97-3.01 (dt, 1H, CH), 3.14-3.23 (m, 2H, CH$_2$), 3.56 (s, 3H, CH$_3$), 3.71 (s, 3H, CH$_3$), 3.72-3.73 (dt, 1H, CH), 3.96-4.00 (dt, 1H, CH), 4.11-4.18 (m, 1H, CH), 4.39-4.45 8 (dt, 1H, CH), 8.00-8.03 (dd, 1H, ar), 8.47-8.50 (dd, 1H, ar), 8.84-8.85 (dd, 1H, ar) ppm;
$^{13}$C NMR (CD$_3$COCD$_3$): δ=14.70, 27.02, 38.75, 45.47, 59.72, 120.50, 128.75, 135.17, 140.23, 150.20 ppm.

Preparation of HDTMB

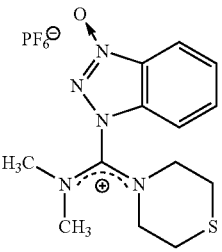

HDTMB was prepared according to the method described hereinabove for the preparation of HDTMA, but using HOBt instead of HOAt. White crystals were obtained by recrystallization from acetonitrile-ether in 80% yield.

m.p. 190-191° C. (decomposed);
$^1$H NMR (CD$_3$COCD$_3$): δ=2.67-2.70 (m, 1H, CH), 2.91-2.96 (m, 1H, CH), 2.97 (s, 3H, CH$_3$), 3.33-3.48 (m, 5H, CH$_2$, CH$_3$), 3.65-3.69 (m, 1H, CH), 3.88-3.95 m, 1H, CH), 4.09-4.12 (m, 1H, CH), 8.00-8.03 (dd, 1H, ar), 7.68-7.72 (td, 1H, ar), 7.86-7.88 (d, 1H, ar), 7.93-7.97 (d, 1H, ar), 8.08 (d, 1H, ar) ppm;
$^{13}$C NMR (CD$_3$COCD$_3$): δ=14.70, 27.28, 40.61, 40.82, 42.82, 43.09, 52.94, 53.17, 115.44, 116.46, 127.94, 133.60, 150.79 ppm.

Example 4

Characterization of the Peptide-Coupling Agents

Effect of Oxygen on the Solubility of the Coupling Agents:

The maximal solubility of various known and novel peptide-coupling agents was tested in DMF in order to assess their capacity to participate in solution- and solid-support peptide forming reactions.

Table 4 presents the name of the tested coupling agent (known or novel), its chemical structure, the mass of agent per volume of DMF and the calculated molarity in DMF.

TABLE 4

| Coupling agent | Chemical structure | Wt/ml | Molarity |
|---|---|---|---|
| HDMOCC (novel) | | 0.620 | 1.44 |
| HDMODC (novel) | 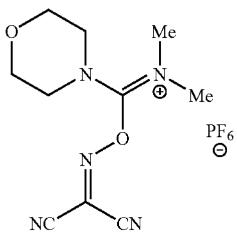 | 0.520 | 1.36 |
| 6-$CF_3$HDMB (novel) | 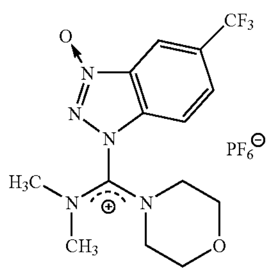 | 0.475 | 1.02 |
| 6-Cl-HDMB (novel) | 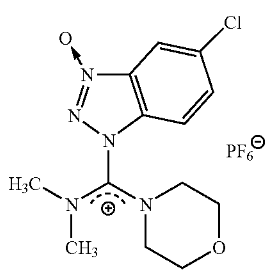 | 0.456 | 1.0 |
| HDMOPC (novel) | 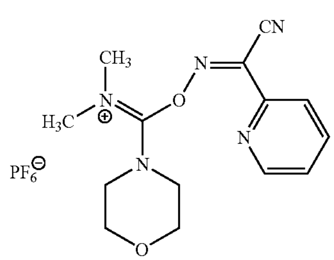 [SMILES: "PF6" ; C[N+](C)=C(O/N=C(/C#N)c1ccccn1)N1CCOCC1] | 0.430 | 0.98 |
| HDMB (novel) | 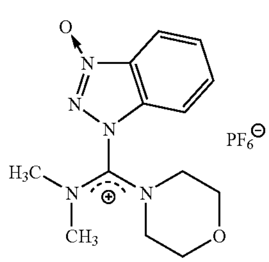 | 0.350 | 0.83 |

TABLE 4-continued

| Coupling agent | Chemical structure | Wt/ml | Molarity |
| --- | --- | --- | --- |
| HDMA (novel) | (structure) | 0.285 | 0.68 |
| 6-Cl-HBTU (known) | (structure) | — | 0.5 |
| HBTU (known) | (structure) | 0.175 | 0.46 |
| HATU (known) | (structure) | 0.165 | 0.43 |

As can be seen in Table 4, the proton acceptor iminium-type coupling agents presented herein are significantly more soluble than their carbon derivatives counterpart.

Solution Synthesis of the Di-Peptide Z-Phg-Pro-NH$_2$:

The aptitude of the novel iminium-type peptide-coupling agents to couple between two amino-acids without causing racemization thereof was tested in solution. Solution coupling of benzyloxycarbonyl (Z)-protected phenylglycine (Z-Phg-OH) with H-Pro-NH$_2$ to give Z-Phg-Pro-NH$_2$ in DMF in the presence of a base and a coupling agent was used to rank the novel and known peptide-coupling agents, and the extent of Phg residue racemization was determined and used as a ranking criteria.

Table 5 presents the name of the coupling agents, the type and amount of base used in the reaction, the yield or the coupling reaction and the racemization caused during the formation of Z-Phg-Pro-NH$_2$ in DMF (solution phase synthesis).

TABLE 5

| Coupling Reagent | Base (equiv.) | Yields (%) | DL (%) |
| --- | --- | --- | --- |
| 6-CF$_3$HDMB (novel) | DIEA (2) | 84.1 | 0.6 |

TABLE 5-continued
| Coupling Reagent | Base (equiv.) | Yields (%) | DL (%) |
|---|---|---|---|
| 6-ClHDMB (novel) | DIEA (2) | 84.5 | 1.5 |
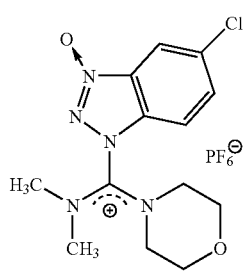
| | | | |
|---|---|---|---|
| HDMA (novel) | DIEA (1) | 82.3 | 1.6 |
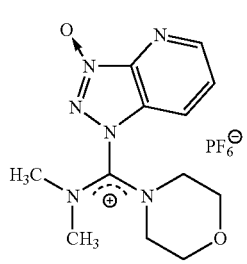
| | | | |
|---|---|---|---|
| HDMA (novel) | DIEA (2) | 81.2 | 1.6 |
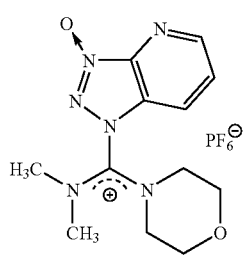
| | | | |
|---|---|---|---|
| HDTMA (novel) | DIEA (2) | 83.0 | 2.1 |
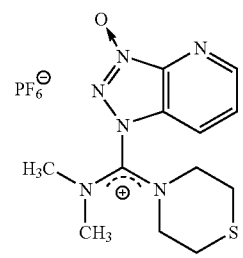
| | | | |
|---|---|---|---|
| HATU (known) | TMP (2) | 77.9 | 2.1 |
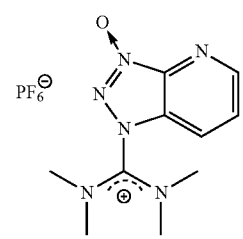
TABLE 5-continued
| Coupling Reagent | Base (equiv.) | Yields (%) | DL (%) |
|---|---|---|---|
| HATU (known) | DIEA (1) | 74.8 | 2.4 |
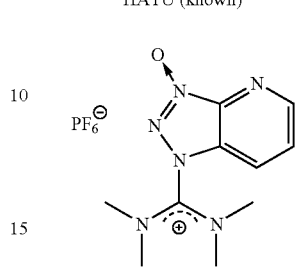
| | | | |
|---|---|---|---|
| HDMB (novel) | DIEA (1) | 82.3 | 3.1 |
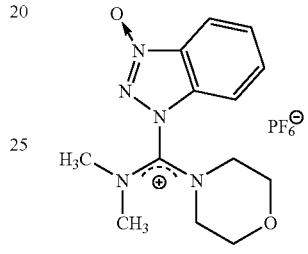
| | | | |
|---|---|---|---|
| HATU (known) | DIEA (2) | 78.4 | 3.1 |
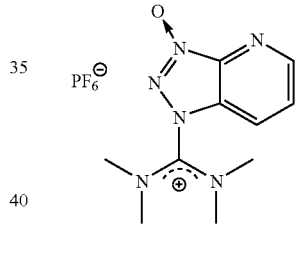
| | | | |
|---|---|---|---|
| HDTMB (novel) | DIEA (2) | 81.3 | 3.5 |
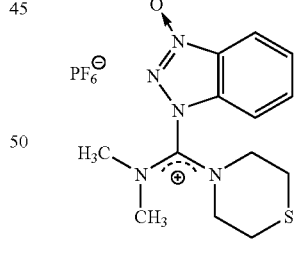
| | | | |
|---|---|---|---|
| HDMB (novel) | DIEA (2) | 80.8 | 3.8 |
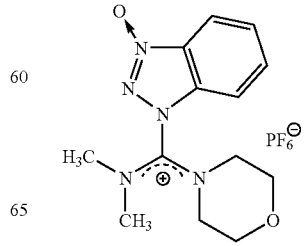

TABLE 5-continued

| Coupling Reagent | Base (equiv.) | Yields (%) | DL (%) |
| --- | --- | --- | --- |
| HDMA (novel) | TMP (2) | 80.3 | 3.9 |
| DFMH (novel) | DIEA (2) (no preactivation) | 82.6 | 4.9 |
| HBTU (known) | DIEA (1) | 75.0 | 5.3 |
| HBTU (known) | TMP (2) | 81.2 | 6.4 |
| DCMH (novel) | DIEA (2) (no preactivation) | 81.9 | 6.9 |
| TFFH (known) | DIEA (2) (no preactivation) | 80.1 | 7.1 |
| HDMB (novel) | TMP (2) | 79.9 | 7.8 |
| HBTU (known) | DIEA (2) | 80.2 | 8.2 |
| TCFH (known) | DIEA (2) (no preactivation) | 80.0 | 29.9 |
| HDMOCC (novel) | DIEA (2) | 88.2 | 0.12 |
| HDMOCC (novel) | TMP (2) | 91.0 | 0.90 |

TABLE 5-continued

| Coupling Reagent | Base (equiv.) | Yields (%) | DL (%) |
|---|---|---|---|
| HDMOCC (novel) 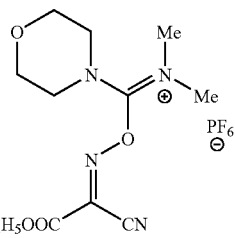 | TMP (1) | 93.0 | 0.40 |
| HMPyOCC (novel) 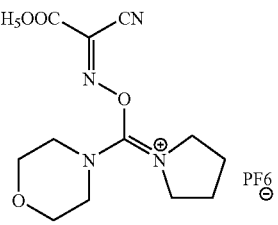 | DIEA (2) | 89.8 | 0.32 |
| HDMODC (novel) 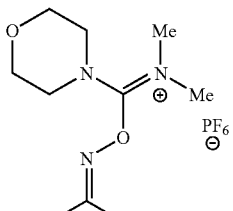 | DIEA (2) | 90.1 | 0.40 |
| HMPyODC (novel) 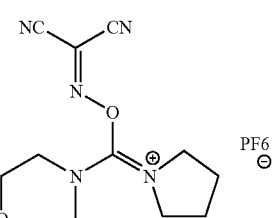 | DIEA (2) | 90.2 | 0.35 |

DIEA = Diisopropylethylamine; and TMP = 2,4,6-trimethylpyridine (collidine).

As can be seen in Table 5, the novel proton acceptor iminium-type coupling agents presented herein cause less racemization than their carbon counterpart derivatives while being more effective in their peptide-bond formation ability. For example, the derivatives of 6-Cl-HOBt, 6-$CF_3$-HOBt, and HONCC were significantly more effective in reducing racemization than the analogous HOAt coupling agents while at the same time affording better yields. These results show clearly that the novel coupling agents presented herein are superior to their presently known counterparts.

The results presented in Table 5 above highlight the profound effect caused by the presence of a proton acceptor in the iminium moiety of the coupling agent, as compared to similar known coupling agents differing from the novel ones only by that structural feature. Hence, the results should be regarded as comparing pairs of coupling agents, a novel agent versus a known counterpart:

HDMA (novel)/HDTMA (novel) versus HATU (known);
HDMB (novel)/HDTMB (novel) versus HBTU (known);
6-Cl-HDMB (novel) versus 6-Cl-HBTU (known);
DFMH (novel) versus TFFH (known); and
DCMH (novel) versus TCFH (known).

The striking superiority of the coupling agents presented herein over the presently known coupling agents is expressed by isolating and comparing these results.

TABLE 5A

| Coupling Reagent | Base (equiv.) | Yields (%) | DL (%) |
|---|---|---|---|
| HDMB | DIEA (2) | 80.8 | 3.8 |
| | TMP (2) | 79.9 | 7.8 |
| | DIEA (1) | 82.3 | 3.1 |
| HDTMB | DIEA (2) | 81.3 | 3.5 |
| HBTU | DIEA (2) | 80.2 | 8.2 |
| | TMP (2) | 81.2 | 6.4 |
| | DIEA (1) | 75.0 | 5.3 |
| HDMA | DIEA (2) | 81.2 | 1.6 |
| | TMP (2) | 80.3 | 3.9 |
| | DIEA (1) | 82.3 | 1.6 |
| HDTMA | DIEA (2) | 83.0 | 2.1 |
| HATU | DIEA (2) | 78.4 | 3.1 |
| | TMP (2) | 77.9 | 2.1 |
| | DIEA (1) | 74.8 | 2.4 |
| HDMOCC | DIEA (2) | 88.2 | 0.12 |
| | TMP (2) | 91.0 | 0.90 |
| HDMODC | DIEA(2) | 90.1 | 0.40 |

The results presented in Table 5A isolate and compare HDMB and HDTMB to HBTU, and HDMA and HDTMA to HATU, and shows clearly the beneficial effect of the morpholine (HDMB and HDMA) or thiomorpholine groups (HDTMA and HDTMB) versus the dimethyl groups (HBTU and HATU) on racemization suppression and yields, when using diisopropylethylamine as a base in the coupling reaction.

This effect is even more profound when considering the coupling agents DCMH and DFMH (novel) versus TCFH and TFFH (known).

TABLE 5B

| Coupling Reagent | Base (equiv.) | Yields (%) | DL (%) |
|---|---|---|---|
| DCMH | DIEA (2) (no preactivation) | 81.9 | 6.9 |
| TCFH | DIEA (2) (no preactivation) | 80.0 | 29.9 |
| DFMH | DIEA (2) (no preactivation) | 82.6 | 4.9 |
| TFFH | DIEA (2) (no preactivation) | 80.1 | 7.1 |

The results presented in Table 5β isolate and compare DCMH to TCFH, and DFMH to TFFH, and shows clearly the beneficial effect of the morpholine (DCMH and DFMH) versus the dimethyl (TCFH and TFFH) on racemization suppression and yields.

Solution Synthesis of the Tri-Peptide Z-Phe-Val-Pro-$NH_2$:

The ability of the novel iminium-type peptide-coupling agents to elongate a di-peptide with a third residue was tested in a solution phase coupling reaction in DMF of Z-Phe-Val-OH with H-Pro-$NH_2$ in the presence of a base which yields the tri-peptide Z-Phe-Val-Pro-$NH_2$. The extent of the racemization of the valine residue was determined and used as ranking criteria.

Table 6 presents the name of the coupling agents, the type and amount of base used in the reaction, the yield or the coupling reaction and the racemization caused during the formation of Z-Phe-Val-Pro-NH$_2$ (2+1) in DMF (solution phase synthesis).

TABLE 6

| Coupling Reagent | Base (equiv.) | Yield (%) | LDL (%) |
|---|---|---|---|
| HDMA (novel) | TMP (2) | 86.2 | 3.7 |
| HDMA (novel) | TMP (1) | 84.1 | 3.8 |
| HATU (known) | TMP (1) | 76.1 | 4.9 |
| HDMA (novel) | DIEA (1) | 87.4 | 5.1 |
| HATU (known) | TMP (2) | 78.0 | 5.3 |
| HDMA (novel) | DIEA (2) | 89.3 | 10.5 |
| HDMB (novel) | TMP (1) | 80.1 | 10.5 |
| HATU (known) | DIEA (1) | 83.2 | 11.0 |
| HDMB (novel) | DIEA (1) | 86.3 | 11.5 |
| HDMB (novel) | TMP (2) | 87.1 | 13.3 |
| HATU (known) | DIEA (2) | 85.8 | 13.9 |
| 6-Cl-HDMB (novel) | DIEA (1) | 79.9 | 13.9 |
| HBTU (known) | TMP (2) | 81.2 | 14.2 |
| HBTU (known) | DIEA (1) | 78.6 | 16.3 |
| HDMB (novel) | DIEA (2) | 88.7 | 20.3 |
| HBTU (known) | DIEA (2) | 89.7 | 27.7 |
| HDMOCC (novel) | TMP (2) | 89.8 | 8.0 |
| HDMOCC (novel) | TMP (1) | 90.3 | 3.5 |
| HDmPyOCC (novel) | TMP (2) | 88.0 | 7.9 |
| HMPyOCC | TMP (2) | 91.0 | 10.2 |

DIEA = Diisopropylethylamine; and
TMP = 2,4,6-trimethylpyridine (collidine).

As can be seen in Table 6, the novel proton acceptor immonium-type coupling agents presented herein cause much less racemization than their carbon counterparts while being at least as effective in their peptide-bond formation capacity.

The striking superiority of the coupling agents presented herein having a proton acceptor, over the presently known coupling agents, not having a proton acceptor but otherwise identical, is brought forth by isolating and comparing these results.

TABLE 6A

| Coupling Reagent | Base (equiv.) | Yield (%) | LDL (%) |
|---|---|---|---|
| HDMA | DIEA (2) | 89.3 | 10.5 |
|  | DIEA (1) | 87.4 | 5.1 |
|  | TMP (2) | 86.2 | 3.7 |
|  | TMP (1) | 84.1 | 3.8 |
| HATU | DIEA (2) | 85.8 | 13.9 |
|  | DIEA (1) | 83.2 | 11.0 |
|  | TMP (2) | 78.0 | 5.3 |
|  | TMP (1) | 76.1 | 4.9 |
| HDMB | DIEA (2) | 88.7 | 20.3 |
|  | DIEA (1) | 86.3 | 11.5 |
|  | TMP (2) | 87.1 | 13.3 |
|  | TMP (1) | 80.1 | 10.5 |
| HBTU | DIEA (2) | 89.7 | 27.7 |
|  | DIEA (1) | 78.6 | 16.3 |
|  | TMP (2) | 81.2 | 14.2 |
| HDMOCC | DIEA (2) | 91.3 | 19.3 |
|  | TMP (2) | 89.8 | 7.0 |
|  | TMP (2) | 90.3 | 3.5 |

The results presented in Table 6A isolate and compare HDMB to HBTU, and HDMA to HATU, and shows clearly the beneficial effect of the morpholine groups (HDMB and HDMA) versus the dimethyl groups (HBTU and HATU) on racemization suppression and yields. As can be seen, the oxime derivative, HDMOCC, is favorable when compared with the HOBt derivatives.

Synthesis of the Pentapeptide H-Tyr-Gly-Gly-Phe-Leu-NH$_2$:

The penta-peptide H-Tyr-Gly-Gly-Phe-Leu-NH$_2$ was prepared by solution phase synthesis using the novel peptide-coupling agent HDMB and Boc-protected amino acids (except the last one, Fmoc-Tyr(OtBu)-OH). At the end of the reaction the Fmoc-group was removed by using 30% diethylamine in acetonitrile for 1 hour and the crude peptide was treated with TFA-DCM (1:1) for two hours at room temperature.

FIG. 2 presents the HPLC chromatogram obtained for the penta-peptide Tyr-Gly-Gly-Phe-Leu-NH$_2$. As can be seen in FIG. 2, excellent product purity of the final product was obtained using HDMB as coupling agent.

Synthesis of Tyr-Aib-Aib-Phe-Leu-NH$_2$ in Solid Phase

The peptide Tyr-Aib-Aib-Phe-Leu-NH$_2$, which contains the challenging coupling one α-aminoisobutyric acid residue to another (Aib-Aib), was synthesized on solid-phase using Fmoc protected amino-acids in the presence of the base DIEA (2 equivalents). The extent of failure to form the Aib-Aib peptide bond, namely the rate of (Tyr-Aib-Aib-Phe-Leu-NH$_2$) penta-peptide versus (Tyr-Aib-Phe-Leu-NH$_2$) tetrapeptide formation during the solid-phase assembly of the penta-peptide was used to assess the effectiveness of the coupling agents.

Table 7 presents the name of the coupling agents, the percent of penta-peptide from the total crude product and the percent of tetra-peptide from the total crude product.

TABLE 7

| Coupling Reagent | Pentapeptide (%) | Tetrapeptide (%) |
|---|---|---|
| 6-Cl-HDMB (novel) | 98.7 | 1.3 |
| HDMA (novel) | 98 | <1 |
| HDMB (novel) | 89 | 10 |
| HATU (known) | 83 | 17 |
| HBTU (known) | 47 | 53 |

As can be seen in Table 7, the novel proton acceptor iminium-type coupling agents were significantly more effective than their carbon counterpart for the solid-phase synthesis of peptides containing the challenging stereo-hindered couplings reaction. The pentapeptide yields were consistently higher than those obtained with the known coupling agents.

Synthesis of the 15-mer of the (60-74) Fragment of the Acyl Carrier Protein (ACP):

The peptide H-Glu-Lys-Ile-Thr-Thr-Val-Gln-Ala-Ala-Ile-Asp-Tyr-Ile-Asn-Gly-NH$_2$ (15-mer peptide) was elongated manually on an Fmoc-Rink Amide-AM-resin using Fmoc-protected amino acids. Coupling times was 30 minutes, excesses of reagents were 3 equivalents, and the excesses of the base DIEA was 6 equivalents.

Table 8 presents the purity of the resulting peptide as determined by reverse-phase HPLC analysis.

TABLE 8

| Coupling Reagent | 15-mer peptide (%) |
|---|---|
| HDMA (novel) | 63.6 |
| 6-Cl-HDMB (novel) | 62.9 |
| HDMB (novel) | 61.6 |
| HBTU (known) | 48.3 |
| HATU (known) | 44.5 |
| HDMOCC (novel) | 79.4 |

As can be seen in Table 8, the novel proton acceptor iminium-type coupling reagents were noticeably superior to their carbon counterparts for the solid-phase synthesis of the 15-mer peptide.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A coupling agent having a formula selected from the group consisting of:

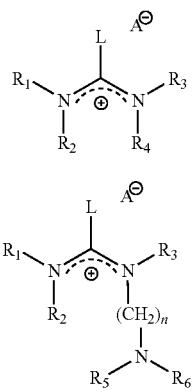

wherein:
- A is an inorganic anion;
- L is a leaving group selected from the group consisting of a benzotriazole, a benzotriazinone, a succinimide, a ketoxime, a pyridin-2(1H)-one-1-oxy, a quinazolin-4(3H)-one-3-oxy, a 1H-benzo[d]imidazol-1-oxy, an imidazole, an indolinone-1-oxy, pentafluorophenol, pentafluorothiophenol, 2-nitrophenol and 2-nitrobenzenethiol;
- n is an integer from 1 to 4,
- $R_1$, $R_2$, $R_3$, $R_4$, $R_5$ and $R_6$ are each independently an alkyl having 1-4 carbon atoms, or one of $R_1$ and $R_2$, and/or $R_3$ and $R_4$, and/or $R_5$ and $R_6$ are independently joined to form a heteroalicyclic moiety selected from the group consisting of pyrrolidine, piperidine, morpholine, a thiomorpholine, a imidazolidine, an azaphosphinane, an azaphospholidine, an azaborinane, an azaborolidine, and a piperazine,
- provided that one of $R_1$ and $R_2$, and/or $R_3$ and $R_4$, and/or $R_5$ and $R_6$ are joined to form said heteroalicyclic moiety.

2. The coupling agent of claim 1, wherein said heteroalicyclic moiety is morpholine.

3. The coupling agent of claim 1, wherein said inorganic anion is selected from the group consisting of halide, hexahalophosphate, hexahaloantimonate, tetrahaloborate, trihalomethanesulfonate and bis(trihalomethylsulfonyl)imide.

4. The coupling agent of claim 1, wherein said inorganic anion is hexafluorophosphate.

5. The coupling agent of claim 1, wherein said benzotriazole has the Formula III:

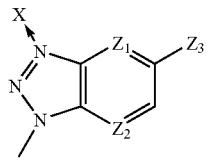

wherein:
- X is O or S;
- $Z_1$ and $Z_2$ are each independently CH or N; and
- $Z_3$ is F, Cl, Br, $CF_3$ or $NO_2$.

6. The coupling agent of claim 1, wherein said benzotriazinone has the Formula IV:

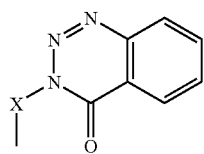

wherein X is O or S.

7. The coupling agent of claim 1, wherein said succinimide has the Formula V:

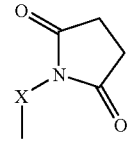

wherein X is O or S.

8. The coupling agent of claim 1, wherein said ketoxime has the Formula VI:

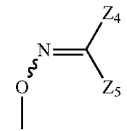

wherein:
- $Z_4$ and $Z_5$ are each independently selected from the group consisting of F, Cl, Br, CORa, COORa, CONRa, CN, $CF_3$ or $NO_2$; and
- Ra is alkyl.

9. The coupling agent of claim 1, wherein said pyridin-2(1H)-one-1-oxy has the Formula VII:

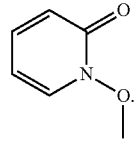

10. The coupling agent of claim 1, wherein said quinazolin-4(3H)-one-3-oxy has the Formula VIII:

Formula VIII wherein:
$Z_6$ and $Z_7$ are each independently selected from the group consisting of H, F, Cl, Br, CN, $CF_3$, $NO_2$, aryl or alkyl.

11. The coupling agent of claim 1, wherein said 1H-benzo[d]imidazol-1-oxy has the Formula IX:

Formula IX wherein:
$Z_1$ is CH or N;
$Z_8$ and $Z_9$ are each independently selected from the group consisting of H, F, Cl, Br, CN, $CF_3$, $NO_2$, aryl or alkyl.

12. The coupling agent of claim 1, wherein said indolinone-1-oxy has the Formula X:

Formula X wherein:
$Z_{10}$ is selected from the group consisting of H, F, Cl, Br, CN, $CF_3$, $NO_2$, aryl or alkyl.

13. The coupling agent of claim 5, wherein:
X is O or S;
$Z_1$ and $Z_2$ are each CH; and
$Z_3$ is Cl.

14. The coupling agent of claim 13, wherein X is O.

15. The coupling agent of claim 8, wherein:
$Z_4$ is COORa;
Ra is ethyl; and
$Z_5$ is CN.

16. The coupling agent of claim 8, wherein:
$Z_4$ and $Z_5$ are each independently COORa or CN; and
Ra is methyl.

17. The coupling agent of claim 10, wherein:
$Z_6$ is $CH_3$; and
$Z_7$ is Cl.

18. The coupling agent of claim 11, wherein
$Z_1$ is CH;
$Z_6$ is phenyl; and
$Z_7$ is H or Cl.

19. The coupling agent of claim 11, wherein
$Z_1$ is N;
$Z_6$ is methyl; and
$Z_7$ is H.

20. A coupling agent selected from the group consisting of:

-continued

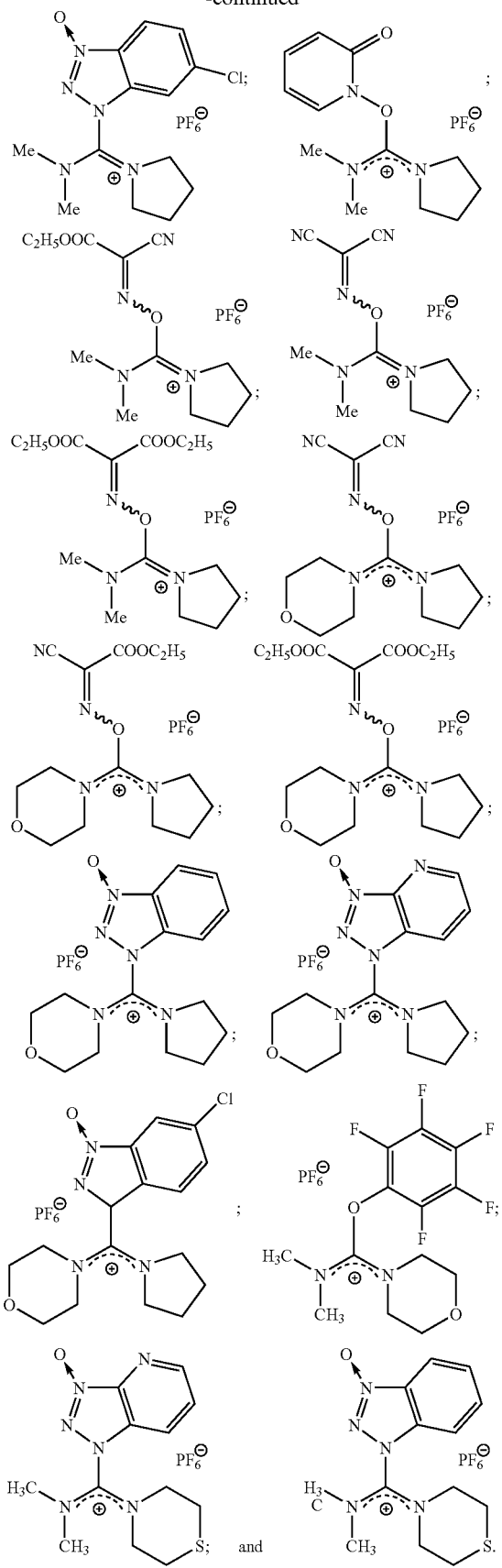

21. A coupling agent being

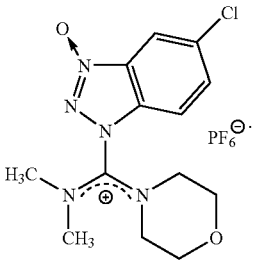

22. A process of preparing the coupling agent of claim 1, the process comprising:
    contacting a compound having a formula selected from the group consisting of:

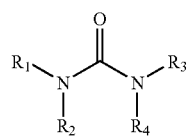

Formula XI

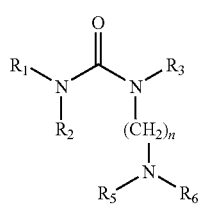

Formula XII wherein:
$R_1$, $R_2$, $R_3$, $R_4$, $R_5$ and $R_6$ are each independently an alkyl having 1-4 carbon atoms or $R_1$ and $R_2$, and/or $R_3$ and $R_4$, and/or $R_5$ and $R_6$ are independently joined to form said heteroalicyclic moiety
provided that
one of $R_1$ and $R_2$, and/or $R_3$ and $R_4$, and/or $R_5$ and $R_6$ are joined to form said heteroalicyclic moiety; and
n is an integer from 1 to 4;
with:
(i) a halogenating agent; and
(ii) a saturated aqueous solution of said inorganic anion, to thereby obtain a coupling agent having said Formula I or II, in which L is halo; and
(iii) reacting said coupling agent in which L is halo with a precursor compound of said leaving group in the presence of triethylamine,
thereby obtaining the coupling agent.

23. The process of claim 22, further comprising, prior to said contacting:
reacting a compound having the Formula XIII:

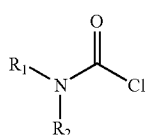

Formula XIII wherein $R_1$ and $R_2$ are each independently an alkyl having 1-4 carbon atoms or $R_1$ and $R_2$ are joined to form said heteroalicyclic moiety;

with a compound having the Formula XIV:

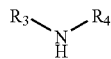

Formula XIV wherein $R_3$ and $R_4$ are each independently an alkyl having 1-4 carbon atoms or $R_3$ and $R_4$ are joined to form said heteroalicyclic moiety;
in the presence of a base, to thereby obtain the compound having the Formula XI;
or with a compound having the Formula XV:

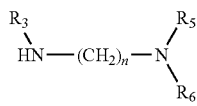

Formula XV wherein:
wherein $R_3$, $R_5$ and $R_6$ are each independently an alkyl having 1-4 carbon atoms, or $R_5$ and $R_6$ are joined to form said heteroalicyclic moiety; and
n is an integer from 1 to 4;
in the presence of a base, to thereby obtain the compound having the Formula XII.

24. A method of synthesizing a peptide, the method comprising:
coupling a plurality of amino acids sequentially, one with another, in the presence of the coupling agent of claim 1, to thereby obtain a peptide containing said plurality of amino acids.

25. The method of claim 24, wherein a rate of racemization per each coupling step ranges from 8% to 0.3%.

26. The method of claim 24, wherein a yield of coupling per each coupling step ranges from 80% to 99%.

27. The method of claim 25, wherein at least one of said amino acids is selected from the group consisting of an amino acid having a secondary alpha amine, an amino acid having a tertiary alpha amine, an amino acid having a substituted alpha carbon atom, an amino acid having a substituted alpha amine, an amino acid having an amino-containing side chain, and any combination thereof.

28. The method of claim 27, wherein said alpha carbon is substituted by an alkyl.

29. The method of claim 28, wherein said amino acid having said substituted alpha carbon atom is α-aminoisobutyric acid (Aib).

30. The method of claim 27, wherein said amino acid having said substituted alpha amine is phenylglycine (Phg).

31. The method of claim 27, wherein said amino acid having said amino-containing side chain is arginine.

32. A method of synthesizing a polynucleotide, the method comprising:
coupling a plurality of nucleotides sequentially, one with another, in the presence of the coupling agent of claim 1, to thereby obtain a polynucleotide containing said plurality of nucleotides.

33. A crude composition of peptides, said peptides being synthesized in a C-terminus to N-terminus direction from a plurality of amino acids, the composition consisting essentially of a peptide having a desired amino acid sequence and a plurality of peptides having undesired amino acid sequences and being impurities to said peptide having said desired amino acid sequence, wherein a concentration of said peptide having said desired amino acid sequence in said composition is at least 5% above a concentration of an identical peptide having said desired amino acid sequence, in a composition of peptides being synthesized in said C-terminus to N-terminus direction using the coupling agent of claim 1 as a coupling agent, otherwise prepared under identical conditions.

34. The composition of claim 33, wherein at least one of said amino acids is selected from the group consisting of an amino acid having a secondary alpha amine, an amino acid having a tertiary alpha amine, an amino acid having a substituted alpha carbon atom, an amino acid having a substituted alpha amine, an amino acid having an amino-containing side chain, and any combination thereof.

35. A coupling agent having a formula selected from the group consisting of:

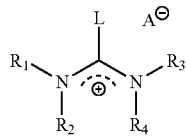

Formula I

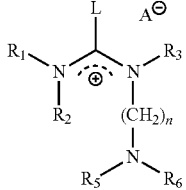

Formula II wherein:
A is an inorganic anion;
L is a ketoxime leaving group having the Formula VI:

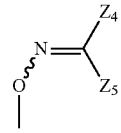

Formula VI $Z_4$ and $Z_5$ are each independently selected from the group consisting of F, Cl, Br, CORa, COORa, CONRa, CN, $CF_3$ or $NO_2$ and Ra is;
n is an integer from 1 to 4,
$R_1$, $R_2$, $R_3$, $R_4$, $R_5$ and $R_6$ are each independently an alkyl having 1-4 carbon atoms and an alkyl having 1-4 carbon atoms or $R_1$ and $R_2$, and/or $R_3$ and $R_4$, and/or $R_5$ and $R_6$ are each independently joined to form a heteroalicyclic moiety selected from the group consisting of a pyrrolidine, piperidine, morpholine, a thiomorpholine, a imidazolidine, an azaphosphinane, an azaphospholidine, an azaborinane, an azaborolidine, and a piperazine,
provided that:
at least one of $R_1$ and $R_2$, and/or $R_3$ and $R_4$, and/or $R_5$ and $R_6$ are joined to form said heteroalicyclic moiety.

36. The coupling agent of claim 35, wherein said heteroalicyclic moiety is morpholine.

37. The coupling agent of claim 35, wherein said inorganic anion is selected from the group consisting of halide, hexahalophosphate, hexahaloantimonate, tetrahaloborate, trihalomethanesulfonate and bis(trihalomethylsulfonyl)imide.

38. The coupling agent of claim 35, wherein said inorganic anion is hexafluorophosphate.

39. The coupling agent of claim 35, selected from the group consisting of:

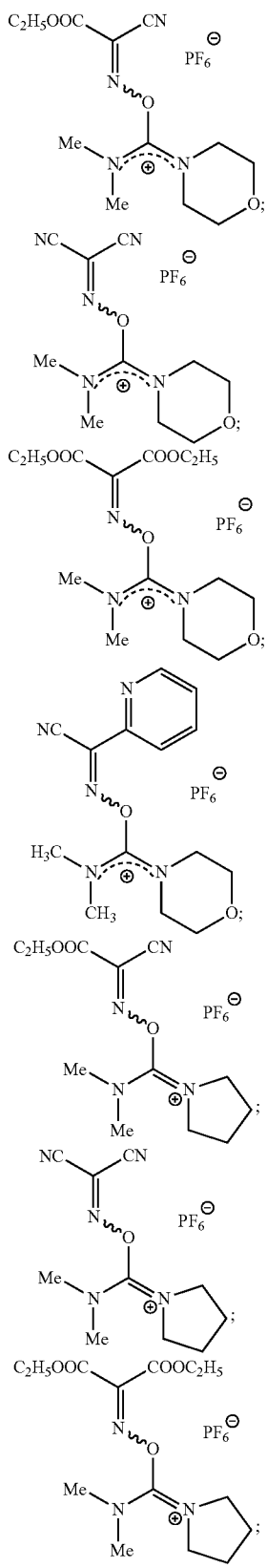

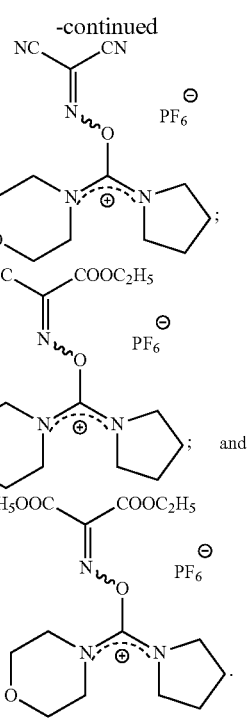

40. A coupling agent being

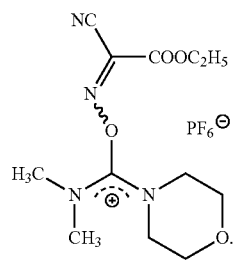

41. A method of synthesizing a peptide, the method comprising:

coupling a plurality of amino acids sequentially, one with another, in the presence of the coupling agent of claim 35, to thereby obtain a peptide containing said plurality of amino acids.

42. The method of claim 41, wherein a rate of racemization per each coupling step ranges from 8% to 0.3%.

43. The method of claim 41, wherein at least one of said amino acids is selected from the group consisting of an amino acid having a secondary alpha amine, an amino acid having a tertiary alpha amine, an amino acid having a substituted alpha carbon atom, an amino acid having a substituted alpha amine, an amino acid having an amino-containing side chain, and any combination thereof.

44. A method of synthesizing a polynucleotide, the method comprising:

coupling a plurality of nucleotides sequentially, one with another, in the presence of the coupling agent of claim 35, to thereby obtain a polynucleotide containing said plurality of nucleotides.

* * * * *